(12) United States Patent
Hilpert et al.

(10) Patent No.: US 9,409,917 B2
(45) Date of Patent: Aug. 9, 2016

(54) HETEROCYCLIC AMIDE DERIVATIVES AS P2X7 RECEPTOR ANTAGONISTS

(71) Applicants: Kurt Hilpert, Hofstetten (CH); Francis Hubler, Hegenheim (FR); Thierry Kimmerlin, Riehen (CH); Dorte Renneberg, Basel (CH); Simon Stamm, Allschwil (CH)

(72) Inventors: Kurt Hilpert, Hofstetten (CH); Francis Hubler, Hegenheim (FR); Thierry Kimmerlin, Riehen (CH); Dorte Renneberg, Basel (CH); Simon Stamm, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/373,338

(22) PCT Filed: Jan. 18, 2013

(86) PCT No.: PCT/IB2013/050479
§ 371 (c)(1),
(2) Date: Jul. 18, 2014

(87) PCT Pub. No.: WO2013/108227
PCT Pub. Date: Jul. 25, 2013

(65) Prior Publication Data
US 2015/0025075 A1    Jan. 22, 2015

(30) Foreign Application Priority Data

Jan. 20, 2012  (WO) .................. PCT/IB2012/050282

(51) Int. Cl.
*C07D 491/048*    (2006.01)

(52) U.S. Cl.
CPC ................................ *C07D 491/048* (2013.01)

(58) Field of Classification Search
CPC ................................................ C07D 491/048
See application file for complete search history.

(56) References Cited

U.S. PATENT DOCUMENTS

| | | | |
|---|---|---|---|
| 2007/0281939 A1 | 12/2007 | Dombrowski et al. | |
| 2012/0157494 A1 | 6/2012 | Harris, III et al. | |
| 2014/0073651 A1 | 3/2014 | Hilpert et al. | |
| 2014/0163035 A1 | 6/2014 | Hilpert et al. | |

FOREIGN PATENT DOCUMENTS

| | | | |
|---|---|---|---|
| EP | 2 243 772 A1 | 10/2010 | |
| WO | WO 00/61569 | 10/2000 | |
| WO | WO 01/42194 A1 | 6/2001 | |
| WO | WO 01/44170 A1 | 6/2001 | |
| WO | WO 01/94338 A1 | 12/2001 | |
| WO | WO 03/041707 A1 | 5/2003 | |
| WO | WO 03/042190 A1 | 5/2003 | |
| WO | WO 03/042191 A1 | 5/2003 | |
| WO | WO 03/080579 A1 | 10/2003 | |
| WO | WO 2004/058270 A1 | 7/2004 | |
| WO | WO 2004/058731 A1 | 7/2004 | |
| WO | WO 2004/074224 A1 | 9/2004 | |
| WO | WO 2004/106305 A1 | 9/2004 | |
| WO | WO 2004/099146 A1 | 11/2004 | |
| WO | WO 2005/009968 A1 | 2/2005 | |
| WO | WO 2005/111003 A1 | 11/2005 | |
| WO | WO 2006/025783 A1 | 3/2006 | |
| WO | WO 2006/059945 A1 | 6/2006 | |
| WO | WO 2006/080884 A1 | 8/2006 | |
| WO | WO 2006/102610 A2 | 9/2006 | |
| WO | WO 2007055374 A1 * | 5/2007 | |
| WO | WO 2007/109154 A2 | 9/2007 | |
| WO | WO 2007/109160 A2 | 9/2007 | |
| WO | WO 2007/109172 A2 | 9/2007 | |
| WO | WO 2007/109182 A2 | 9/2007 | |
| WO | WO 2007/109192 A2 | 9/2007 | |
| WO | WO 2007/109201 A2 | 9/2007 | |
| WO | WO 2007/141267 A1 | 12/2007 | |
| WO | WO 2007/141269 A1 | 12/2007 | |
| WO | WO 2008/003697 A1 | 1/2008 | |
| WO | WO 2008/066789 A2 | 6/2008 | |
| WO | WO 2008/094473 A1 | 8/2008 | |
| WO | WO 2008/112205 A1 | 9/2008 | |
| WO | WO 2008/114002 A1 | 9/2008 | |
| WO | WO 2008/116814 A1 | 10/2008 | |
| WO | WO 2008/116845 A1 | 10/2008 | |
| WO | WO 2008/119685 A2 | 10/2008 | |
| WO | WO 2008/119825 A2 | 10/2008 | |
| WO | WO 2008/124153 A1 | 10/2008 | |
| WO | WO 2008/125600 A2 | 10/2008 | |

(Continued)

OTHER PUBLICATIONS

Stock "Efficacy and Safety of CE-224,535, an Antagonist of P2X7 Receptor, in Treatment of Patients with Rheumatoid Arthritis Inadequately Controlled by Methotrexate" The Journal of Rheumatology 2012; 39:4; 720-727.*

Damia "Contemporary pre-clinical development of anticancer agents—What are the optimal preclinical models?" European Journal of Cancer 2009, 45, 2768-2781.*

Simone, Oncology: Introduction, Cecil Textbook of Medicine, 20th Edition, 1996 vol. 1, pp. 1004-1010.*

Sharma "Cell line-based platforms to evaluate the therapeutic efficacy of candidate anticancer agents" Nature Reviews Cancer Apr. 2010, vol. 10, 241-253.*

(Continued)

*Primary Examiner* — David K. O'Dell
(74) *Attorney, Agent, or Firm* — Hoxie & Associates LLC

(57) ABSTRACT

The invention relates to heterocyclic amide derivatives of formula (I),

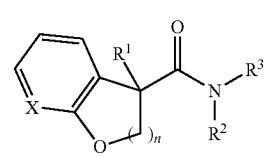

(I)

wherein $R^1$, $R^2$, $R^3$, X and n are as defined in the description, their preparation and their use as pharmaceutically active compounds.

16 Claims, No Drawings

(56) References Cited

FOREIGN PATENT DOCUMENTS

| WO | WO 2008/138876 A1 | 11/2008 |
|---|---|---|
| WO | WO 2009/012482 A2 | 1/2009 |
| WO | WO 2009/023623 A1 | 2/2009 |
| WO | WO 2009/070116 A1 | 6/2009 |
| WO | WO 2009/074518 A1 | 6/2009 |
| WO | WO 2009/074519 A1 | 6/2009 |
| WO | WO 2009/077362 A1 | 6/2009 |
| WO | WO 2009/077559 A2 | 6/2009 |
| WO | WO 2009/108551 A2 | 9/2009 |
| WO | WO 2009/118175 A1 | 10/2009 |
| WO | WO 2009/132000 A1 | 10/2009 |
| WO | WO 2011/054947 A1 | 5/2011 |
| WO | WO 2012/114268 A1 | 8/2012 |
| WO | WO 2012/163792 A1 | 12/2012 |
| WO | WO 2013/014587 A1 | 1/2013 |
| WO | WO 2014/091415 A1 | 6/2014 |
| WO | WO 2014/097140 | 6/2014 |
| WO | WO 2014/115072 | 7/2014 |
| WO | WO 2014/115078 | 7/2014 |

OTHER PUBLICATIONS

Ocana, A. "Preclinical development of molecular targeted agents for cancer" Nat. Rev. Clin. Oncol. 2011, 8, 200-209.*
Online "http://dtp.nci.nih.gov/docs/misc/common_files/submit_compounds.html" accessed Apr. 9, 2015.*
Julie, J.-P. "Transgenic mouse models of amyotrophic lateral sclerosis" Biochimica et Biophysica Acta 1762 (2006) 1013-1024.*
Johnson, et. al. "Relationships between drug activity in NCI preclinical in vitro and in vivo models and early clinical trials." British Journal of Cancer 2001, 84, 1424-1431.*
Bartlett "The P2X7 Receptor Channel: Recent Developments and the Use of P2X7 Antagonists in Models of Disease" Pharmacol Rev 66:638-675, Jul. 2014.*
Hook V. Y.H. "Neuroproteases in Peptide Neurotransmission and Neurodegenerative Diseases Applications to Drug Discovery Research" Biodrugs 2006, 20, 105-119.*
Yuzwa "O-GlcNAc and neurodegeneration: biochemical mechanisms and potential roles in Alzheimer's disease and beyond" Chem. Soc. Rev., 2014, 43, 6839.*
Jhee et. al. "B-amyloid therapies in Alzheimer's disease" Expert Opinion on Investigational Drugs 2001, 10, 593-605.*
Grazia D'Onofrio "Advances in the identification of g-secretase inhibitors for the treatment of Alzheimer's disease" Expert Opinion on Drug Discovery 2012, 7, 20-37.*
Sperlagh "P2X7 receptor: an emerging target in central nervous system diseases" Trends in Pharmacological Sciences, Oct. 2014, vol. 35, No. 10 537-547.*
Marcillo "A reassessment of P2X7 receptor inhibition as a neuroprotective strategy in rat models of contusion injury" Experimental Neurology 233 (2012) 687-692.*
Greenwood-Van Meerveld "Animal models of gastrointestinal and liver diseases. Animal models of visceral pain: pathophysiology, translational relevance, and challenges" Am J Physiol Gastrointest Liver Physiol 308: G885-G903, 2015.*
Le Bars, et. al. "Animal Models of Nociception" Pharmacological Reviews 2001, 53, 597-652.*
Reid "Epilepsy, energy deficiency and new therapeutic approaches including diet" Pharmacology & Therapeutics 144 (2014) 192-201.*
Abberley, L. et al., "Identification of 2-oxo-N-(phenylmethyl)-4-imidazolidinecarboxamide antagonists of the $P2X_7$ receptor", Bioorganic & Medicinal Chemistry Letters, vol. 20, (2010), pp. 6370-6374.
Abdi, M. H. et al., "Discovery and structure-activity relationships of a series of pyroglutamic acid amide antagonists of the $P2X_7$ receptor", Bioorganic & Medicinal Chemistry Letters, vol. 20, (2010), pp. 5080-5084.
Badarau, E. et al., "Synthesis of 3-Amino-8-azachromans and 3-Amino-7-azabenzofurans via Inverse Electron Demand Diels-Alder Reaction", Eur. J. Org. Chem., (2009), pp. 3619-3627.
Chen, X., et al., "Discovery of 2-chloro-N-((4,4-difluoro-1-hydroxycyclohexyl)methyl)-5-(5-flu-oropyrimidin-2-yl)benzamide as a potent and CNS penetrable $P2X_7$ receptor", Bioorganic & Medicinal Chemistry Letters vol. 20, (2010), pp. 3107-3111.
Chessell, I.P., et al., "Disruption of the $P2X_7$ purinoceptor gene abolishes chronic inflammatory and neuropathic pain", Pain (2005), vol. 114, (3), pp. 386-396.
De Graffenreid, M., et al., "An Efficient and Scalable One-Pot Double Michael Addition-Dieckmann Condensation for the Synthesis of 4,4-Disubstituted Cyclohexane β-Keto Esters", J.Org.Chem., vol. 72, pp. 7455-7458 (2007).
Deuchars, S. A., et al., "Neuronal $P2X_7$ Receptors are Targeted to Presynaptic Terminals in the Central and Peripheral Nervous Systems", J. Neurosci., (2001), vol. 21, (18), pp. 7143-7152.
Duplantier, A. J., et al., "Optimization of the physicochemical and pharmacokinetic attributes in a 6-azauracil series of $P2X_7$ receptor antagonists leading to the discovery of the clinical candidate CE-224-535", Bioorganic & Medicinal Chemistry Letter, vol. 21, (2011), pp. 3708-3711.
Ferrari, D., et al., "ATP-mediated Cytotoxicity in Microglial Cells", Neuropharmacology, (1997), vol. 36 (9), pp. 1295-1301.
Furber, M., et al., Discovery of Potent and Selective Adamantane-Based Small-Molecule $P2X_7$ Receptor Antagonists/Interleukin-1 β Inhibitors, J. Med. Chem., vol. 50, (2007), pp. 5882-5885.
Gould P., "Salt Selection for Basic Drugs", Int. J. Pharm. (1986), vol. 33, pp. 201-217.
Guile, S.D., et al., Antagonists of the $P2X_7$ Receptor. From Lead Identification to Drug Development, J. Med. Chem. vol. 52, No. 10, (2009), pp. 3123-3141, (published on web on Feb. 3, 2009, 10.1021/jm801528x).
Letavic, M.A., et al., "Synthesis and Pharmacological Characterization of Two Novel, Brain Penetrating $P2X_7$ Antagonists", ACS Med. Chem. Lett., vol. 4, (2013), p. 419-422.
Madsen-Duggan, C.B. et al., "Dihydro-pyrano[2,3-b]pyridines and tetrahydro-1,8-naphthyridines as CB1 receptor inverse agonists: Synthesis, SAR, and biological evaluation", Bioorganic & Medicinal Chemistry Letters, vol. 20 ; pp. 3750-3754 (2010).
Morita, H., et al., "Furopyridines. VI. Preparation and Reactions of 2- and 3-Substituted Furo [2,3-b]pyridines", J.Heterocyclic Chem., vol. 23, (1986), pp. 1465-1469.
North, R. A., "Molecular Physiology of P2X Receptors", Physiol. Rev. 2002, vol. 82, pp. 1013-1067.
Remington, The Science and Practice of Pharmacy, 21st Edition (2005), Part 5, "Pharmaceutical Manufacturing"
Solle, M., et al., "Altered Cytokine Production in Mice Lacking $P2X_7$ Receptors", J. Biol. Chem., (2001), vol. 276 (1), pp. 125-132.
Sperlagh, B., et al., "Involvement of $P2X_7$ Receptors in the Regulation of Neurotransmitter Release in the Rat Hippocampus", J. Neurochem. (2002), vol. 81, pp. 1196-1211.
Surprenant, A., et al., TheyCytolytic $P_{2z}$ Receptor for Extracellular ATP Identified as $P_{2x}$ Receptor ($P2X_7$), Science, (May 3, 1996), vol. 272, pp. 735-738.
Virginio, C., et al., "Kinetics of Cell Lysis, Dye Uptake and Permeability Changes in Cells Expressing the Rat $P2X_7$ Receptor", J. Physiol., (1999), vol. 519, No. 2, pp. 335-346.
J. S. Wiley et al., Ciba Found Symp. 198 (1996), pp. 149-160 and 160-165.
Yu, Y., et al., "Cellular Localization of P2X7 Receptor mRNA in the Rat Brain", Brain. Res. (2008), vol. 1194,, pp. 45-55.
Arbeloa, J., A. Perez-Samartin, et al. (2012). "P2X7 receptor blockade prevents ATP excitotoxicity in neurons and reduces brain damage after ischemia." Neurobiol Dis 45(3): 954-961.
Dell'Antonio, G., A. Quattrini, et al. (2002). "Antinociceptive effect of a new P(2Z)/P2X7 antagonist, oxidized ATP, in arthritic rats." Neurosci Lett 327(2): 87-90.
Eltom, S., C. S. Stevenson, et al. (2011). "P2X7 receptor and caspase 1 activation are central to airway inflammation observed after exposure to tobacco smoke." PLoS One 6(9): e24097.
Engel, T., A. Jimenez-Pacheco, et al. (2012). "P2X7 receptor in epilepsy; role in pathophysiology and potential targeting for seizure control." Int J Physiol Pathophysiol Pharmacol 4(4): 174-187.
Eser, A., J. F. Colombel, et al. (2015). "Safety and Efficacy of an Oral Inhibitor of the Purinergic Receptor P2X7 in Adult Patients with

(56) References Cited

OTHER PUBLICATIONS

Moderately to Severely Active Crohn's Disease: A Randomized Placebo-controlled, Double-blind, Phase IIa Study." *Inflamm Bowel Dis.* vol. 0, No. 0 Mar. 2015.

Gandelman, M., H. Peluffo, et al. (2010). "Extracellular ATP and the P2X7 receptor in astrocyte-mediated motor neuron death: implications for amyotrophic lateral sclerosis." *J Neuroinflammation* 7:33.

Gulbransen, B. D., M. Bashashati, et al. (2012). "Activation of neuronal P2X7 receptor-pannexin-1 mediates death of enteric neurons during colitis." *Nat Med* 18(4): 600-604.

Honore, P. et al. (2006). "A-740003 [N-(1-{[(cyanoimino)(5-quinolinylamino) methyl]amino }-2,2-dimethylpropyl)-2-(3,4-dimethoxyphenyl)acetamide], a novel and selective P2X7 receptor antagonist, dose-dependently reduces neuropathic pain in the rat." *J Pharmacol Exp Ther* 319(3): 1376-1385.

Keating, C., P. Pelegrin, et al. (2011). "P2X7 receptor-dependent intestinal afferent hypersensitivity in a mouse model of postinfectious irritable bowel syndrome." *J Immunol* 187(3): 1467-1474.

Lang, P. A., D. Merkler, et al. (2010). "Oxidized ATP inhibits T-cell-mediated autoimmunity." *Eur J Immunol* 40(9): 2401-2408.

Mezzaroma, E., S. Toldo, et al. (2011). "The inflammasome promotes adverse cardiac remodeling following acute myocardial infarction in the mouse." *Proc Natl Acad Sci U S A* 108(49): 19725-19730.

Muller, T., R. P. Vieira, et al. (2011). "A potential role for P2X7R in allergic airway inflammation in mice and humans." *Am J Respir Cell Mol Biol* 44(4): 456-464.

Pastore, S., F. Mascia, et al. (2007). "Stimulation of purinergic receptors modulates chemokine expression in human keratinocytes." *J Invest Dermatol* 127(3): 660-667.

Peng, W., M. L. Cotrina, et al. (2009). "Systemic administration of an antagonist of the ATP-sensitive receptor P2X7 improves recovery after spinal cord injury." *Proc Natl Acad Sci U S A* 106(30): 12489-12493.

Sanz, J. M., P. Chiozzi, et al. (2009). "Activation of microglia by amyloid {beta} requires P2X7 receptor expression." *J Immunol* 182(7): 4378-4385.

Subramanyam, et al. (2011) "Discovery synthesis and SAR of Azinyl-and Azolybenzamides antagonists of the P2X7 receptor" BioOrganic Medicinal Chemistry Letters, vol. 21, pp. 5475-5479.

Taylor, S. R., C. M. Turner, et al. (2009). "P2X7 deficiency attenuates renal injury in experimental glomerulonephritis." *J Am Soc Nephrol* 20(6): 1275-1281.

Wesselius, A., M. J. Bours, et al. (2011). "Role of purinergic receptor polymorphisms in human bone." *Front Biosci (Landmark Ed)* 16: 2572-2585.

Broom et al; "Characterization of N-(Adamantan-1-ylmethyl)-5-[(3R-amino-pyrrolidin-1-yl)methyl]-2-chloro-benzamide, a P2X7 Antagonist in Animal Models of Pain and Inflammation"; The Journal of Pharmacology and Experimental Therapeutics, 327; pp. 620-633 (2008).

Clark et al; "P2X7-Dependent Release of Interleukin-1B and Nociception in the Spinal Cord Following Lipopolysaccharide"; The Journal of Neuroscience, 30(2), pp. 573-582; Jan. 13, 2010.

Dell' Antonio et al; "Relief of Inflammatory Pain in Rats by Local Use of the Selective P2X7 ATP Receptor Inhibitor, Oxidized ATP"; Arthritis & Rheumatism, 46:12, pp. 3378-3385; Dec. 2002.

McGaraughty et al; "P2X7-Related Modulation of Pathological Nociception in Rats"; Neuroscience, 146, pp. 1817-1828; (2007).

Ren et al; "Role of Interleukin-1B During Pain and Inflammation"; Brain Res Rev., 60(1); pp. 57-64; Apr. 2009.

Sorge et al; "Genetically Determined P2X7 Receptor Pore Formation Regulates Variability in Chronic Pain Sensitivity"; Nature Medicine 18:4; pp. 595-600; Apr. 2012.

\* cited by examiner

```
                            SEQUENCE LISTING

<160> NUMBER OF SEQ ID NOS: 2

<210> SEQ ID NO 1
<211> LENGTH: 35
<212> TYPE: DNA
<213> ORGANISM: Homo sapiens
<220> FEATURE:
<221> NAME/KEY: source
<222> LOCATION: 1..35
<223> OTHER INFORMATION: /mol_type="DNA"
      /organism="Homo sapiens"

<400> SEQUENCE: 1
atcgcggccg ctcagtaagg actcttgaag ccact                              35

<210> SEQ ID NO 2
<211> LENGTH: 38
<212> TYPE: DNA
<213> ORGANISM: Homo sapiens
<220> FEATURE:
<221> NAME/KEY: source
<222> LOCATION: 1..38
<223> OTHER INFORMATION: /mol_type="DNA"
      /organism="Homo sapiens"

<400> SEQUENCE: 2
cgccgctagc accaccatgc cggcctgctg cagctgca                           38
```

HETEROCYCLIC AMIDE DERIVATIVES AS P2X7 RECEPTOR ANTAGONISTS

CROSS REFERENCE TO RELATED APPLICATIONS

This application is a U.S. application under 35 U.S.C. 371 claiming benefit of PCT Application No. PCT/IB2013/050479, filed on Jan. 18, 2013, which claims priority to PCT Application No. PCT/IB2012/050282, filed on Jan. 20, 2012, the contents of each of which are incorporated herein by reference.

REFERENCE TO SEQUENCE LISTING

This application includes an electronic sequence listing, the contents of which are incorporated herein by reference. The sequence listing is an ASCII text file with the title "Act_249A_sequence_listing", created on Jul. 15, 2014, with a size of 697 bytes.

The present invention relates to heterocyclic amide derivatives of formula (I) and their use as pharmaceuticals. The invention also concerns related aspects including processes for the preparation of the compounds, pharmaceutical compositions containing one or more compounds of formula (I), and especially their use as $P2X_7$ receptor antagonists.

The $P2X_7$ receptors (P2RX7) belong to the family of P2X ionotropic receptors that are activated by extracellular nucleotides, in particular adenosine triphosphate (ATP). P2RX7 is distinguished from other P2X family members by the high concentrations (mM range) of ATP required to activate it and its ability to form a large pore upon prolonged or repeated stimulation (North, R. A., Physiol. Rev. 2002, 82(4), 1013-67; Surprenant, A., Rassendren, F. et al., Science 1996, 272(5262), 735-8; Virginio, C., MacKenzie, A. et al., J. Physiol., 1999, 519, 335-46). P2RX7 is present on many cell types, especially ones known to be involved in inflammatory and immune processes. This is reflected within both the periphery and the CNS as Lipopolysaccharide S (LPS) priming of monocytes and microglia followed by ATP stimulation has been shown to lead to the local release and processing of IL1β and other family members including IL18 through a P2RX7 mediated mechanism. Indeed mice lacking the P2X7 receptor are unable to release IL1β following LPS priming and ATP stimulation providing further evidence of its role in this pathway (Solle, M., Labasi, J. et al., J. Biol. Chem., 2001, 276(1), 125-32). In addition L-selectin shedding from monocytes, macrophages and lymphocytes, degranulation in mast cells and apoptosis in lymphocytes are all associated with P2RX7 stimulation. P2RX7 is also expressed on epithelial and endothelial cells (Ferrari, D., Chiozzi, P. et al., Neuropharmacology 1997, 36(9), 1295-301; Wiley, J. S., Chen, J. R. et al., Ciba Found Symp. 1996, 198, 149-60 and 160-5; North, R. A., Physiol. Rev. 2002, 82(4), 1013-67). In addition to its role in the periphery it may have an important function in neurotransmission within the CNS through its activation on postsynaptic and/or presynaptic central and peripheral neurons and glia (Deuchars, S. A., Atkinson, L. et al., J. Neurosci. 2001, 21(18), 7143-52; Sperlagh, B., Kofalvi, A. et al., J. Neurochem. 2002, 81(6), 1196-211). Recent data that has emerged using in situ hybridization demonstrated that P2X7 receptor mRNA was widely distributed throughout the rat brain. Specifically, among the areas of high P2X7mRNA expression noted were the piriform cortex, hippocampus, pontine nuclei and the anterior horn of the spinal cord (Yu, Y., Ugawa, S. et al., Brain. Res. 2008, 1194, 45-55). Hence there is therapeutic rationale for the use of P2X7 ion channel blockers in the treatment of a variety of disease states. These include but are not limited to diseases associated with the central nervous system such as stroke or injury and diseases associated with neuro-degeneration and neuroinflammation such as Alzheimer's disease, Huntington's disease, epilepsy, Amyotrophic lateral sclerosis, acute spinal cord injury additionally to meningitis, sleep disorders, mood and anxiety disorders as well as chronic and neuropathic and inflammatory pain. Furthermore, peripheral inflammatory disorders and autoimmune diseases including but not limited to rheumatoid arthritis, osteoarthritis, psoriasis, allergic dermatitis, asthma, chronic obstructive pulmonary disease, airways hyper-responsiveness, septic shock, bronchitis, glomerulonephritis, irritable bowel disease, skin injury, lung emphysema, Limb girdle dystrophy type 2B, fibrosis, Syndrome of synovitis Acne Pustulosis, atherosclerosis, burn injury, spinal cord injury, Hyperostosis Osteitis, Crohn's disease, ulcerative colitis, growth and metastases of malignant cells, myoblastic leukaemia, diabetes, trauma, meningitis, osteoporosis, burn injury, ischemic heart disease, and varicose veins and trauma, are all examples where the involvement of P2X7 channels has been implicated. In addition a recent report suggests a link between P2RX7 and chronic, inflammatory and neuropathic pain (Chessell, I. P., Hatcher, J. P. et al., Pain, 2005, 114(3), 386-96). Overall, these findings indicate a role for the P2X7 receptor in the process of neuronal synaptic transmission and therefore a potential role for P2X7 antagonists as novel therapeutic tools to treat neuropathic pain.

In view of the above observations, there is significant requirement for P2X7 antagonists that can be efficiently used in treating neuropathic pain, chronic inflammatory pain, inflammation, and neurodegenerative conditions.

A different dihydrofuropyridine derivative, which is also a $P2X_7$ receptor antagonist, has been disclosed in WO 2005/111003.

Various embodiments of the invention are presented hereafter:
1) The present invention relates to heterocyclic amide derivatives of formula (I),

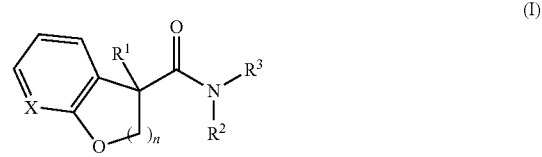

wherein
n represents 1 or 2;
X represents —N— or —N(O)—;
$R^1$ represents hydrogen or halogen (preferably hydrogen or fluorine);
$R^2$ represents hydrogen or methyl; and
$R^3$ represents
aryl-$(C_1-C_3)$alkyl, which is in the alkyl part optionally mono-substituted with hydroxy or heterocyclyl; and which is in the aryl part mono-, di- or tri-substituted, wherein the substituents are independently selected from the group consisting of $(C_1-C_4)$alkyl, $(C_2-C_4)$alkenyl, $(C_3-C_6)$cycloalkyl, $(C_1-C_4)$alkoxy, hydroxy-$(C_1-C_3)$alkyl, hydroxy-$(C_2-C_3)$alkoxy, hydroxy-$(C_2-C_3)$alkoxy-$(C_1-C_2)$alkyl, $(C_1-C_2)$alkoxy-$(C_1-C_2)$alkyl, $(C_1-C_3)$fluoroalkyl, $(C_1-C_3)$fluoroalkoxy, cyano, halogen and phenoxy; or heteroaryl-$(C_1$-$C_3)$alkyl, which is in the alkyl part monosubstituted with heterocyclyl; and which is in the heteroaryl part mono-, di- or tri-substituted, wherein the substituents are independently selected from the group consisting of $(C_1$-$C_4)$alkyl, $(C_3$-$C_6)$cycloalkyl, $(C_1$-$C_4)$ alkoxy, $(C_1$-$C_3)$fluoroalkyl and halogen; or $(C_3$-$C_7)$cycloalkyl, which is monosubstituted with —C(O)NH$_2$ or an optionally mono-, di- or tri-substituted phenyl, wherein the substituents are selected from halogen; or $(C_5$-$C_7)$cycloalkyl, which is optionally mono-substituted with hydroxy or oxo; and which is annelated with an optionally mono-, di- or tri-substituted phenyl, wherein the substituents are selected from halogen; or $(C_3$-$C_7)$cycloalkyl-$(C_1$-$C_3)$alkyl, which is in the alkyl part optionally mono-substituted with hydroxy; and which is in the cycloalkyl part optionally di-substituted with halogen and optionally mono-substituted with hydroxy, aryl or heteroaryl, wherein the aryl or heteroaryl groups are optionally mono-, di- or tri-substituted with halogen; and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to four carbon atoms. The term "$(C_x$-$C_y)$alkyl" (x and y each being an integer), refers to an alkyl group as defined before containing x to y carbon atoms. For example a $(C_1$-$C_4)$alkyl group contains from one to four carbon atoms. In one embodiment the hydrogen isotopes in any alkyl group may be present according to their natural abundance or one, two or three hydrogen atoms of an alkyl group may be replaced by deuterium atoms. In a preferred embodiment the hydrogen isotopes in any alkyl group may be present according to their natural abundance. Representative examples of alkyl groups include methyl, ethyl, n-propyl, iso-propyl, n-butyl, iso-butyl, sec-butyl and tert-butyl. Further examples are trideuteromethyl and 2,2,2-trideuteroethyl. The alkyl group may be unsubstituted or substituted as explicitly defined.

In case a $(C_1$-$C_4)$alkyl group is a substituent to an aryl group, the term "$(C_1$-$C_4)$alkyl" means $(C_1$-$C_4)$alkyl groups as defined above. Examples of said groups are methyl, ethyl, n-propyl, iso-propyl, n-butyl, iso-butyl, sec-butyl and tert-butyl. Further examples are trideuteromethyl and 2,2,2-trideuteroethyl. Preferred are methyl, trideuteromethyl and ethyl. More preferred are methyl and ethyl and most preferred is methyl.

In case a $(C_1$-$C_4)$alkyl group is a substituent to a heteroaryl group, the term "$(C_1$-$C_4)$alkyl" means $(C_1$-$C_4)$alkyl groups as defined above. Examples of said groups are methyl, ethyl, n-propyl, iso-propyl, n-butyl, iso-butyl, sec-butyl and tert-butyl. Preferred are methyl and ethyl and most preferred is methyl.

The term "aryl-$(C_x$-$C_y)$alkyl" (x and y each being an integer) refers to an alkyl group as defined before containing x to y carbon atoms in which one hydrogen atom has been replaced with aryl as defined below. For example an aryl-$(C_1$-$C_3)$alkyl group refers to an alkyl group as defined before containing one to three carbon atoms in which one hydrogen atom has been replaced with aryl. Representative examples of aryl-$(C_1$-$C_3)$alkyl groups include aryl-methyl, 1-aryl-ethyl, 2-aryl-ethyl, 1-aryl-prop-1-yl, 2-aryl-prop-1-yl, 1-aryl-prop-2-yl, 2-aryl-prop-2-yl and 3-aryl-prop-1-yl. Preferred are aryl-methyl, 1-aryl-ethyl and 2-aryl-ethyl; more preferred are aryl-methyl and 1-aryl-ethyl; and most preferred is aryl-methyl. The alkyl moiety of the aryl-$(C_1$-$C_3)$alkyl group may be unsubstituted or substituted as explicitly defined. In case the alkyl moiety is substituted, it is preferred that the nitrogen atom of the amide moiety and a heteroatom of the substituent are not attached to the same carbon atom of the alkyl moiety.

The term "heteroaryl-$(C_x$-$C_y)$alkyl" (x and y each being an integer) refers to an alkyl group as defined before containing x to y carbon atoms in which one hydrogen atom has been replaced with heteroaryl as defined below. For example an heteroaryl-$(C_1$-$C_3)$alkyl group refers to an alkyl group as defined before containing one to three carbon atoms in which one hydrogen atom has been replaced with heteroaryl. Representative examples of heteroaryl-$(C_1$-$C_3)$alkyl groups include heteroaryl-methyl, 1-heteroaryl-ethyl, 2-heteroaryl-ethyl, 1-heteroaryl-prop-1-yl, 2-heteroaryl-prop-1-yl, 1-heteroaryl-prop-2-yl, 2-heteroaryl-prop-2-yl and 3-heteroaryl-prop-1-yl. Preferred are heteroaryl-methyl, 1-heteroaryl-ethyl and 2-heteroaryl-ethyl; most preferred is 2-heteroaryl-ethyl. The alkyl moiety of the heteroaryl-$(C_1$-$C_3)$alkyl group may be unsubstituted or substituted as explicitly defined. In case the alkyl moiety is substituted, it is preferred that the nitrogen atom of the amide moiety and a heteroatom of the substituent are not attached to the same carbon atom of the alkyl moiety.

The term "$(C_3$-$C_7)$cycloalkyl-$(C_x$-$C_y)$alkyl" (x and y each being an integer) refers to an alkyl group as defined before containing x to y carbon atoms in which one hydrogen atom has been replaced with $(C_3$-$C_7)$cycloalkyl as defined below. For example a $(C_3$-$C_7)$cycloalkyl-$(C_1$-$C_3)$alkyl group refers to an alkyl group as defined before containing one to three carbon atoms in which one hydrogen atom has been replaced with $(C_3$-$C_7)$cycloalkyl. Representative examples of $(C_3$-$C_7)$cycloalkyl-$(C_1$-$C_3)$alkyl groups include $(C_3$-$C_7)$cycloalkyl-methyl, 1-$(C_3$-$C_7)$cycloalkyl-ethyl, 2-$(C_3$-$C_7)$cycloalkyl-ethyl, 1-$(C_3$-$C_7)$cycloalkyl-prop-1-yl, 2-$(C_3$-$C_7)$cycloalkyl-prop-1-yl, 1-$(C_3$-$C_7)$cycloalkyl-prop-2-yl, 2-$(C_3$-$C_7)$cycloalkyl-prop-2-yl and 3-$(C_3$-$C_7)$cycloalkyl-prop-1-yl. Preferred are $(C_3$-$C_7)$cycloalkyl-methyl and 1-$(C_3$-$C_7)$cycloalkyl-ethyl; most preferred is $(C_3$-$C_7)$cycloalkyl-methyl. The alkyl moiety of the $(C_3$-$C_7)$cycloalkyl-$(C_1$-$C_3)$alkyl group may be unsubstituted or substituted as explicitly defined. In case the alkyl moiety is substituted, it is preferred that the nitrogen atom of the amide moiety and a heteroatom of the substituent are not attached to the same carbon atom of the alkyl moiety.

The term "hydroxy-$(C_x$-$C_y)$alkyl" (x and y each being an integer) refers to an alkyl group as defined before containing x to y carbon atoms in which one hydrogen atom has been replaced with —OH. For example a hydroxy-$(C_1$-$C_3)$alkyl group refers to an alkyl group as defined before containing one to three carbon atoms in which one hydrogen atom has been replaced with —OH. Representative examples of hydroxy-$(C_1$-$C_3)$alkyl groups include hydroxy-methyl, 1-hydroxy-ethyl, 2-hydroxy-ethyl, 1-hydroxy-propyl, 2-hydroxy-propyl and 3-hydroxy-propyl. Preferred are hydroxy-methyl and 1-hydroxy-ethyl and most preferred is hydroxy-methyl.

The term "hydroxy-$(C_2-C_3)$alkoxy-$(C_x-C_y)$alkyl" (x and y each being an integer) refers to an alkyl group as defined before containing x to y carbon atoms in which one hydrogen atom has been replaced with hydroxy-$(C_2-C_3)$alkoxy as defined below. For example a hydroxy-$(C_2-C_3)$alkoxy-$(C_1-C_2)$alkyl group refers to an alkyl group as defined before containing one or two carbon atoms in which one hydrogen atom has been replaced with hydroxy-$(C_2-C_3)$alkoxy. Representative examples of hydroxy-$(C_2-C_3)$alkoxy-$(C_1-C_2)$alkyl groups include hydroxy-$(C_2-C_3)$alkoxy-methyl, 1-[hydroxy-$(C_2-C_3)$alkoxy]-ethyl and 2-[hydroxy-$(C_2-C_3)$alkoxy]-ethyl. Preferred is hydroxy-$(C_2-C_3)$alkoxy-methyl (and especially (2-hydroxy-ethoxy)-methyl).

The term "$(C_x-C_y)$fluoroalkyl" (x and y each being an integer) refers to an alkyl group as defined before containing x to y carbon atoms in which one or more (and possibly all) hydrogen atoms have been replaced with fluoro. For example a $(C_1-C_3)$fluoroalkyl group contains from one to three carbon atoms in which one to seven hydrogen atoms have been replaced with fluoro.

In case "$(C_1-C_3)$fluoroalkyl" is a substituent to an aryl or a heteroaryl group, the term "$(C_1-C_3)$fluoroalkyl" means $(C_1-C_3)$fluoroalkyl groups as defined above. Examples of said groups are difluoromethyl, trifluoromethyl, 2,2-difluoroethyl and 2,2,2-trifluoroethyl. Preferred is trifluoromethyl.

The term "alkenyl", used alone or in combination, refers to a straight or branched chain alkenyl group containing two to four carbon atoms. The term "$(C_x-C_y)$alkenyl" (x and y each being an integer), refers to an alkenyl group as defined before containing x to y carbon atoms. For example a $(C_2-C_4)$alkenyl group contains from two to four carbon atoms. Representative examples of $(C_2-C_4)$alkenyl groups include ethenyl, propenyl and butenyl. Preferred is ethenyl.

The term "alkoxy", used alone or in combination, refers to an alkyl-O— group wherein the alkyl group is as defined above. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy.

In case a $(C_1-C_4)$alkoxy group is a substituent to an aryl or a heteroaryl group, the term "$(C_1-C_4)$alkoxy" means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred are methoxy and ethoxy; and most preferred is methoxy.

The term "hydroxy-$(C_x-C_y)$alkoxy" (x and y being an integer), used alone or in combination, refers to an alkoxy group as defined before containing x to y carbon atoms in which one hydrogen atom has been replaced with —OH. For example a hydroxy-$(C_2-C_3)$alkoxy group refers to an alkoxy group as defined before containing two or three carbon atoms in which one hydrogen atom has been replaced with —OH. Representative examples of hydroxy-$(C_2-C_3)$alkoxy groups include 2-hydroxy-ethoxy, 2-hydroxy-prop-1-oxy, 3-hydroxy-prop-1-oxy and 1-hydroxy-prop-2-oxy. Preferred is 2-hydroxy-ethoxy.

The term "$(C_1-C_2)$alkoxy-$(C_1-C_2)$alkyl" refers to an alkyl group as defined before in which one hydrogen atom has been replaced with $(C_1-C_2)$alkoxy as defined before containing one or two carbon atoms. Representative examples of $(C_1-C_2)$alkoxy-$(C_1-C_2)$alkyl groups include methoxy-methyl, ethoxy-methyl, 1-methoxy-ethyl, 2-methoxy-ethyl, 1-ethoxy-ethyl and 2-ethoxy-ethyl. Preferred is methoxy-methyl.

The term "$(C_x-C_y)$fluoroalkoxy" (x and y each being an integer) refers to an alkoxy group as defined before containing x to y carbon atoms in which one or more (and possibly all) hydrogen atoms have been replaced with fluoro. For example a $(C_1-C_3)$fluoroalkoxy group contains from one to three carbon atoms in which one to seven hydrogen atoms have been replaced with fluoro.

In case "$(C_1-C_3)$fluoroalkoxy" is a substituent to an aryl group, the term "$(C_1-C_3)$fluoroalkoxy" means $(C_1-C_3)$fluoroalkoxy groups as defined above. Examples of said groups are difluoromethoxy, trifluoromethoxy, 2,2-difluoroethoxy and 2,2,2-trifluoroethoxy. Preferred is trifluoromethoxy.

The term "$(C_x-C_y)$cycloalkyl" (x and y each being an integer), used alone or in combination, means a cycloalkyl group containing x to y carbon atoms. For example a $(C_3-C_7)$cycloalkyl group contains from 3 to 7 carbon atoms; and a $(C_3-C_6)$cycloalkyl group contains from 3 to 6 carbon atoms. Examples of $(C_3-C_7)$cycloalkyl groups are cyclopropyl, cyclobutyl, cyclopentyl, cyclohexyl and cycloheptyl. Examples of $(C_3-C_6)$cycloalkyl groups are cyclopropyl, cyclobutyl, cyclopentyl and cyclohexyl. The cycloalkyl group may be unsubstituted or substituted as explicitly defined.

In case a $(C_3-C_6)$cycloalkyl group is a substituent to an aryl or a heteroaryl group, the term means $(C_3-C_6)$cycloalkyl groups as defined above. Examples of said groups are cyclopropyl, cyclobutyl, cyclopentyl and cyclohexyl. Preferred is cyclopropyl.

In case "$R^3$" represents "$(C_3-C_7)$cycloalkyl, which is monosubstituted with —C(O)NH$_2$ or an optionally mono-, di- or tri-substituted phenyl" the term "$(C_3-C_7)$cycloalkyl" means $(C_3-C_7)$cycloalkyl groups as defined above. Examples of said groups are cyclopropyl, cyclobutyl, cyclopentyl, cyclohexyl and cycloheptyl. Preferred are cyclopropyl, cyclopentyl and cyclohexyl. The cycloalkyl group is substituted as explicitly defined.

In case "$R^3$" represents "$(C_5-C_7)$cycloalkyl, which is optionally mono-substituted with hydroxy or oxo; and which is annelated with an optionally mono-, di- or tri-substituted phenyl" the term "$(C_5-C_7)$cycloalkyl which is annelated with an optionally mono-, di- or tri-substituted phenyl" means a $(C_5-C_7)$cycloalkyl group as defined above which is annelated with an optionally mono-, di- or tri-substituted phenyl group, wherein the cycloalkyl group and the phenyl group are unsubstituted or substituted as explicitly defined. Examples of said groups are indanyl (preferred), 1,2,3,4-tetrahydronaphthyl or 6,7,8,9-tetrahydro-5H-benzo[7]annulenyl, wherein the cycloalkyl group and the phenyl group are unsubstituted or substituted as explicitly defined. Preferred examples are indan-1-yl, 2-hydroxy-indan-1-yl, 3-oxo-indan-1-yl, 4,6-dichloro-indan-1-yl and 5,7-dichloro-indan-1-yl. Further preferred examples are 5-chloro-indan-1-yl, 7-chloro-indan-1-yl, 7-bromo-indan-1-yl, 5,7-dichloro-1-oxo-indan-2-yl, 1,2,3,4-tetrahydronaphthalen-1-yl and 8-chloro-1,2,3,4-tetrahydronaphthalen-1-yl. Most preferred is 5,7-dichloro-indan-1-yl. In case the $(C_5-C_7)$cycloalkyl moiety is substituted with hydroxy, it is preferred that the nitrogen atom of the amide moiety and the substituent are not attached to the same carbon atom of the $(C_5-C_7)$cycloalkyl moiety.

In case "$R^3$" represents "$(C_3-C_7)$cycloalkyl-$(C_1-C_3)$alkyl" the term "$(C_3-C_7)$cycloalkyl" means $(C_3-C_7)$cycloalkyl groups as defined above. Examples of said groups are cyclopropyl, cyclobutyl, cyclopentyl, cyclohexyl and cycloheptyl. Preferred are cyclohexyl and cycloheptyl. The cycloalkyl group is unsubstituted or substituted as explicitly defined.

The term halogen means fluoro, chloro, bromo or iodo, preferably fluoro, chloro or bromo.

In case "$R^1$" represents "halogen" the term means preferably fluoro, chloro or bromo; more preferably fluoro or chloro; and most preferably fluoro.

In case "halogen" is a substituent to an aryl, a phenyl or a heteroaryl group, the term "halogen" means fluoro, chloro, bromo or iodo; preferably fluoro, chloro or bromo; more preferably chloro or bromo; and most preferably chloro.

In case "halogen" is a substituent to a cycloalkyl or heterocyclyl group, the term "halogen" means fluoro, chloro, bromo or iodo; preferably fluoro or chloro; and most preferably fluoro.

The term "aryl", used alone or in any combination, means a phenyl or a naphthyl group.

Preferred is a phenyl group. The aryl group is unsubstituted or substituted as explicitly defined.

In case "$R^3$" represents "aryl-($C_1$-$C_3$)alkyl", the term "aryl" means phenyl or naphthyl. Preferred is a phenyl group. The aryl group is unsubstituted or substituted as explicitly defined. Examples are 4-chloro-phenyl, 2,3-dichloro-phenyl, 2,4-dichloro-phenyl, 2,4-dichloro-6-fluoro-phenyl, 2-chloro-4-fluoro-phenyl, 2-bromo-4,6-dichloro-phenyl, 3-chloro-2-methyl-phenyl, 2,4-dichloro-6-methyl-phenyl, 2,4-dichloro-6-ethyl-phenyl, 2,4-dichloro-6-cyclopropyl-phenyl, 2,4-dichloro-6-vinyl-phenyl, 2,4-dichloro-6-hydroxymethyl-phenyl, 2,4-dichloro-6-methoxy-phenyl, 2,4-dichloro-6-methoxymethyl-phenyl, 2,4-dichloro-6-(2-hydroxyethoxy)-phenyl, 2,4-dichloro-6-(2-hydroxy-ethoxymethyl)-phenyl, 2-chloro-3-trifluoromethyl-phenyl, 3-chloro-2-trifluoromethyl-phenyl, 2,4-dichloro-6-trifluoromethyl-phenyl, 3-fluoro-4-trifluoromethoxy-phenyl, 2-chloro-3-cyano-phenyl, 2-chloro-4-cyano-phenyl, 4-trifluoromethyl-phenyl and 4-phenoxy-phenyl. Further examples are 2,4,6-trichloro-phenyl, 2,4-dichloro-6-trideuteromethyl-phenyl, 2-chloro-6-hydroxymethyl-phenyl, 4-chloro-2-hydroxymethyl-phenyl and 2-chloro-4-trifluoromethyl-phenyl. Preferred examples are 2,3-dichloro-phenyl, 2,4-dichloro-phenyl, 2-bromo-4,6-dichloro-phenyl, 3-chloro-2-methyl-phenyl, 2,4-dichloro-6-methyl-phenyl, 2,4-dichloro-6-ethyl-phenyl, 2,4-dichloro-6-cyclopropyl-phenyl, 2,4-dichloro-6-vinyl-phenyl, 2,4-dichloro-6-hydroxymethyl-phenyl, 2,4-dichloro-6-methoxymethyl-phenyl, 2,4-dichloro-6-(2-hydroxy-ethoxymethyl)-phenyl, 2-chloro-3-trifluoromethyl-phenyl and 2,4-dichloro-6-trifluoromethyl-phenyl.

In case "aryl" is a substituent to a ($C_3$-$C_7$)cycloalkyl-($C_1$-$C_3$)alkyl group, the term "aryl" means phenyl or naphthyl. Preferred is a phenyl group. The aryl group is unsubstituted or substituted as explicitly defined. A preferred example is phenyl.

The term "heteroaryl", used alone or in combination, means a 5- to 10-membered monocyclic or bicyclic aromatic ring containing 1, 2 or 3 heteroatoms independently selected from oxygen, nitrogen and sulfur. Preferred is a 5- or 6-membered monocyclic aromatic ring containing 1, 2 or 3 heteroatoms (preferably 1 or 2 heteroatoms) independently selected from oxygen, nitrogen and sulphur (preferably from oxygen and nitrogen). Most preferred is a 6-membered monocyclic aromatic ring containing 1 or 2 nitrogen atoms. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, cinnolinyl, quinazolinyl, quinoxalinyl and phthalazinyl. Preferred examples are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl and pyrazinyl. The heteroaryl group is unsubstituted or substituted as explicitly defined.

In case "$R^3$" represents "heteroaryl-($C_1$-$C_3$)alkyl", the term "heteroaryl" means a heteroaryl group as defined above. Preferred is a 5- or 6-membered monocyclic aromatic ring containing 1, 2 or 3 heteroatoms (preferably 1 or 2 heteroatoms) independently selected from oxygen, nitrogen and sulphur (preferably from oxygen and nitrogen). Most preferred is a 6-membered monocyclic aromatic ring containing 1 or 2 nitrogen atoms. Preferred examples are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl and pyrazinyl. Most preferred examples are pyridyl (notably pyridin-3-yl) and pyrimidyl (notably pyrimidin-5-yl). The heteroaryl group is unsubstituted or substituted as explicitly defined. Preferred examples of unsubstituted or substituted heteroaryl groups are 2-chloro-pyridin-5-yl, 2-methyl-pyridin-5-yl, 2-methoxy-pyridin-5-yl, 2-trifluoromethyl-pyridin-5-yl, 2-methyl-pyrimidin-5-yl, 2-cyclopropyl-pyrimidin-5-yl and 2-trifluoromethyl-pyrimidin-5-yl. Most preferred are 2-chloro-pyridin-5-yl and 2-trifluoromethyl-pyrimidin-5-yl.

In case "heteroaryl" is a substituent to a ($C_3$-$C_7$)cycloalkyl-($C_1$-$C_3$)alkyl group, the term "heteroaryl" means a heteroaryl group as defined above. Preferred is a 5- or 6-membered monocyclic aromatic ring containing 1, 2 or 3 heteroatoms (preferably 1 or 2 heteroatoms) independently selected from oxygen, nitrogen and sulphur (preferably from oxygen and nitrogen). Most preferred is a 6-membered monocyclic aromatic ring containing 1 or 2 nitrogen atoms. Preferred examples are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl and pyrazinyl. More preferred examples are pyridyl (notably pyridin-3-yl) and pyrimidyl (notably pyrimidin-5-yl); most preferred is pyridyl (notably pyridin-3-yl). The heteroaryl group is unsubstituted or substituted as explicitly defined. A preferred example of an unsubstituted or substituted heteroaryl group is 2-chloro-pyridin-5-yl.

The term "heterocyclyl", used alone or in combination, refers to a saturated monocyclic moiety of 5 to 7 ring members containing 1 or 2 heteroatoms selected from nitrogen, oxygen and sulfur, it being understood that a heterocyclyl group does not contain 2 sulfur atoms. The sulfur atom of a heterocyclyl group may be in an oxidised form, i.e. as a sulfoxide or sulfonyl. Preferred is a saturated monocyclic moiety of 5 or 6 ring members (especially 6 ring members) containing 1 or 2 heteroatoms selected from nitrogen and oxygen. The heterocyclyl group is unsubstituted or substituted as explicitly defined.

In case "heterocyclyl" is a substituent to an aryl-($C_1$-$C_3$) alkyl group, the term "heterocyclyl" means a heterocyclyl group as defined above. Preferred is a saturated monocyclic moiety of 5 or 6 ring members (especially 6 ring members) containing 1 or 2 heteroatoms selected from nitrogen and oxygen. Examples of such heterocyclyl groups are pyrrolidinyl, imidazolidinyl, oxazolidinyl, thiazolidinyl, piperidinyl, piperazinyl, morpholinyl, thiomorpholinyl and dioxanyl. Preferred examples are piperidinyl (notably piperidin-1-yl) and morpholinyl (notably morpholin-4-yl); most preferred is piperidinyl (notably piperidin-1-yl). The heterocyclyl group is unsubstituted or mono- or di-substituted with halogen (notably fluorine). An example of an unsubstituted or mono- or di-substituted heterocyclyl group is 4,4-difluoro-piperidin-1-yl.

In case "heterocyclyl" is a substituent to a heteroaryl-($C_1$-$C_3$)alkyl group, the term "heterocyclyl" means a heterocyclyl group as defined above. Preferred is a saturated monocyclic moiety of 5 or 6 ring members (especially 6 ring members) containing 1 or 2 heteroatoms selected from nitrogen and oxygen. Examples of such heterocyclyl groups are pyrrolidinyl, imidazolidinyl, oxazolidinyl, thiazolidinyl, piperidinyl, piperazinyl, morpholinyl, thiomorpholinyl and dioxanyl. Preferred examples are piperidinyl (notably piperidin-1-yl) and morpholinyl (notably morpholin-4-yl). The heterocyclyl group is unsubstituted or mono- or di-substituted with halogen (notably fluorine). Examples of unsubstituted or mono- or di-substituted heterocyclyl groups are 4,4-difluoro-piperidin-1-yl and morpholin-4-yl.

2) A further embodiment of the invention relates to compounds according to embodiment 1), wherein
n represents 1 or 2;
X represents —N— or —N(O)—;
$R^1$ represents hydrogen or fluorine;
$R^2$ represents hydrogen; and
$R^3$ represents
  aryl-($C_1$-$C_2$)alkyl, which is in the aryl part mono-, di- or tri-substituted (preferably di- or tri-substituted), wherein the substituents are independently selected from the group consisting of ($C_1$-$C_4$)alkyl, ($C_2$-$C_4$)alkenyl, ($C_3$-$C_6$)cycloalkyl, ($C_1$-$C_4$)alkoxy, hydroxy-($C_1$-$C_3$)alkyl, hydroxy-($C_2$-$C_3$)alkoxy-($C_1$-$C_2$)alkyl, ($C_1$-$C_2$)alkoxy-($C_1$-$C_2$)alkyl, ($C_1$-$C_3$)fluoroalkyl and halogen; or
  heteroaryl-($C_1$-$C_2$)alkyl (preferably 2-heteroaryl-ethyl), which is in the alkyl part mono-substituted with heterocyclyl; and which is in the heteroaryl part mono- or di-substituted (preferably mono-substituted), wherein the substituents are independently selected from the group consisting of ($C_1$-$C_4$)alkyl, ($C_1$-$C_3$)fluoroalkyl and halogen (preferably from ($C_1$-$C_3$)fluoroalkyl and halogen); or
  ($C_5$-$C_7$)cycloalkyl, which is annelated with an optionally mono-, di- or tri-substituted (preferably mono- or di-substituted) phenyl, wherein the substituents are selected from halogen; or
  ($C_5$-$C_7$)cycloalkyl-($C_1$-$C_2$)alkyl, which is in the cycloalkyl part optionally di-substituted with halogen (preferably fluorine) and mono-substituted with aryl or heteroaryl, wherein the aryl or heteroaryl groups are optionally mono- or di-substituted with halogen;
and to the salts (in particular pharmaceutically acceptable salts) of such compounds.

3) A further embodiment of the invention relates to compounds according to embodiment 1), wherein
n represents 1 or 2;
X represents —N— or —N(O)—;
$R^1$ represents hydrogen or fluorine;
$R^2$ represents hydrogen; and
$R^3$ represents
  aryl-methyl, which is in the aryl part di- or tri-substituted, wherein the substituents are independently selected from the group consisting of ($C_1$-$C_4$)alkyl, ($C_2$-$C_4$)alkenyl, ($C_3$-$C_6$)cycloalkyl, ($C_1$-$C_4$)alkoxy, hydroxy-($C_1$-$C_3$)alkyl, hydroxy-($C_2$-$C_3$)alkoxy-($C_1$-$C_2$)alkyl, ($C_1$-$C_2$)alkoxy-($C_1$-$C_2$)alkyl, ($C_1$-$C_3$)fluoroalkyl and halogen (and preferably from methyl, ethyl, cyclopropyl, trifluoromethyl, fluoro, chloro and bromo); or
  cyclopentyl, which is annelated with a mono- or di-substituted phenyl, wherein the substituents are selected from halogen; or
  cyclohexyl-methyl, which is in the cyclohexyl part optionally di-substituted with fluorine and mono-substituted with aryl or heteroaryl, wherein the aryl or heteroaryl groups are optionally mono- or di-substituted with halogen; and to the salts (in particular pharmaceutically acceptable salts) of such compounds.

4) A further embodiment of the invention relates to compounds according to any one of embodiments 1) to 3), wherein
n represents 1; and to the salts (in particular pharmaceutically acceptable salts) of such compounds.

5) A further embodiment of the invention relates to compounds according to any one of embodiments 1) to 3), wherein
n represents 2;
and to the salts (in particular pharmaceutically acceptable salts) of such compounds.

6) A further embodiment of the invention relates to compounds according to any one of embodiments 1) to 5), wherein
X represents —N—;
and to the salts (in particular pharmaceutically acceptable salts) of such compounds.

7) A further embodiment of the invention relates to compounds according to any one of embodiments 1) to 6), wherein
$R^1$ represents hydrogen;
and to the salts (in particular pharmaceutically acceptable salts) of such compounds.

8) A further embodiment of the invention relates to compounds according to any one of embodiments 1) to 6), wherein
$R^1$ represents fluorine;
and to the salts (in particular pharmaceutically acceptable salts) of such compounds.

9) A further embodiment of the invention relates to compounds according to any one of embodiments 1) to 8), wherein
$R^2$ represents hydrogen;
and to the salts (in particular pharmaceutically acceptable salts) of such compounds.

10) A further embodiment of the invention relates to compounds according to any one of embodiments 1), 2) or 4) to 9), wherein
$R^3$ represents
  aryl-($C_1$-$C_2$)alkyl, which is in the aryl part mono-, di- or tri-substituted (preferably di- or tri-substituted), wherein the substituents are independently selected from the group consisting of ($C_1$-$C_4$)alkyl, ($C_2$-$C_4$)alkenyl, ($C_3$-$C_6$)cycloalkyl, ($C_1$-$C_4$)alkoxy, hydroxy-($C_1$-$C_3$)alkyl, hydroxy-($C_2$-$C_3$)alkoxy-($C_1$-$C_2$)alkyl, ($C_1$-$C_2$)alkoxy-($C_1$-$C_2$)alkyl, ($C_1$-$C_3$)fluoroalkyl and halogen; or
  ($C_5$-$C_7$)cycloalkyl, which is annelated with an optionally mono-, di- or tri-substituted (preferably mono- or di-substituted) phenyl, wherein the substituents are selected from halogen; or
  ($C_5$-$C_7$)cycloalkyl-($C_1$-$C_2$)alkyl, which is in the cycloalkyl part optionally di-substituted with halogen (preferably fluorine) and mono-substituted with aryl or heteroaryl, wherein the aryl or heteroaryl groups are optionally mono- or di-substituted with halogen;
and to the salts (in particular pharmaceutically acceptable salts) of such compounds.

11) A further embodiment of the invention relates to compounds according to any one of embodiments 1), 2) or 4) to 9), wherein $R^3$ represents
- $(C_5-C_7)$cycloalkyl, which is annelated with an optionally mono-, di- or tri-substituted (preferably mono- or di-substituted) phenyl, wherein the substituents are selected from halogen; or
- $(C_5-C_7)$cycloalkyl-$(C_1-C_2)$alkyl, which is in the cycloalkyl part optionally di-substituted with halogen (preferably fluorine) and mono-substituted with aryl or heteroaryl, wherein the aryl or heteroaryl groups are optionally mono- or di-substituted with halogen;

and to the salts (in particular pharmaceutically acceptable salts) of such compounds.

12) A further embodiment of the invention relates to compounds according to any one of embodiments 1) to 9), wherein
$R^3$ represents
- aryl-methyl, which is in the aryl part di- or tri-substituted, wherein the substituents are independently selected from the group consisting of $(C_1-C_4)$alkyl, $(C_2-C_4)$alkenyl, $(C_3-C_6)$cycloalkyl, $(C_1-C_4)$alkoxy, hydroxy-$(C_1-C_3)$alkyl, hydroxy-$(C_2-C_3)$alkoxy-$(C_1-C_2)$alkyl, $(C_1-C_2)$alkoxy-$(C_1-C_2)$alkyl, $(C_1-C_3)$fluoroalkyl and halogen (and preferably from methyl, ethyl, cyclopropyl, trifluoromethyl, fluoro, chloro and bromo); or
- cyclopentyl, which is annelated with an mono- or di-substituted phenyl, wherein the substituents are selected from halogen; or
- cyclohexyl-methyl, which is in the cyclohexyl part optionally di-substituted with fluorine and mono-substituted with aryl or heteroaryl, wherein the aryl or heteroaryl groups are optionally mono- or di-substituted with halogen;

and to the salts (in particular pharmaceutically acceptable salts) of such compounds.

13) A further embodiment of the invention relates to compounds according to any one of embodiments 1) to 9), wherein
$R^3$ represents
- cyclopentyl, which is annelated with an mono- or di-substituted phenyl, wherein the substituents are selected from halogen; or
- cyclohexyl-methyl, which is in the cyclohexyl part optionally di-substituted with fluorine and mono-substituted with aryl or heteroaryl, wherein the aryl or heteroaryl groups are optionally mono- or di-substituted with halogen;

and to the salts (in particular pharmaceutically acceptable salts) of such compounds.

14) A further embodiment of the invention relates to compounds according to any one of embodiments 1) or 4) to 9), wherein
$R^3$ represents aryl-$(C_1-C_3)$alkyl (preferably aryl-$(C_1-C_2)$ alkyl), which is in the alkyl part optionally mono-substituted with hydroxy or heterocyclyl; and which is in the aryl part mono-, di- or tri-substituted (preferably di- or tri-substituted), wherein the substituents are independently selected from the group consisting of $(C_1-C_4)$alkyl, $(C_2-C_4)$alkenyl, $(C_3-C_6)$cycloalkyl, $(C_1-C_4)$alkoxy, hydroxy-$(C_1-C_3)$alkyl, hydroxy-$(C_2-C_3)$alkoxy, hydroxy-$(C_2-C_3)$alkoxy-$(C_1-C_2)$alkyl, $(C_1-C_2)$alkoxy-$(C_1-C_2)$alkyl, $(C_1-C_3)$fluoroalkyl, $(C_1-C_3)$fluoroalkoxy, cyano, halogen and phenoxy (and preferably from $(C_1-C_4)$alkyl, $(C_2-C_4)$alkenyl, $(C_3-C_6)$cycloalkyl, $(C_1-C_4)$alkoxy, hydroxy-$(C_1-C_3)$alkyl, hydroxy-$(C_2-C_3)$alkoxy-$(C_1-C_2)$alkyl, $(C_1-C_2)$alkoxy-$(C_1-C_2)$alkyl, $(C_1-C_3)$fluoroalkyl and halogen); and to the salts (in particular pharmaceutically acceptable salts) of such compounds.

15) A further embodiment of the invention relates to compounds according to any one of embodiments 1) to 9), wherein
$R^3$ represents aryl-$(C_1-C_2)$alkyl (preferably aryl-methyl), which is in the aryl part di- or tri-substituted, wherein the substituents are independently selected from the group consisting of $(C_1-C_4)$alkyl, $(C_2-C_4)$alkenyl, $(C_3-C_6)$cycloalkyl, $(C_1-C_4)$alkoxy, hydroxy-$(C_1-C_3)$alkyl, hydroxy-$(C_2-C_3)$alkoxy-$(C_1-C_2)$alkyl, $(C_1-C_2)$alkoxy-$(C_1-C_2)$alkyl, $(C_1-C_3)$fluoroalkyl and halogen (and preferably from methyl, ethyl, cyclopropyl, trifluoromethyl, fluoro, chloro and bromo);

and to the salts (in particular pharmaceutically acceptable salts) of such compounds.

16) A further embodiment of the invention relates to compounds according to any one of embodiments 1) or 4) to 9), wherein
$R^3$ represents heteroaryl-$(C_1-C_3)$alkyl, which is in the alkyl part mono-substituted with heterocyclyl; and which is in the heteroaryl part mono-, di- or tri-substituted, wherein the substituents are independently selected from the group consisting of $(C_1-C_4)$alkyl, $(C_3-C_6)$cycloalkyl, $(C_1-C_4)$alkoxy, $(C_1-C_3)$fluoroalkyl and halogen (preferably from $(C_1-C_3)$fluoroalkyl and halogen);

and to the salts (in particular pharmaceutically acceptable salts) of such compounds.

17) A further embodiment of the invention relates to compounds according to any one of embodiments 1), 2) or 4) to 9), wherein
$R^3$ represents heteroaryl-$(C_1-C_2)$alkyl (preferably 2-heteroaryl-ethyl), which is in the alkyl part mono-substituted with heterocyclyl; and which is in the heteroaryl part mono- or di-substituted (preferably mono-substituted), wherein the substituents are independently selected from the group consisting of $(C_1-C_4)$alkyl, $(C_1-C_3)$fluoroalkyl and halogen (preferably from $(C_1-C_3)$fluoroalkyl and halogen);

and to the salts (in particular pharmaceutically acceptable salts) of such compounds.

18) A further embodiment of the invention relates to compounds according to any one of embodiments 1) or 4) to 9), wherein
$R^3$ represents $(C_5-C_7)$cycloalkyl, which is optionally mono-substituted with hydroxy or oxo; and which is annelated with an optionally mono-, di- or tri-substituted phenyl, wherein the substituents are selected from halogen;

and to the salts (in particular pharmaceutically acceptable salts) of such compounds.

19) A further embodiment of the invention relates to compounds according to any one of embodiments 1) to 9), wherein
$R^3$ represents $(C_5-C_6)$cycloalkyl (preferably cyclopentyl), which is annelated with an mono- or di-substituted phenyl, wherein the substituents are selected from halogen;

and to the salts (in particular pharmaceutically acceptable salts) of such compounds.

20) A further embodiment of the invention relates to compounds according to any one of embodiments 1) or 4) to 9), wherein
$R^3$ represents $(C_3-C_7)$cycloalkyl-$(C_1-C_3)$alkyl, which is in the alkyl part optionally mono-substituted with hydroxy; and which is in the cycloalkyl part optionally di-substituted with halogen and optionally mono-substituted with hydroxy, aryl or heteroaryl, wherein the aryl or heteroaryl groups are optionally mono-, di- or tri-substituted with halogen;

and to the salts (in particular pharmaceutically acceptable salts) of such compounds.

21) A further embodiment of the invention relates to compounds according to any one of embodiments 1) to 9), wherein
R³ represents (C₅-C₇)cycloalkyl-(C₁-C₂)alkyl (preferably cyclohexyl-methyl), which is in the cycloalkyl part optionally di-substituted with fluorine and mono-substituted with aryl or heteroaryl, wherein the aryl or heteroaryl groups are optionally mono- or di-substituted with halogen;
and to the salts (in particular pharmaceutically acceptable salts) of such compounds.

22) A further embodiment of the invention relates to compounds according to any one of embodiments 1) to 21), wherein the absolute configuration of the stereogenic center is as depicted in formula ($I_{St1}$)

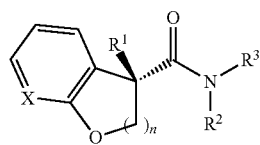

($I_{St1}$)

and to the salts (in particular pharmaceutically acceptable salts) of such compounds.

23) A further embodiment of the invention relates to compounds according to any one of embodiments 1) to 21), wherein the absolute configuration of the stereogenic center is as depicted in formula ($I_{St2}$)

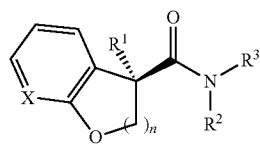

($I_{St2}$)

and to the salts (in particular pharmaceutically acceptable salts) of such compounds.

24) Preferred compounds of formula (I) as defined in embodiment 1) are selected from the group consisting of:
(S)-2,3-Dihydro-furo[2,3-b]pyridine-3-carboxylic acid ((S)-1-cyclohexyl-2-hydroxy-ethyl)-amide;
(R)-2,3-Dihydro-furo[2,3-b]pyridine-3-carboxylic acid ((S)-1-cyclohexyl-2-hydroxy-ethyl)-amide;
(S)-2,3-Dihydro-furo[2,3-b]pyridine-3-carboxylic acid 2,4-dichloro-6-methyl-benzylamide;
(R)-2,3-Dihydro-furo[2,3-b]pyridine-3-carboxylic acid 2,4-dichloro-6-methyl-benzylamide;
2,3-Dihydro-furo[2,3-b]pyridine-3-carboxylic acid 2,4-dichloro-benzylamide;
(S)-2,3-Dihydro-furo[2,3-b]pyridine-3-carboxylic acid [(S)-1-(2,4-dichloro-phenyl)-2-hydroxy-ethyl]-amide;
(R)-2,3-Dihydro-furo[2,3-b]pyridine-3-carboxylic acid [(S)-1-(2,4-dichloro-phenyl)-2-hydroxy-ethyl]-amide;
3,4-Dihydro-2H-pyrano[2,3-b]pyridine-4-carboxylic acid ((S)-1-cyclohexyl-2-hydroxy-ethyl)-amide;
3,4-Dihydro-2H-pyrano[2,3-b]pyridine-4-carboxylic acid [(S)-1-(2,4-dichloro-phenyl)-2-hydroxy-ethyl]-amide;
3,4-Dihydro-2H-pyrano[2,3-b]pyridine-4-carboxylic acid (1-hydroxy-cyclohexylmethyl)-amide;
3-Fluoro-2,3-dihydro-furo[2,3-b]pyridine-3-carboxylic acid 2,4-dichloro-6-methyl-benzylamide;
4-Fluoro-3,4-dihydro-2H-pyrano[2,3-b]pyridine-4-carboxylic acid 2,4-dichloro-6-methyl-benzylamide;
(S*)-2,3-Dihydro-furo[2,3-b]pyridine-3-carboxylic acid ((S*)-1-cyclohepty1-2-hydroxy-ethyl)-amide;
(S*)-2,3-Dihydro-furo[2,3-b]pyridine-3-carboxylic acid ((R*)-1-cyclohepty1-2-hydroxy-ethyl)-amide;
2,3-Dihydro-furo[2,3-b]pyridine-3-carboxylic acid 2,4-dichloro-6-fluoro-benzylamide;
2,3-Dihydro-furo[2,3-b]pyridine-3-carboxylic acid 2-chloro-3-trifluoromethyl-benzylamide;
(S)-3,4-Dihydro-2H-pyrano[2,3-b]pyridine-4-carboxylic acid 2,4-dichloro-6-methyl-benzylamide;
(R)-3,4-Dihydro-2H-pyrano[2,3-b]pyridine-4-carboxylic acid 2,4-dichloro-6-methyl-benzylamide;
3,4-Dihydro-2H-pyrano[2,3-b]pyridine-4-carboxylic acid [1-(6-chloro-pyridin-3-yl)-cyclohexylmethyl]-amide;
3-Fluoro-2,3-dihydro-furo[2,3-b]pyridine-3-carboxylic acid 2,3-dichloro-benzylamide;
2,3-Dihydro-furo[2,3-b]pyridine-3-carboxylic acid 2,4-dichloro-6-cyclopropyl-benzylamide;
2,3-Dihydro-furo[2,3-b]pyridine-3-carboxylic acid 2,4-dichloro-6-ethyl-benzylamide;
2,3-Dihydro-furo[2,3-b]pyridine-3-carboxylic acid 2,4-dichloro-6-vinyl-benzylamide;
(S)-2,3-Dihydro-furo[2,3-b]pyridine-3-carboxylic acid 2,4-dichloro-6-hydroxymethyl-benzylamide;
(R)-2,3-Dihydro-furo[2,3-b]pyridine-3-carboxylic acid 2,4-dichloro-6-hydroxymethyl-benzylamide;
2,3-Dihydro-furo[2,3-b]pyridine-3-carboxylic acid 2,4-dichloro-6-methoxy-benzylamide;
(S*)-2,3-Dihydro-furo[2,3-b]pyridine-3-carboxylic acid [(S*)-2-(4,4-difluoro-piperidin-1-yl)-2-(2-methyl-pyrimidin-5-yl)-ethyl]amide;
(S*)-2,3-Dihydro-furo[2,3-b]pyridine-3-carboxylic acid [(R*)-2-(4,4-difluoro-piperidin-1-yl)-2-(2-methyl-pyrimidin-5-yl)-ethyl]-amide;
(S*)-2,3-Dihydro-furo[2,3-b]pyridine-3-carboxylic acid [(S*)-2-(2-methyl-pyrimidin-5-yl)-2-morpholin-4-yl-ethyl]-amide;
(S*)-2,3-Dihydro-furo[2,3-b]pyridine-3-carboxylic acid [(R*)-2-(2-methyl-pyrimidin-5-yl)-2-morpholin-4-yl-ethyl]-amide;
3,4-Dihydro-2H-pyrano[2,3-b]pyridine-4-carboxylic acid 3-chloro-2-methyl-benzylamide;
3,4-Dihydro-2H-pyrano[2,3-b]pyridine-4-carboxylic acid 2-chloro-4-fluoro-benzylamide;
3,4-Dihydro-2H-pyrano[2,3-b]pyridine-4-carboxylic acid 4-phenoxy-benzylamide;
3,4-Dihydro-2H-pyrano[2,3-b]pyridine-4-carboxylic acid 2,3-dichloro-benzylamide;
3,4-Dihydro-2H-pyrano[2,3-b]pyridine-4-carboxylic acid 4-chloro-benzylamide;
3,4-Dihydro-2H-pyrano[2,3-b]pyridine-4-carboxylic acid 4-trifluoromethyl-benzylamide;
3,4-Dihydro-2H-pyrano[2,3-b]pyridine-4-carboxylic acid (4-chloro-benzyl)-methyl-amide;
3,4-Dihydro-2H-pyrano[2,3-b]pyridine-4-carboxylic acid [2-(2,4-dichloro-phenyl)-ethyl]-amide;
3,4-Dihydro-2H-pyrano[2,3-b]pyridine-4-carboxylic acid 2,4-dichloro-benzylamide;
3,4-Dihydro-2H-pyrano[2,3-b]pyridine-4-carboxylic acid 2-chloro-3-trifluoromethyl-benzylamide;
8-Oxy-3,4-dihydro-2H-pyrano[2,3-b]pyridine-4-carboxylic acid 2,4-dichloro-6-methyl-benzylamide;
2,3-Dihydro-furo[2,3-b]pyridine-3-carboxylic acid 3-chloro-2-methyl-benzylamide;

2,3-Dihydro-furo[2,3-b]pyridine-3-carboxylic acid 2-chloro-4-fluoro-benzylamide;
2,3-Dihydro-furo[2,3-b]pyridine-3-carboxylic acid 4-phenoxy-benzylamide;
2,3-Dihydro-furo[2,3-b]pyridine-3-carboxylic acid 2,3-dichloro-benzylamide;
2,3-Dihydro-furo[2,3-b]pyridine-3-carboxylic acid 4-chloro-benzylamide;
2,3-Dihydro-furo[2,3-b]pyridine-3-carboxylic acid 4-trifluoromethyl-benzylamide;
2,3-Dihydro-furo[2,3-b]pyridine-3-carboxylic acid (4-chloro-benzyl)-methyl-amide;
2,3-Dihydro-furo[2,3-b]pyridine-3-carboxylic acid [2-(2,4-dichloro-phenyl)ethyl]-amide;
2,3-Dihydro-furo[2,3-b]pyridine-3-carboxylic acid 2,4-dichloro-6-(2-hydroxy-ethoxy)-benzylamide;
3,4-Dihydro-2H-pyrano[2,3-b]pyridine-4-carboxylic acid 2,4-dichloro-6-hydroxymethyl-benzylamide;
3,4-Dihydro-2H-pyrano[2,3-b]pyridine-4-carboxylic acid (1-cycloheptyl-2-hydroxy-ethyl)-amide;
3,4-Dihydro-2H-pyrano[2,3-b]pyridine-4-carboxylic acid 3-fluoro-4-trifluoromethoxy-benzylamide;
3,4-Dihydro-2H-pyrano[2,3-b]pyridine-4-carboxylic acid (1-phenyl-cyclohexylmethyl)-amide;
3-Fluoro-2,3-dihydro-furo[2,3-b]pyridine-3-carboxylic acid 2-chloro-3-trifluoromethyl-benzylamide;
2,3-Dihydro-furo[2,3-b]pyridine-3-carboxylic acid 2-chloro-3-cyano-benzylamide;
2,3-Dihydro-furo[2,3-b]pyridine-3-carboxylic acid 3-fluoro-4-trifluoromethoxy-benzylamide;
3,4-Dihydro-2H-pyrano[2,3-b]pyridine-4-carboxylic acid [1-(2,4-dichloro-phenyl)-cyclopropyl]-amide;
(S*)-2,3-Dihydro-furo[2,3-b]pyridine-3-carboxylic acid [(S*)-2-morpholin-4-yl-2-(2-trifluoromethyl-pyrimidin-5-yl)-ethyl]-amide;
(S*)-2,3-Dihydro-furo[2,3-b]pyridine-3-carboxylic acid [(R*)-2-morpholin-4-yl-2-(2-trifluoromethyl-pyrimidin-5-yl)-ethyl]-amide;
2,3-Dihydro-furo[2,3-b]pyridine-3-carboxylic acid 2-chloro-4-cyano-benzylamide;
2,3-Dihydro-furo[2,3-b]pyridine-3-carboxylic acid [2-(4,4-difluoro-piperidin-1-yl)-2-(2-trifluoromethyl-pyrimidin-5-yl)-ethyl]-amide;
2,3-Dihydro-furo[2,3-b]pyridine-3-carboxylic acid (1-carbamoyl-cyclopentyl)-amide;
2,3-Dihydro-furo[2,3-b]pyridine-3-carboxylic acid (2-phenyl-cyclopropyl)-amide;
2,3-Dihydro-furo[2,3-b]pyridine-3-carboxylic acid ((1S,2R)-2-hydroxy-indan-1-yl)-amide;
2,3-Dihydro-furo[2,3-b]pyridine-3-carboxylic acid (2-carbamoyl-cyclohexyl)-amide;
3,4-Dihydro-2H-pyrano[2,3-b]pyridine-4-carboxylic acid (1-(6-chloropyridin-3-yl)-4,4-difluorocyclohexylmethyl)-amide;
2,3-Dihydro-furo[2,3-b]pyridine-3-carboxylic acid 2,4-dichloro-6-trifluoromethyl-benzylamide;
2,3-Dihydro-furo[2,3-b]pyridine-3-carboxylic acid (R)-indan-1-ylamide;
(S)-2,3-Dihydro-furo[2,3-b]pyridine-3-carboxylic acid [(R)-1-(2,4-dichloro-phenyl)-ethyl]-amide;
(R)-2,3-Dihydro-furo[2,3-b]pyridine-3-carboxylic acid [(R)-1-(2,4-dichloro-phenyl)-ethyl]-amide;
2,3-Dihydro-furo[2,3-b]pyridine-3-carboxylic acid 2,4-dichloro-6-methoxymethyl-benzylamide;
2,3-Dihydro-furo[2,3-b]pyridine-3-carboxylic acid 3-chloro-2-trifluoromethyl-benzylamide;
(S*)-2,3-Dihydro-furo[2,3-b]pyridine-3-carboxylic acid [(S*)-2-(6-chloro-pyridin-3-yl)-2-(4,4-difluoro-piperidin-1-yl)-ethyl]amide;
(S*)-2,3-Dihydro-furo[2,3-b]pyridine-3-carboxylic acid [(R*)-2-(6-chloro-pyridin-3-yl)-2-(4,4-difluoro-piperidin-1-yl)-ethyl]-amide;
(S*)-2,3-Dihydro-furo[2,3-b]pyridine-3-carboxylic acid ((S*)-5,7-dichloro-indan-1-yl)-amide;
(S*)-2,3-Dihydro-furo[2,3-b]pyridine-3-carboxylic acid ((R*)-5,7-dichloro-indan-1-yl)-amide;
2,3-Dihydro-furo[2,3-b]pyridine-3-carboxylic acid [2-(4,4-difluoro-piperidin-1-yl)-2-(4-trifluoromethyl-phenyl)-ethyl]-amide;
(S)-2,3-Dihydro-furo[2,3-b]pyridine-3-carboxylic acid 2-bromo-4,6-dichloro-benzylamide;
(R)-2,3-Dihydro-furo[2,3-b]pyridine-3-carboxylic acid 2-bromo-4,6-dichloro-benzylamide;
(S)-2,3-Dihydro-furo[2,3-b]pyridine-3-carboxylic acid [(S)-2-morpholin-4-yl-2-(2-trifluoromethyl-pyrimidin-5-yl)-ethyl]amide;
(S)-2,3-Dihydro-furo[2,3-b]pyridine-3-carboxylic acid [(R)-2-morpholin-4-yl-2-(2-trifluoromethyl-pyrimidin-5-yl)-ethyl]-amide;
(R)-2,3-Dihydro-furo[2,3-b]pyridine-3-carboxylic acid [(S)-2-morpholin-4-yl-2-(2-trifluoromethyl-pyrimidin-5-yl)-ethyl]-amide;
(R)-2,3-Dihydro-furo[2,3-b]pyridine-3-carboxylic acid [(R)-2-morpholin-4-yl-2-(2-trifluoromethyl-pyrimidin-5-yl)-ethyl]-amide;
2,3-Dihydro-furo[2,3-b]pyridine-3-carboxylic acid [2-(6-methoxy-pyridin-3-yl)-2-morpholin-4-yl-ethyl]-amide;
(S*)-2,3-Dihydro-furo[2,3-b]pyridine-3-carboxylic acid ((S*)-3-oxo-indan-1-yl)-amide;
(S*)-2,3-Dihydro-furo[2,3-b]pyridine-3-carboxylic acid ((R*)-3-oxo-indan-1-yl)-amide;
2,3-Dihydro-furo[2,3-b]pyridine-3-carboxylic acid [2-(6-methyl-pyridin-3-yl)-2-morpholin-4-yl-ethyl]-amide;
2,3-Dihydro-furo[2,3-b]pyridine-3-carboxylic acid [2-(2-cyclopropyl-pyrimidin-5-yl)-2-morpholin-4-yl-ethyl]-amide;
2,3-Dihydro-furo[2,3-b]pyridine-3-carboxylic acid [2-morpholin-4-yl-2-(6-trifluoromethyl-pyridin-3-yl)-ethyl]-amide;
2,3-Dihydro-furo[2,3-b]pyridine-3-carboxylic acid 2,4-dichloro-6-(2-hydroxy-ethoxymethyl)-benzylamide;
(S*)-2,3-Dihydro-furo[2,3-b]pyridine-3-carboxylic acid ((S*)-4,6-dichloro-indan-1-yl)-amide; and
(S*)-2,3-Dihydro-furo[2,3-b]pyridine-3-carboxylic acid ((R*)-4,6-dichloro-indan-1-yl)-amide;

or salts (in particular pharmaceutically acceptable salts) of such compounds;

it is to be understood for any of the above listed compounds, that a stereogenic center, which is not specifically assigned, may be in absolute (R)- or absolute (S)-configuration; for example, the stereogenic center at the 3-position of the 2,3-dihydro-furo[2,3-b]pyridine core structure or at the 4-position of the 3,4-dihydro-2H-pyrano[2,3-b]pyridine core structure may be in absolute (R)-configuration or absolute (S)-configuration. For example a compound listed as 3,4-dihydro-2H-pyrano[2,3-b]pyridine-4-carboxylic acid 2-chloro-3-trifluoromethyl-benzylamide may be (S)-3,4-dihydro-2H-pyrano[2,3-b]pyridine-4-carboxylic acid 2-chloro-3-trifluoromethyl-benzylamide, (R)-3,4-dihydro-2H-pyrano[2,3-b]pyridine-4-carboxylic acid 2-chloro-3-trifluoromethyl-benzylamide or any mixture thereof; and a compound listed as 3,4-dihydro-2H-pyrano[2,3-b]pyridine-4-carboxylic acid [(S)-1-(2,4-dichloro-phenyl)-2-hydroxyethyl]-amide may be (S)-3,4-dihydro-2H-pyrano[2,3-b]pyridine-4-carboxylic acid [(S)-1-(2,4-dichloro-phenyl)-2-hydroxy-ethyl]amide, (R)-3,4-dihydro-2H-pyrano[2,3-b]pyridine-4-carboxylic acid [(S)-1-(2,4-dichloro-phenyl)-2-hydroxy-ethyl]-amide or any mixture thereof. Notably, compounds containing more than one stereogenic center may be at each stereogenic center, which is not specifically assigned, in absolute (R)- or absolute (S)-configuration; for example a compound listed as 2,3-dihydro-furo[2,3-b]pyridine-3-carboxylic acid [2-(4,4-difluoro-piperidin-1-yl)-2-(2-trifluoromethyl-pyrimidin-5-yl)-ethyl]-amide may be (S)-2,3-dihydro-furo[2,3-b]pyridine-3-carboxylic acid [(S)-2-(4,4-difluoro-piperidin-1-yl)-2-(2-trifluoromethyl-pyrimidin-5-yl)-ethyl]-amide, (S)-2,3-dihydro-furo[2,3-b]pyridine-3-carboxylic acid [(R)-2-(4,4-difluoro-piperidin-1-yl)-2-(2-trifluoromethyl-pyrimidin-5-yl)-ethyl]-amide, (R)-2,3-dihydro-furo[2,3-b]pyridine-3-carboxylic acid [(S)-2-(4,4-difluoro-piperidin-1-yl)-2-(2-trifluoromethyl-pyrimidin-5-yl)-ethyl]-amide, (R)-2,3-dihydro-furo[2,3-b]pyridine-3-carboxylic acid [(R)-2-(4,4-difluoro-piperidin-1-yl)-2-(2-trifluoromethyl-pyrimidin-5-yl)-ethyl]-amide or any mixture thereof. The assignment of two stereocenters relative to each other is marked by an asterisk; for example a compound listed as (S*)-2,3-dihydro-furo[2,3-b]pyridine-3-carboxylic acid ((S*)-1-cycloheptyl-2-hydroxy-ethyl)-amide may be (S)-2,3-dihydro-furo[2,3-b]pyridine-3-carboxylic acid ((S)-1-cycloheptyl-2-hydroxy-ethyl)-amide, (R)-2,3-dihydro-furo[2,3-b]pyridine-3-carboxylic acid ((R)-1-cycloheptyl-2-hydroxy-ethyl)amide or any mixture thereof.

25) Further preferred compounds of formula (I) as defined in embodiment 1) are selected from the group consisting of:
(S)-2,3-Dihydro-furo[2,3-b]pyridine-3-carboxylic acid 2,4-dichloro-6-trideuteromethyl-benzylamide;
(R)-2,3-Dihydro-furo[2,3-b]pyridine-3-carboxylic acid 2,4-dichloro-6-trideuteromethyl-benzylamide;
(S*)-2,3-Dihydro-furo[2,3-b]pyridine-3-carboxylic acid ((S*)-5-chloro-indan-1-yl)-amide;
(S*)-2,3-Dihydro-furo[2,3-b]pyridine-3-carboxylic acid ((R*)-5-chloro-indan-1-yl)-amide;
(S*)-2,3-Dihydro-furo[2,3-b]pyridine-3-carboxylic acid ((S*)-7-chloro-indan-1-yl)-amide;
(S*)-2,3-Dihydro-furo[2,3-b]pyridine-3-carboxylic acid ((R*)-7-chloro-indan-1-yl)-amide;
2,3-Dihydro-furo[2,3-b]pyridine-3-carboxylic acid 2-chloro-4-trifluoromethyl-benzylamide;
2,3-Dihydro-furo[2,3-b]pyridine-3-carboxylic acid (5,7-dichloro-indan-1-yl)-amide;
2,3-Dihydro-furo[2,3-b]pyridine-3-carboxylic acid [3-(2,4-dichloro-phenyl)-propyl]amide;
(S)-2,3-dihydrofuro[2,3-b]pyridine-3-carboxylic acid ((R)-1,2,3,4-tetrahydronaphthalen-1-yl)-amide;
(R)-2,3-dihydrofuro[2,3-b]pyridine-3-carboxylic acid ((R)-1,2,3,4-tetrahydronaphthalen-1-yl)-amide;
2,3-Dihydro-furo[2,3-b]pyridine-3-carboxylic acid (7-chloro-indan-1-yl)-amide;
(S)-2,3-Dihydro-furo[2,3-b]pyridine-3-carboxylic acid ((R)-8-chloro-1,2,3,4-tetrahydronaphthalen-1-yl)-amide;
(R)-2,3-Dihydro-furo[2,3-b]pyridine-3-carboxylic acid ((R)-8-chloro-1,2,3,4-tetrahydronaphthalen-1-yl)-amide;
2,3-Dihydro-furo[2,3-b]pyridine-3-carboxylic acid (7-bromo-indan-1-yl)-amide;
2,3-Dihydro-furo[2,3-b]pyridine-3-carboxylic acid 2,4,6-trichloro-benzylamide;
7-Oxy-2,3-dihydro-furo[2,3-b]pyridine-3-carboxylic acid 2,4-dichloro-6-methyl-benzylamide;
2,3-Dihydro-furo[2,3-b]pyridine-3-carboxylic acid (5,7-dichloro-1-oxo-indan-2-yl)-amide;
2,3-Dihydro-furo[2,3-b]pyridine-3-carboxylic acid 4-chloro-2-hydroxymethyl-benzylamide; and
2,3-Dihydro-furo[2,3-b]pyridine-3-carboxylic acid 2-chloro-6-hydroxymethyl-benzylamide;
or salts (in particular pharmaceutically acceptable salts) of such compounds;

it is to be understood for any of the above listed compounds, that a stereogenic center, which is not specifically assigned, may be in absolute (R)- or absolute (S)-configuration; for example, the stereogenic center at the 3-position of the 2,3-dihydro-furo[2,3-b]pyridine core structure or at the 4-position of the 3,4-dihydro-2H-pyrano[2,3-b]pyridine core structure may be in absolute (R)-configuration or absolute (S)-configuration. For example a compound listed as 2,3-dihydro-furo[2,3-b]pyridine-3-carboxylic acid 2,4,6-trichloro-benzylamide may be (S)-2,3-dihydro-furo[2,3-b]pyridine-3-carboxylic acid 2,4,6-trichloro-benzylamide, (R)-2,3-dihydro-furo[2,3-b]pyridine-3-carboxylic acid 2,4,6-trichloro-benzylamide or any mixture thereof. Notably, compounds containing more than one stereogenic center may be at each stereogenic center, which is not specifically assigned, in absolute (R)- or absolute (S)-configuration; for example a compound listed as 2,3-dihydro-furo[2,3-b]pyridine-3-carboxylic acid (7-bromo-indan-1-yl)-amide may be (S)-2,3-dihydro-furo[2,3-b]pyridine-3-carboxylic acid ((S)-7-bromo-indan-1-yl)-amide, (S)-2,3-dihydro-furo[2,3-b]pyridine-3-carboxylic acid ((R)-7-bromo-indan-1-yl)-amide, (R)-2,3-dihydro-furo[2,3-b]pyridine-3-carboxylic acid ((S)-7-bromo-indan-1-yl)-amide, (R)-2,3-dihydro-furo[2,3-b]pyridine-3-carboxylic acid ((R)-7-bromo-indan-1-yl)-amide or any mixture thereof. The assignment of two stereocenters relative to each other is marked by an asterisk; for example a compound listed as (S*)-2,3-dihydro-furo[2,3-b]pyridine-3-carboxylic acid ((S*)-5-chloro-indan-1-yl)-amide may be (S)-2,3-dihydro-furo[2,3-b]pyridine-3-carboxylic acid ((S)-5-chloro-indan-1-yl)-amide, (R)-2,3-Dihydro-furo[2,3-b]pyridine-3-carboxylic acid ((R)-5-chloro-indan-1-yl)-amide or any mixture thereof.

It is well understood that the invention relates to compounds according to embodiment 1); or according to embodiment 1) limited by the features of an embodiment dependent on embodiment 1; or according to embodiment 1) limited by the features of a cascade of dependent embodiments e.g. in the form of "embodiment 3) depending on embodiment 2) depending on embodiment 1)". In case of an embodiment depending on more than one other embodiment, it is understood that each combination is specifically disclosed. Also, in case an embodiment is dependent on more than one other embodiment and one or more of said other embodiments are themselves dependent on one or more further embodiments, it is understood that each combination is specifically disclosed if obtainable with regard to the given dependencies and multiple dependencies. Notably, embodiments resulting from cascades of more than three embodiments depending on each other may be construed under observance of the given dependencies and multiple dependencies and are thus intended to be specifically disclosed. Representative examples of embodiments which are possible based on the dependencies of the embodiments 1) to 25) as disclosed hereinabove and which are therefore intended and herewith specifically disclosed in individualized form are:

1, 2+1, 3+1, 4+1, 4+3+1, 5+1, 5+3+1, 6+1, 6+3+1, 7+1, 7+3+1, 8+1, 8+3+1, 9+1, 9+3+1, 9+7+1, 9+7+3+1, 9+8+1, 9+8+3+1, 10+1, 10+7+1, 10+7+3+1, 10+8+1, 10+8+3+1, 10+9+1, 10+9+3+1, 10+9+7+1, 10+9+7+3+1, 10+9+8+1, 10+9+8+3+1, 11+1, 11+7+1, 11+7+3+1, 11+8+1, 11+8+3+1, 11+9+1, 11+9+3+1, 11+9+7+1, 11+9+7+3+1, 11+9+8+1,

11+9+8+3+1, 12+1, 12+3+1, 12+7+1, 12+7+3+1, 12+8+1, 12+8+3+1, 12+9+1, 12+9+3+1, 12+9+7+1, 12+9+7+3+1, 12+9+8+1, 12+9+8+3+1, 13+1, 13+3+1, 13+7+1, 13+7+3+1, 13+8+1, 13+8+3+1, 13+9+1, 13+9+3+1, 13+9+7+1, 13+9+7+3+1, 13+9+8+1, 13+9+8+3+1, 14+1, 14+7+1, 14+7+3+1, 14+8+1, 14+8+3+1, 14+9+1, 14+9+3+1, 14+9+7+1, 14+9+7+3+1, 14+9+8+1, 14+9+8+3+1, 15+1, 15+3+1, 15+7+1, 15+7+3+1, 15+8+1, 15+8+3+1, 15+9+1, 15+9+3+1, 15+9+7+1, 15+9+7+3+1, 15+9+8+1, 15+9+8+3+1, 16+1, 16+7+1, 16+7+3+1, 16+8+1, 16+8+3+1, 16+9+1, 16+9+3+1, 16+9+7+1, 16+9+7+3+1, 16+9+8+1, 16+9+8+3+1, 17+1, 17+7+1, 17+7+3+1, 17+8+1, 17+8+3+1, 17+9+1, 17+9+3+1, 17+9+7+1, 17+9+7+3+1, 17+9+8+1, 17+9+8+3+1, 18+1, 18+7+1, 18+7+3+1, 18+8+1, 18+8+3+1, 18+9+1, 18+9+3+1, 18+9+7+1, 18+9+7+3+1, 18+9+8+1, 18+9+8+3+1, 19+1, 19+3+1, 19+7+1, 19+7+3+1, 19+8+1, 19+8+3+1, 19+9+1, 19+9+3+1, 19+9+7+1, 19+9+7+3+1, 19+9+8+1, 19+9+8+3+1, 20+1, 20+7+1, 20+7+3+1, 20+8+1, 20+8+3+1, 20+9+1, 20+9+3+1, 20+9+7+1, 20+9+7+3+1, 20+9+8+1, 20+9+8+3+1, 21+1, 21+3+1, 21+7+1, 21+7+3+1, 21+8+1, 21+8+3+1, 21+9+1, 21+9+3+1, 21+9+7+1, 21+9+7+3+1, 21+9+8+1, 21+9+8+3+1, 22+1, 22+3+1, 22+7+1, 22+7+3+1, 22+8+1, 22+8+3+1, 22+9+1, 22+9+3+1, 22+9+7+1, 22+9+7+3+1, 22+9+8+1, 22+9+8+3+1, 22+10+1, 22+10+7+1, 22+10+7+3+1, 22+10+8+1, 22+10+8+3+1, 22+10+9+1, 22+10+9+3+1, 22+10+9+7+1, 22+10+9+7+3+1, 22+10+9+8+1, 22+10+9+8+3+1, 22+15+1, 22+15+3+1, 22+15+7+1, 22+15+7+3+1, 22+15+8+1, 22+15+8+3+1, 22+15+9+1, 22+15+9+3+1, 22+15+9+7+1, 22+15+9+7+3+1, 22+15+9+8+1, 22+15+9+8+3+1, 22+17+1, 22+17+7+1, 22+17+7+3+1, 22+17+8+1, 22+17+8+3+1, 22+17+9+1, 22+17+9+3+1, 22+17+9+7+1, 22+17+9+7+3+1, 22+17+9+8+1, 22+17+9+8+3+1, 22+19+1, 22+19+3+1, 22+19+7+1, 22+19+7+3+1, 22+19+8+1, 22+19+8+3+1, 22+19+9+1, 22+19+9+3+1, 22+19+9+7+1, 22+19+9+7+3+1, 22+19+9+8+1, 22+19+9+8+3+1, 22+21+1, 22+21+3+1, 22+21+7+1, 22+21+7+3+1, 22+21+8+1, 22+21+8+3+1, 22+21+9+1, 22+21+9+3+1, 22+21+9+7+1, 22+21+9+7+3+1, 22+21+9+8+1, 22+21+9+8+3+1, 23+1, 23+3+1, 23+7+1, 23+7+3+1, 23+8+1, 23+8+3+1, 23+9+1, 23+9+3+1, 23+9+7+1, 23+9+7+3+1, 23+9+8+1, 23+9+8+3+1, 23+10+1, 23+10+7+1, 23+10+7+3+1, 23+10+8+1, 23+10+8+3+1, 23+10+9+1, 23+10+9+3+1, 23+10+9+7+1, 23+10+9+7+3+1, 23+10+9+8+1, 23+10+9+8+3+1, 23+15+1, 23+15+3+1, 23+15+7+1, 23+15+7+3+1, 23+15+8+1, 23+15+8+3+1, 23+15+9+1, 23+15+9+3+1, 23+15+9+7+1, 23+15+9+7+3+1, 23+15+9+8+1, 23+15+9+8+3+1, 23+17+1, 23+17+7+1, 23+17+7+3+1, 23+17+8+1, 23+17+8+3+1, 23+17+9+1, 23+17+9+3+1, 23+17+9+7+1, 23+17+9+7+3+1, 23+17+9+8+1, 23+17+9+8+3+1, 23+19+1, 23+19+3+1, 23+19+7+1, 23+19+7+3+1, 23+19+8+1, 23+19+8+3+1, 23+19+9+1, 23+19+9+3+1, 23+19+9+7+1, 23+19+9+7+3+1, 23+19+9+8+1, 23+19+9+8+3+1, 23+21+1, 23+21+3+1, 23+21+7+1, 23+21+7+3+1, 23+21+8+1, 23+21+8+3+1, 23+21+9+1, 23+21+9+3+1, 23+21+9+7+1, 23+21+9+7+3+1, 23+21+9+8+1, 23+21+9+8+3+1, 24+1, and 25+1; wherein the list above is not to be construed as limiting with respect to further embodiments which are also possible based on the dependencies of the embodiments 1) to 25) as disclosed hereinabove and which are also intended. In the list above the numbers refer to the embodiments according to their numbering provided hereinabove whereas "+" indicates the dependency from another embodiment. The different individualized embodiments are separated by commas. In other words, "4+3+1" for example refers to embodiment 4) depending on embodiment 3) depending on embodiment 1), i.e. embodiment "4+3+1" corresponds to embodiment 1) further limited by the features of embodiments 3) and 4).

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, pharmaceutical composition, disease or the like.

The compounds of formula (I) according to any one of embodiments 1) to 25), or pharmaceutically acceptable salts thereof, are suitable for use as medicaments. In particular, compounds of formula (I) modulate the P2X$_7$ receptor, i.e. they act as P2X$_7$ receptor antagonists, and are useful for the prevention or treatment of diseases which are associated with the activation of the P2X$_7$ receptor such as pain; neurodegenerative and neuroinflammatory diseases; bone and joint diseases; obstructive diseases of the airways; cardiovascular diseases; eye diseases; skin diseases; abdominal and gastrointestinal tract diseases; genitourinary diseases; cancer; other auto-immune and allergic disorders; and other disorders with an inflammatory or immunological component.

In particular, the compounds of formula (I) according to any one of embodiments 1) to 25), or pharmaceutically acceptable salts thereof, are suitable for the prevention or treatment of pain. Pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain.

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Chronic articular pain conditions include especially rheumatoid arthritis, osteoarthritis, rheumatoid spondylitis, gouty arthritis and juvenile arthritis.

Pain associated with functional bowel disorders includes especially non-ulcer dyspepsia, non-cardiac chest pain and irritable bowel syndrome.

Further, the compounds of formula (I) according to any one of embodiments 1) to 25), or pharmaceutically acceptable salts thereof, are suitable for the prevention or treatment of neurodegenerative and neuroinflammatory diseases. Neurodegenerative and neuro-inflammatory diseases include Alzheimer's disease and other dementing disorders including, but not limited to, Creutzfeldt-Jakob disease (CJD) and new variant Creutzfeldt-Jakob disease (nvCJD); Amyotrophic lateral sclerosis, amyloidosis; multiple sclerosis and other demyelinating syndromes; cerebral atherosclerosis and vasculitis; temporal arteritis; myasthenia gravis; Huntington's disease; Lewy Body dementia; and Parkinson's disease.

Further, the compounds of formula (I) according to any one of embodiments 1) to 25), or pharmaceutically acceptable salts thereof, are suitable for the prevention or treatment of bone and joint diseases. Bone and joint diseases include arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; arthritides associated with or including osteoarthritis/osteoarthrosis, both primary and secondary to, for example, congenital hip dysplasia; cervical and lumbar spondylitis; Still's disease; seronegative spondyloarthropathies including ankylosing spondylitis, psoriatic arthritis, reactive arthritis and undifferentiated spondyloarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Familial Mediterranean fever, Muckle-Wells syndrome, and Familial Hibernian Fever, Kikuchi disease; and drug-induced arthalgias, tendonitis, and myopathies including dystrophies and other inflammatory myopathies.

Further, the compounds of formula (I) according to any one of embodiments 1) to 25), or pharmaceutically acceptable salts thereof, are suitable for the prevention or treatment of obstructive diseases of the airways. Obstructive diseases of the airways include asthma, including bronchial, allergic, intrinsic, and extrinsic asthma, exercise-induced, drug-induced (including aspirin and NSAID-induced) and dust-induced asthma, both intermittent and persistent and of all seventies, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; and acute viral infection including the common cold, and infection due to respiratory syncytial virus, influenza, coronavirus (including SARS) and adenovirus.

Further, the compounds of formula (I) according to any one of embodiments 1) to 25), or pharmaceutically acceptable salts thereof, are suitable for the prevention or treatment of cardiovascular diseases. Cardiovascular diseases include atherosclerosis, affecting the coronary and peripheral circulation; pericarditis; myocarditis; inflammatory and auto-immune cardiomyopathies including myocardial sarcoid; ischaemic reperfusion injuries; endocarditis, valvulitis, and aortitis including infective (for example syphilitic); vasculitides; and disorders of the proximal and peripheral veins including phlebitis and thrombosis, including deep vein thrombosis and complications of varicose veins.

Further, the compounds of formula (I) according to any one of embodiments 1) to 25), or pharmaceutically acceptable salts thereof, are suitable for the prevention or treatment of eye diseases. Eye diseases include blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; and infections of the eyes including viral, fungal, and bacterial infections.

Further, the compounds of formula (I) according to any one of embodiments 1) to 25), or pharmaceutically acceptable salts thereof, are suitable for the prevention or treatment of skin diseases. Skin diseases include psoriasis, skin burn, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; and drug-induced disorders including fixed drug eruptions.

Further, the compounds of formula (I) according to any one of embodiments 1) to 25), or pharmaceutically acceptable salts thereof, are suitable for the prevention or treatment of abdominal and gastrointestinal tract diseases. Abdominal and gastrointestinal tract diseases include hepatitis, including autoimmune, alcoholic and viral hepatitis; fibrosis and cirrhosis of the liver; cholecystitis; pancreatitis, both acute and chronic; non-inflammatory diarrhea; glossitis, gingivitis, periodontitis; oesophagitis, including reflux; eosinophilic gastro-enteritis, mastocytosis, Crohn's disease, colitis including ulcerative colitis, proctitis, pruritis ani; Coeliac disease, irritable bowel disease/syndrome, and food-related allergies which may have effects remote from the gut, for example migraine, rhinitis or eczema; allograft rejection including acute and chronic allograft rejection following, for example, transplantation of kidney, heart, liver, lung, bone marrow, skin or cornea or following blood transfusion; and chronic graft versus host disease;

Further, the compounds of formula (I) according to any one of embodiments 1) to 25), or pharmaceutically acceptable salts thereof, are suitable for the prevention or treatment of genitourinary diseases. Genitourinary diseases include nephritis including interstitial and glomerulonephritis; nephrotic syndrome; cystitis including acute and chronic (interstitial) cystitis and Hunner's ulcer; acute and chronic urethritis, hemorrhagic cystitis, prostatitis, epididymitis, oophoritis and salpingitis; vulvovaginitis; Peyronie's disease; and erectile dysfunction, both male and female.

Further, the compounds of formula (I) according to any one of embodiments 1) to 25), or pharmaceutically acceptable salts thereof, are suitable for the prevention or treatment of cancer. The treatment of cancer includes the treatment of brain tumors, prostate, lung, breast, ovarian, bowel and colon, stomach, pancreatic, skin and bone marrow (including leukaemias) and lymphoproliferative systems, such as non-Hodgkin's and Hodgkin's lymphoma; including the prevention and treatment of metastatic disease and tumor recurrences, and paraneoplastic syndromes.

Further, the compounds of formula (I) according to any one of embodiments 1) to 25), or pharmaceutically acceptable salts thereof, are suitable for the prevention or treatment of other auto-immune and allergic disorders. Other auto-immune and allergic disorders include Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Further, the compounds of formula (I) according to any one of embodiments 1) to 25), or pharmaceutically acceptable salts thereof, are suitable for the prevention or treatment of other disorders with an inflammatory or immunological component. Other disorders with an inflammatory or immunological component include acquired immune deficiency syndrome (AIDS), leprosy, Sezary syndrome, and paraneoplastic syndromes.

Further, the compounds of formula (I) according to any one of embodiments 1) to 25), or pharmaceutically acceptable salts thereof, are suitable for the prevention or treatment of mood, depression, sleep and anxiety disorders.

Further, the compounds of formula (I) according to any one of embodiments 1) to 25), or pharmaceutically acceptable salts thereof, are suitable for the prevention or treatment of injury induced trauma and spinal cord injury.

Especially, compounds of formula (I) according to any one of embodiments 1) to 25), or pharmaceutically acceptable salts thereof, are suitable for the prevention or treatment of diseases selected from one, several or all of the following groups of diseases and disorders:

1) Pain, wherein pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);

Chronic articular pain conditions include especially rheumatoid arthritis, osteoarthritis, rheumatoid spondylitis, gouty arthritis and juvenile arthritis;

Pain associated with functional bowel disorders includes especially non-ulcer dyspepsia, non-cardiac chest pain and irritable bowel syndrome;

2) Neurodegenerative and neuro-inflammatory diseases such as Alzheimer's disease and other dementing disorders including, but not limited to, Creutzfeldt-Jakob disease (CJD) and new variant Creutzfeldt-Jakob disease (nvCJD); amyloidosis; Amyotrophic lateral sclerosis, multiple sclerosis and other demyelinating syndromes; cerebral atherosclerosis and vasculitis; temporal arteritis; myasthenia gravis; Huntington's disease; Lewy Body dementia; and Parkinson's disease;

3) Bone and joint diseases such as arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Muckle-Wells syndrome, and Familial Hibernian Fever, Kikuchi disease; and drug-induced arthalgias, tendonitis, and myopathies;

4) Obstructive diseases of the airways such as chronic obstructive pulmonary disease (COPD); cystic fibrosis;

lung emphysema; sarcoidosis; farmer's lung and related diseases; lung fibrosis, including fibrosis complicating tuberculosis; and chronic cough associated with inflammatory and secretory conditions of the airways;
5) Cardiovascular diseases such as inflammatory and autoimmune cardiomyopathies;
6) Eye diseases such as degenerative or inflammatory disorders affecting the retina;
7) Skin diseases such as psoriasis, skin burn, atopic dermatitis, contact dermatitis or other eczematous dermatoses; and discoid lupus erythematosus;
8) Abdominal and gastrointestinal tract diseases such as fibrosis and cirrhosis of the liver; cholecystitis; pancreatitis, both acute and chronic; Crohn's disease; colitis including ulcerative colitis; and irritable bowel disease/ syndrome;
9) Genitourinary diseases such as nephritis including interstitial and glomerulonephritis; nephrotic syndrome; and cystitis including acute and chronic (interstitial) cystitis; and
10) Other auto-immune and allergic disorders such as Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Most preferably, compounds of formula (I) according to any one of embodiments 1) to 25), or pharmaceutically acceptable salts thereof, are suitable for the prevention or treatment of diseases selected from one, several or all of the following groups of diseases and disorders:
1) Pain, wherein pain refers to acute pain; chronic pain; pain associated with sprains and strains; chronic articular pain; pain associated with rheumatic fever; musculoskeletal pain (preferred); lower back and neck pain; inflammatory pain; neuropathic pain (preferred); visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;
Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);
Chronic articular pain conditions include especially rheumatoid arthritis, osteoarthritis, rheumatoid spondylitis, gouty arthritis and juvenile arthritis; Pain associated with functional bowel disorders includes especially non-ulcer dyspepsia, non-cardiac chest pain and irritable bowel syndrome;
2) Rheumatoid arthritis and osteoarthritis;
3) Chronic obstructive pulmonary disease (COPD); and
4) Crohn's disease.

The invention also relates to the use of a compound of formula (I) according to any one of embodiments 1) to 25) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 25).

A pharmaceutical composition according to the present invention contains at least one compound of formula (I) according to any one of embodiments 1) to 25) (or a pharmaceutically acceptable salt thereof) as the active agent and optionally carriers and/or diluents and/or adjuvants.

The compounds of formula (I) according to any one of embodiments 1) to 25) and their pharmaceutically acceptable salts can be used as medicaments, e.g. in the form of pharmaceutical compositions for enteral (such as especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 25), or a pharmaceutically acceptable salt thereof.

Any reference to a compound of formula (I), ($I_{ST1}$) or ($I_{ST2}$) in this text is to be understood as referring also to the salts (and especially the pharmaceutically acceptable salts) of such compounds, as appropriate and expedient. The preferences indicated for the compounds of formula (I) of course apply mutatis mutandis to the compounds of formula ($I_{ST1}$) and the compounds of formula ($I_{ST2}$) as well as to the salts and pharmaceutically acceptable salts of the compounds of formula (I), of formula ($I_{ST1}$) and of formula ($I_{ST2}$). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (RT) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$, $R^2$, $R^3$, X and n are as defined for formula (I). Other abbreviations used are defined in the experimental section.

In some instances the generic groups $R^1$, $R^2$, $R^3$, X and n might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

PREPARATION OF COMPOUNDS OF FORMULA (I)

Compounds of formula (Ia) can be prepared by reaction of an acid (II) with an amine (III) using standard amide coupling reagents such as HOBt/EDC.HCl, TBTU, $T_3P$ or HATU and a base like DIPEA in a solvent like DCM, THF or DMF preferably at temperatures between RT and 45° C. (scheme 1).

Compounds of formula (Ib) can be prepared by oxidation of compounds of formula (Ia) with a suitable oxidating reagent such as 3-chloroperbenzoic acid in a solvent such as DCM or THF at temperatures between 0° C. and 45° C.

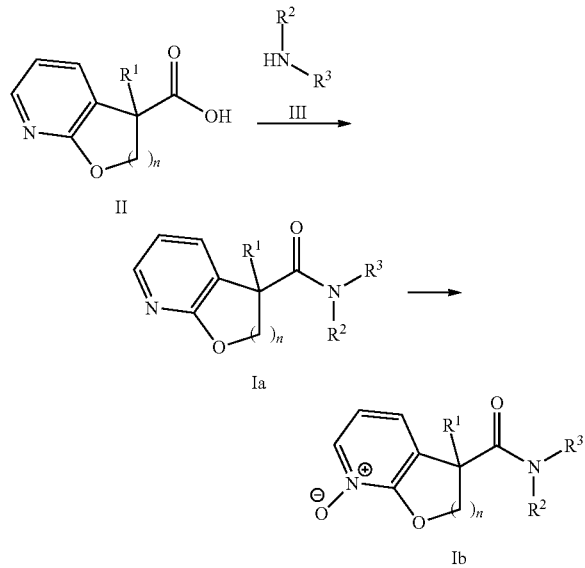

Scheme 1: Synthesis of compounds of formula (I)

Compounds of formula (II) can be prepared as described in the experimental part below.

Compounds of formula (III), if not commercially available, can be prepared following the procedures outlined in the Schemes below.

Compounds of formula (III), wherein $R^2$ represents hydrogen and $R^3$ represents aryl-$(C_2$-$C_3)$alkyl can be prepared from halides (IV), wherein X is preferably bromide or iodide and $R^a$ represents aryl-$(C_1$-$C_2)$alkyl, via a cyanation with NaCN or KCN in a solvent like $CH_3CN$, EtOH or DMF preferably at temperatures between RT and 65° C. The formed nitriles (V) can be reduced by hydrogenation with Raney Nickel as catalyst in a solvent such as $NH_3$ in MeOH. Alternatively, a reducing agent such as $BH_3$ in THF preferably at temperatures between 0° C. and 65° C. or such as $LiAlH_4$ or $Zn(BH_4)_2$ in a solvent like THF or $Et_2O$ preferably at temperatures between 0° C. and 50° C. can be used to form amines (IIIa) (scheme 2). In the same manner, compounds of formula (IIIa), wherein $R^a$ represents aryl, which contain in the aryl part a hydroxy-$(C_1$-$C_3)$alkyl substituent can be prepared form nitriles (V) wherein the aryl part in $R^a$ is substituted with an alkoxy-carbonyl or an alkoxy-carbonyl-$(C_1$-$C_2)$alkyl moiety. In analogy, compounds of formula (III), wherein $R^2$ represents hydrogen and $R^3$ represents aryl-methyl (such as benzyl) can be prepared by reduction of nitriles (V) wherein $R^a$ represents aryl (and notably by reduction with $BH_3$ in THF).

Alternatively, nitriles of formula (V) can be synthesized starting from carboxylic acids of formula (VI), wherein $R^a$ represents aryl-$(C_1$-$C_2)$alkyl or aryl, by preparing the corresponding carboxamides (VII) under standard amide coupling conditions which can be dehydrated using TFAA as dehydrating agent in the presence of $Et_3N$ in a solvent such as DCM preferably at temperatures between 0° C. and RT.

Alternatively, compounds of formula (III), wherein $R^2$ represents hydrogen and $R^3$ represents aryl-$(C_1$-$C_3)$alkyl can be prepared in two steps from aldehydes of formula (VIII), wherein $R^a$ represents aryl-$(C_1$-$C_2)$alkyl or aryl, via formation of the corresponding oximes (IX) using hydroxylamine hydrochloride under standard conditions such as in a solvent like EtOH at temperatures between RT and 60° C. followed by a reduction of the respective oximes using zinc dust in a solvent like acetic acid preferably at temperatures between 0° C. and RT or by using $BH_3$ in a solvent like THF preferably at temperatures between RT and 60° C.

Compounds of formula (IIIb), wherein $R^2$ represents methyl, can be synthesized by a reductive amination reaction of a primary amine of formula (IIIa) using formaldehyde via catalytic hydrogenation in the presence of a suitable catalyst such as $PtO_2$ or Raney Nickel in a solvent like EtOH preferably at temperatures between RT and 45° C. or in the presence of a reducing agent such as $NaBH_4$ or $NaBH(OAc)_3$ in a solvent like MeOH or $ClCH_2CH_2Cl$ at temperatures between RT and 65° C. Alternatively, methylation with MeI in the presence of a base such as NaH in a suitable solvent like THF or DMF at temperatures between 0° C. and RT can be done (scheme 2).

Scheme 2:
Synthesis of compounds of formula (III) wherein $R^3$ represents aryl-$(C_1$-$C_3)$alkyl

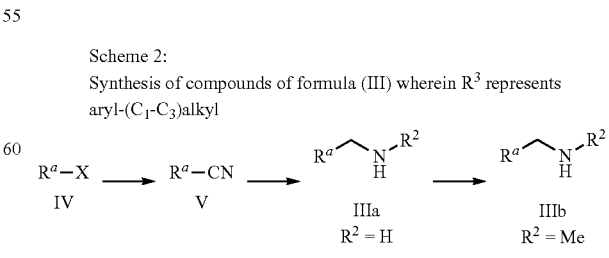

-continued

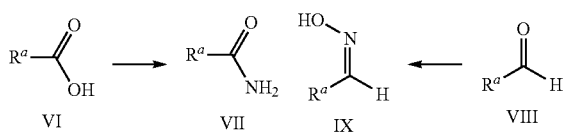

Compounds of formula (X), wherein "aryl" represents an aryl group which is part of $R^3$ representing aryl-$(C_1$-$C_3)$alkyl and wherein $R^b$ is a $(C_1$-$C_4)$alkyl, $(C_3$-$C_6)$cycloalkyl, $(C_1$-$C_4)$ alkoxy, hydroxy-$(C_2$-$C_3)$alkoxy, hydroxymethyl, $(C_1$-$C_2)$ alkoxymethyl or hydroxy-$(C_2$-$C_3)$-alkoxymethyl substituent can be prepared following the procedures outlined in scheme 3.

Compounds of formula (X), wherein "aryl" represents an aryl group which is part of $R^3$ representing aryl-$(C_1$-$C_3)$alkyl and wherein $R^b$ is a $(C_1$-$C_4)$alkyl or a $(C_3$-$C_6)$cycloalkyl substituent can be prepared from compounds of formula (XI) wherein X is a halogen atom (preferably bromide), by a Suzuki type coupling reaction. The Suzuki reaction can be carried out for instance with $(C_1$-$C_4)$alkylboronic acid derivatives or $(C_3$-$C_6)$cycloalkyl-boronic acid derivatives (e.g. ethylboronic acid) in the presence of a suitable base such $K_3PO_4$ and a palladium catalyst like palladium acetate with triphenylphosphine in a solvent such as toluene or dioxane preferably at temperatures between RT and 100° C.

Compounds of formula (X), wherein "aryl" represents an aryl group which is part of $R^3$ representing aryl-$(C_1$-$C_3)$alkyl and wherein $R^b$ is a $(C_1$-$C_4)$alkoxy or a hydroxy-$(C_2$-$C_3)$ alkoxy substituent, can be prepared from compounds of formula (XII) by an alkylation reaction using a base like $K_2CO_3$ or $Cs_2CO_3$ in a solvent such as DMF in the presence of the appropriate alkylating agent such as $(C_1$-$C_4)$alkyl-L or hydroxy-$(C_2$-$C_3)$alkyl-L, wherein L represents a leaving group such as bromide or iodide (e.g., iodomethane).

Compounds of formula (X), wherein "aryl" represents an aryl group which is part of $R^3$ representing aryl-$(C_1$-$C_3)$alkyl and wherein $R^b$ is a hydroxymethyl, a $(C_1$-$C_2)$alkoxymethyl or a hydroxy-$(C_2$-$C_3)$alkoxymethyl substituent, can be prepared from compounds of formula (XIII) by (1) a Wohl-Ziegler type bromination reaction using standard conditions like NBS in the presence of catalytical amounts of AIBN in a solvent such as chlorobenzene preferably at temperatures between 40° C. and 80° C. and (2) followed by a substitution reaction of the respective benzyl bromide with for instance NaOH, NaOMe, NaOEt or AcO—$(C_2$-$C_3)$alkyl-ONa.

Compounds of formula (X), wherein "aryl" represents an aryl group which is part of $R^3$ representing aryl-$(C_1$-$C_3)$alkyl and wherein $R^b$ is a hydroxyethyl, $(C_1$-$C_2)$alkoxyethyl or hydroxy-$(C_2$-$C_3)$alkoxyethyl substituent, can be prepared from compounds of formula (XI) by (1) a Stille type coupling reaction using for instance ethyl tributylstannylacetate in the presence of a suitable catalyst such dichlorobis(tri-o-tolylphosphine)palladium optionally in combination with zinc bromide in a solvent such as DMF preferably at temperatures between RT and 80° C. and (2) followed by a reduction of the corresponding ester with LiAlH$_4$ in a solvent such as THF preferably at temperatures between 0° C. and RT and optionally (3) followed by an alkylation reaction using a base like $K_2CO_3$ or $Cs_2CO_3$ in a solvent such as DMF in the presence of the appropriate alkylating agent such as $(C_1$-$C_2)$ alkyl-L or hydroxy-$(C_2$-$C_3)$alkyl-L, wherein L represents a leaving group such as bromide or iodide (e.g., iodomethane).

Compounds of formula (X), wherein "aryl" represents an aryl group which is part of $R^3$ representing aryl-$(C_1$-$C_3)$alkyl and wherein $R^b$ is a hydroxypropyl, $(C_1$-$C_2)$alkoxypropyl or hydroxy-$(C_2$-$C_3)$alkoxypropyl substituent, can be prepared from compounds of formula (XI) by (1) a Heck type coupling using for instance methylacrylate in the presence of a base such as $Et_3N$ and a suitable palladium catalyst like tetrakis (triphenylphosphine)palladium in a solvent such as DMF preferably at temperatures between RT and 100° C. and (2) followed by a reduction of the corresponding unsaturated ester with LiAlH$_4$ in a solvent such as THF preferably at temperatures between 0° C. and RT and optionally (3) followed by an alkylation reaction using a base like $K_2CO_3$ or $Cs_2CO_3$ in a solvent such as DMF in the presence of the appropriate alkylating agent such as $(C_1$-$C_2)$alkyl-L or hydroxy-$(C_2$-$C_3)$alkyl-L, wherein L represents a leaving group such as bromide or iodide (e.g., iodomethane).

The starting materials (XI), (XII) or (XIII) for the transformations described in scheme 3 may be nitriles of formula (V), aldehydes of formula (VIII) or amines of formula (IIIa), wherein the amino-function is protected by a protecting group such as a phthalimide group, which group may be cleaved after the respective transformation as described in scheme 3 with, for instance, hydrazine in a solvent like EtOH at a temperature around RT. Preferred starting materials for the transformation of compounds of formula (XI) to compounds of formula (X) are amines of formula (IIIa), wherein the amino-function is protected by a protecting group such as a phthalimide group and wherein $R^a$ represents aryl or aryl-$(C_1$-$C_2)$alkyl. Preferred starting materials for the transformation of compounds of formula (XII) to compounds of formula (X) are aldehydes of formula (VIII), wherein $R^a$ represents aryl. Preferred starting materials for the transformation of compounds of formula (XIII) to compounds of formula (X) are nitriles of formula (V), wherein $R^a$ represents aryl.

Scheme 3: Synthesis of compounds of formula (X)

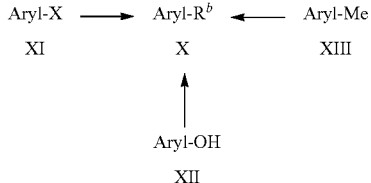

Compounds of formula (III), wherein $R^2$ represents hydrogen and $R^3$ represents an aryl-$(C_1$-$C_3)$alkyl group or a $(C_3$-$C_7)$cycloalkyl-$(C_1$-$C_3)$alkyl group which groups are in the alkyl part mono-substituted with hydroxy can be prepared from amino acid derivatives (XIV), wherein $R^c$ is aryl, arylmethyl or $(C_3$-$C_7)$cycloalkyl and R represents $(C_1$-$C_4)$alkyl (preferably methyl or ethyl), via reduction with LiAlH$_4$ or BH$_3$ in a solvent such as THF or by using NaBH$_4$ in MeOH preferably at temperatures between 0° C. and RT to form the respective aminoalcohols (scheme 4). Compounds of formula (IIId), wherein $R^2$ represents methyl, can be synthesized under the conditions mentioned above.

Scheme 4: Synthesis of compounds of formula (III) wherein R³ represents an aryl-(C₁-C₃)alkyl group or a (C₃-C₇) cycloalkyl-(C₁-C₃)alkyl group which groups are in the alkyl part mono-substituted with hydroxy

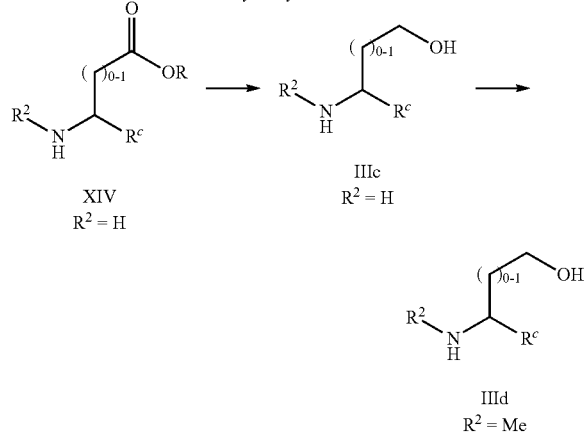

Compounds of formula (III), wherein R² represents hydrogen and R³ represents (C₅-C₇)cycloalkyl, which is annelated with an optionally substituted phenyl can be prepared in two steps from ketones (XV), wherein R represents halogen and m represents 0, 1, 2 or 3 via (1) oxime formation using standard conditions such as O-methylhydroxylamine in a solvent like MeOH optionally in the presence of NaOAc to form compounds of formula (XVI) and (2) a hydrogenation reaction in the presence of a reducing agent such as BH₃ in a solvent like THF preferably at temperatures between RT and 60° C. (scheme 5). Compounds of formula (IIIf), wherein R² represents methyl, can be prepared under the conditions mentioned above.

Scheme 5: Synthesis of compounds of formula (III) wherein R³ represents (C₅-C₇)cycloalkyl, which is annelated with an optionally substituted phenyl

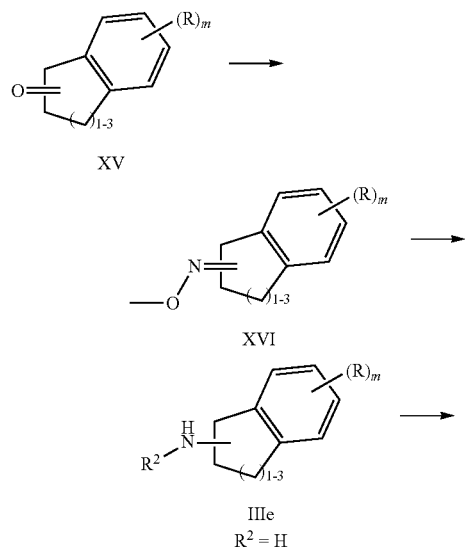

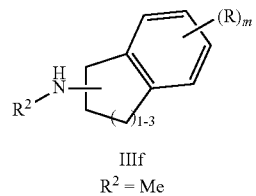

Alternatively, compounds of formula (III), wherein R² represents hydrogen and R³ represents aryl-methyl, can be prepared from aniline derivatives (XVII) by a Meerwein arylation type reaction using a Cu(II) salt like CuCl₂, tBu-nitrite and 1,1-dichloroethylene in a solvent like CH₃CN followed by refluxing in MeOH in the presence of sodium methoxide and subsequent treatment with concentrated H₂SO₄, preferably at a temperature between RT and 90° C. Hydrolysis of the obtained ester derivatives using standard conditions such as NaOH or LiOH in a mixture of water and a suitable organic solvent such as MeOH, EtOH or THF gives the corresponding compounds of formula (XVIII). A Curtius rearrangement using DPPA in a suitable solvent like toluene preferably at temperatures around 100° C. followed by treatment with water or potassium trimethylsilanolate at temperatures around 0° C. leads to compounds of formula (IIIg), wherein R² is hydrogen (scheme 6). Compounds of formula (IIIh), wherein R² represents methyl and R³ represents aryl-methyl, can be prepared under the methylation conditions mentioned above.

Scheme 6: Synthesis of compounds of formula (II) wherein R³ represents aryl-methyl

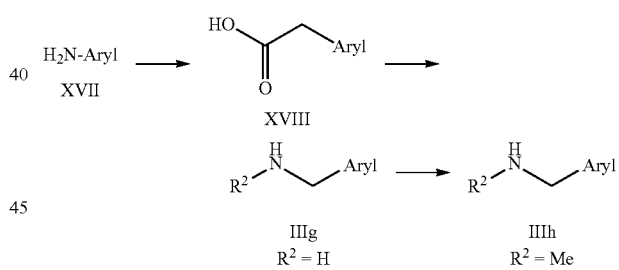

Compounds of formula (III), wherein R² represents hydrogen and R³ represents an aryl-(C₁-C₃)alkyl group or a heteroaryl-(C₁-C₃)alkyl group which groups are in the alkyl part mono-substituted with heterocyclyl, can be prepared in analogy to the methods described in WO2009/132000 or following the procedures outlined in scheme 7 below.

Compounds of formula (XX), wherein Y represents O or CF₂, can be prepared from aldehydes (XIX), wherein R^d represents aryl or heteroaryl, by a Strecker condensation with the respective heterocyclyl group in the presence of TMSCN in a solvent such as DCM or CH₃CN, preferably at temperatures between 0° C. and RT. Hydrogenation of aminonitriles (XX) in the presence of a catalyst like Raney Nickel in a solvent such as NH₃ in MeOH gives the respective amines (IIIi), wherein Y represents O or CF₂. Compounds of formula (IIIj), wherein R² represents methyl, can be prepared under the conditions mentioned above.

Scheme 7: Synthesis of compounds of formula (III), wherein R³ represents an aryl-(C₁-C₃)alkyl group or a heteroaryl-(C₁-C₃) alkyl group which groups are in the alkyl part mono-substituted with heterocyclyl

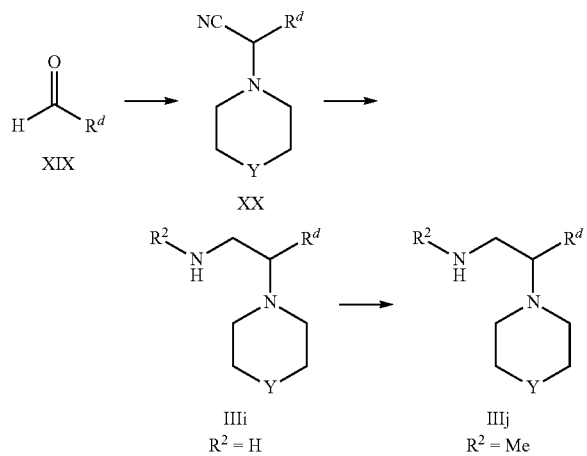

Compounds of formula (III), wherein R² represents hydrogen and R³ represents a (C₃-C₇)cycloalkyl-(C₁-C₃)alkyl group which is in the cycloalkyl part mono-substituted with aryl or heteroaryl can be prepared in analogy to the methods described in WO2009/012482 or following the procedure outlined in Scheme 8 below.

The starting acetonitrile derivatives (XXI), wherein R^e represents aryl or heteroaryl can be alkylated with dihaloalkanes such as 1-bromo-2-chloroethane, 1,3-dibromopropane, 1,4-dibromobutane or 1,5-dibromopentane in the presence of a base like NaH or tBuOK in a suitable organic solvent such as THF or DMSO preferably at temperatures between 0° C. and RT to form the respective compounds of formula (XXII). Reduction of nitriles (XXII) can be carried out by hydrogenation with Raney Nickel as catalyst in a solvent such as NH₃ in MeOH. Alternatively, a reducing agent such as BH₃ in THF can be used preferably at temperatures between RT and 65° C. (scheme 8). Compounds of formula (IIIm) wherein R² represents methyl can be prepared under the conditions mentioned above.

Scheme 8: Synthesis of compounds of formula (III) wherein R³ represents a (C₃-C₇)cycloalkyl-methyl group which is in the cycloakyl part mono-substituted with aryl or heteroaryl

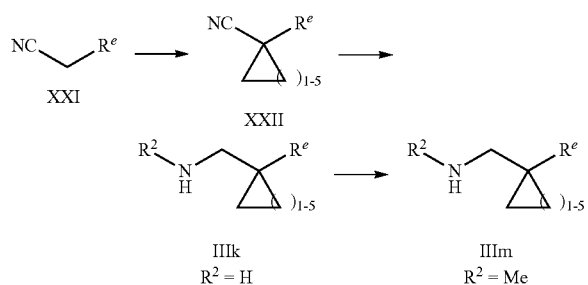

Compounds of formula (III), wherein R² represents hydrogen and R³ represents a (C₃-C₇)cycloalkyl-methyl group which is in the cycloalkyl part mono-substituted with hydroxy can be prepared via a cyanation of ketones (XXIII) using NaCN or TMSCN in a suitable solvent like acetic acid preferably at temperatures between 0° C. and RT (scheme 9). Reduction of cyanohydrines (XXIV) can be carried out as described above for compounds of formula (XXII). Compounds of formula (IIIo), wherein R² represents methyl, can be prepared under the conditions mentioned above.

Scheme 9: Synthesis of compounds of formula (III) wherein R³ represents a (C₃-C₇)cycloalkyl-methyl group which is in the cycloakyl part mono-substituted with hydroxy

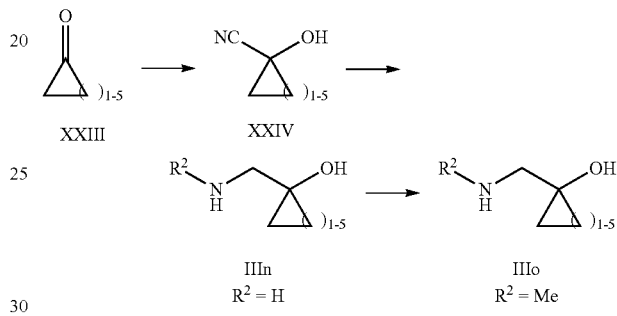

Compounds of formula (III), wherein R² represents hydrogen and R³ represents a cyclohexyl-alkyl group which is in the cyclohexyl part di-substituted with fluoro can be prepared as described in scheme 10. For instance, a tandem double Michael addition-Dieckmann condensation reaction with methylacrylate [J. Org. Chem., 72, 7455-7458 (2007)] of the respective acetonitrile derivative (XXV) followed by a Krapcho decarboxylation under standard conditions using wet DMSO as solvent in the presence of a halide anion (e.g., LiCl) preferably at temperatures between 100° C. and 150° C. and difluorination using DAST in a solvent such as DCM preferably at temperatures between −78° C. and RT gives the respective difluorine compounds of formula (XXVIII) (scheme 10). Reduction of nitriles (XXVIII) can be carried out as described above for compounds of formula (XXII). Compounds of formula (IIIq), wherein R² represents methyl, can be prepared under the conditions mentioned above.

Scheme 10: Synthesis of compounds of formula (III) wherein R³ represents a cyclohexy-alkyl group which is in the cyclohexyl part di-substituted with fluoro

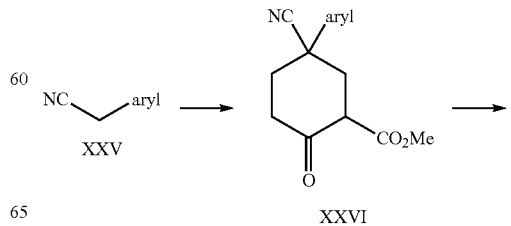

-continued

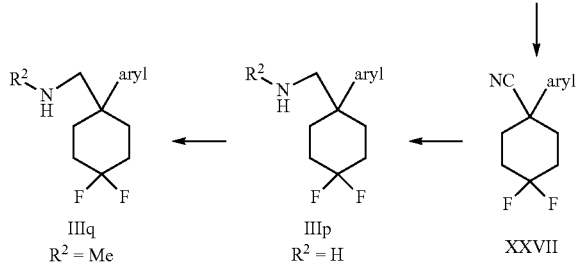

EXPERIMENTAL PART

Abbreviations (as Used Herein and in the Description Above)
Ac acetyl
AIBN azobisisobutyronitrile
anh. anhydrous
aq aqueous
ATP adenosine-5'-triphosphate
CC column chromatography
cDNA complementary desoxyribonucleic acid
CNS central nervous system
DAST diethylaminosulfur trifluoride
DCM dichloromethane
DEA diethylamine
DIPEA diisopropylethylamine
DMAP dimethylaminopyridine
DMEM Dulbecco's modified eagle's medium
DMF dimethylformamide
DMSO dimethylsulfoxide
DNA desoxyribonucleic acid
DPPA diphenylphosphoryl azide
Et ethyl
EDC.HCl N-(3-dimethylaminopropyl)-N'-ethylcarbodiimide hydrochloride
FCS fetal calf serum
FLIPR fluorescent imaging plate reader
h hour(s)
HATU 2-(7-azabenzotriazol-1-yl)-1,1,3,3-tetramethyluronium hexafluorophosphate
Hept heptanes
HMDA hexamethyldisilazide
HOAT 1-hydroxy-7-azabenzotriazole
HOBT 1-hydroxybenzotriazole hydrate
HV high vacuum
ID inner diameter
LC-MS liquid chromatography-mass spectrometry
LDA lithium diisopropylamide
M molar
Me methyl
min minute(s)
MTBE methyl tert.-butyl ether
N normal
NBS N-bromosuccinimide
NFSI N-fluorobenzenesulfonimide
NMR nuclear magnetic resonance
PBS phosphate buffered saline
PG protecting group
Rf retention factor
RNA ribonucleic acid
RT room temperature
sat. saturated
TBTU O-(benzotriazol-1-yl)-N,N,N',N'-tetramethyluronium tetrafluoroborate
tBu tert.-butyl
TFA trifluoroacetic acid
TFFA trifluoroacetic anhydride
THF tetrahydrofuran
TLC thin layer chromatography
TMS trimethylsilyl
$T_3P$ propylphosphonic anhydride
$t_R$ retention time
UV ultra-violet
V is visible
Characterization Methods Used
  NMR: Brucker Avance 400, 400 MHz; chemical shifts are given in ppm relative to the solvent used; multiplicities: s=singlet, d=doublet, t=triplet, q=quadruplet, m=multiplet, br=broad, coupling constants are given in Hz.
  LC-MS: Thermo Finnigan MSQ Surveyor MS with Agilent 1100 Binary Pump and DAD. Conditions: eluents: A: $H_2O$+0.04% TFA; B: $CH_3CN$; gradient: 5% B→95% B; runtime: 1.5 min; flow: 4.5 mL/min; detection: UV/Vis+MS, $t_R$ is given in min.
  LC-MS (A): column Waters XBridge C18, 2.5 µm, 4.6×30 mm
  LC-MS (B): column Waters Atlantis T3, 5 µm, 4.6×30 mm
  LC-MS (C): column Zorbax SB-aq, 3.5 µm, 4.6×50 mm
  Conditions: LC-MS (D): eluents: A: $H_2O$+13 mmol/L $NH_4OH$; B: $CH_3CN$; gradient: 5% B→95% B; runtime: 1.5 min; flow: 4.5 mL/min; detection: UV/Vis+MS, $t_R$ is given in min; column Waters XBridge C18, 2.5 µm, 4.6×50 mm. LC-MS: Waters Acquity UPLC (ACQ-CM, -ACQ-BSM-ACD-SM)
  Conditions: LC-MS (E): eluents: A: $H_2O$+0.05% v/v formic acid; B: $CH_3CN$+0.045% v/v formic acid; gradient: 2% B→98% B; runtime: 2 min; flow: 1.2 mL/min; detection: UV 214 nm+ELSD and MS; column Acquity UPLC CSH C18 1.7 µm, 2.1×50 mm.
  Conditions: LC-MS (F): eluents: A: $H_2O$+0.05% v/v TFA; B: $CH_3CN$+0.045% v/v TFA; gradient: 2% B→98% B; runtime: 2 min; flow: 1.2 mL/min; detection: UV 214 nm+ELSD and MS; column Acquity UPLC CSH C18 1.7 µm, 2.1×50 mm.
  TLC: silica gel 60 $F_{254}$ Merck, 0.25 mm layer thickness
Purification Methods Used
  Column chromatography (CC) (G) was performed using silica gel 60 Merck (0.063-0.200 mm) or using prepacked cartridges (SNAP KP-SIL™, SNAP KP-NH™, Isolute™) from Biotage.
  Preparative LC-MS (normal phase): flow: 40 mL/min. Detection: UV-Vis and/or MS.
  Column: Macherey-Nagel Nucleosil SiOH, 10 µM, 21×100 mm
  Eluents: A=Hept, B=EtOAc, C=MeOH

| t (min) | 0 | 0.4 | 0.5 | 6.0 | 6.2 | 7.8 | 7.9 | 8.8 | 8.9 | 9.0 |
|---|---|---|---|---|---|---|---|---|---|---|
| | | | | Conditions (H): | | | | | | |
| % A | 90 | 90 | 70 | 40 | 25 | 25 | 0 | 0 | 90 | 90 |
| % B | 10 | 10 | 30 | 55 | 70 | 70 | 30 | 30 | 10 | 10 |
| % C | 0 | 0 | 0 | 5 | 5 | 5 | 70 | 70 | 0 | 0 |

-continued

| t (min) | 0 | 0.4 | 0.5 | 6.0 | 6.2 | 7.8 | 7.9 | 8.8 | 8.9 | 9.0 |
|---|---|---|---|---|---|---|---|---|---|---|
| Conditions (I): | | | | | | | | | | |
| % A | 90 | 90 | 50 | 20 | 10 | 10 | 0 | 0 | 90 | 90 |
| % B | 10 | 10 | 50 | 65 | 70 | 70 | 30 | 30 | 10 | 10 |
| % C | 0 | 0 | 0 | 15 | 20 | 20 | 70 | 70 | 0 | 0 |

Preparative LC-MS (reverse phase): flow: 75 mL/min. Detection: UV-Vis and/or MS.
XBridge: column Waters XBridge C18, 10 μm, 30×75 mm
Acidic: eluent: A=$H_2O$ with 0.5% formic acid, B=$CH_3CN$
Basic: eluent: A=$H_2O$ with 0.125% $NH_4OH$, B=$CH_3CN$
Apolar gradient: 30% B→95% B over 3.5 min then 95% B over 2.5 min
Normal gradient: 20% B→95% B over 4 min then 95% B over 2 min
Polar gradient: 10% B→95% B over 4 min then 95% B over 2 min
Very polar gradient: 5% B→50% B over 3 min then 50% B→95% B over 1 min and finally 95% B over 2 min
Extremely polar gradient: 0% B over 1 min then 0% B→20% B over 2.5 min then 20% B→95% B over 0.5 min and finally 95% B over 2 min

|  | acidic | basic |
|---|---|---|
| apolar gradient | (J) | (K) |
| normal gradient | (L) | (M) |
| polar gradient | (N) | (P) |
| very polar gradient | (Q) | (T) |
| extremly polar gradient | (U) | (V) |

Racemates can be separated into their enantiomeres by preparative chiral HPLC. The respective conditions are described below.
The following examples illustrate the invention but do not at all limit the scope thereof.

A. Preparation of Precursors and Intermediates

A.1 Synthesis of Carboxylic Acid Derivatives (II)

A.1.1 Synthesis of 3-fluoro-2,3-dihydrofuro[2,3-b]pyridine-3-carboxylic acid

A.1.1.1 Synthesis of furo[2,3-b]pyridine-3-carboxylic acid

To a suspension of furo[2,3-b]pyridine-3-carboxaldehyde (67 mmol) [J. Heterocyclic Chem., 23, 1465 (1986)] in 52 mL $H_2O$ were added $NaH_2PO_4$ (67 mmol), 260 mL t-BuOH, 71 mL 2-methyl-2-butene followed by portionwise addition of $NaClO_2$ (100 mmol) at 0° C. After 15 min, the cooling bath was removed and the reaction was stirred at RT for 24 h. A solution of sat. aq. $NaHCO_3$ was added and the mixture was extracted with EtOAc. The water phase was acidified with 1N HCl solution and it was then extracted 3 times with EtOAc. The combined organic layers were dried over $MgSO_4$ and concentrated in vacuo to obtain the desired compound as beige solid.
LC-MS (A): $t_R$=0.41 min; [M+H]+: 164.21.

A.1.1.2 Synthesis of furo[2,3-b]pyridine-3-carboxylic acid methyl ester

To a suspension of furo[2,3-b]pyridine-3-carboxylic acid (53 mmol) in 85 mL DCM were added EDC.HCl (58 mmol), DMAP (16 mmol) and 4.3 mL MeOH. The beige suspension was stirred at RT for 2 h. The reaction mixture was diluted with 50 mL DCM and quenched with sat. aq. $NaHCO_3$ solution. The organic phase was washed 3 times with sat. aq. $NH_4Cl$ solution and once with brine. The organic layer was dried over $MgSO_4$ and concentrated in vacuo to obtain the desired compound as grey solid.
LC-MS (A): $t_R$=0.56 min; [M+H]+: 178.14.

A.1.1.3 Synthesis of 2,3-dihydrofuro[2,3-b]pyridine-3-carboxylic acid methyl ester To a suspension of furo[2,3-b]pyridine-3-carboxylic acid methyl ester (48 mmol) in 180 mL MeOH was added NaOAc (97 mmol). The flask was evacuated and filled three times with argon, 20% wet $Pd(OH)_2$ on carbon (1000 mg) was added and the reaction was stirred for 20 h under a hydrogen atmosphere. It was then filtered over a 2 cm pad of celite and was washed with EtOH (50 mL) and EtOAc (50 mL). The filtrate was concentrated in vacuo to afford the desired compound as colorless oil.
LC-MS (A): $t_R$=0.40 min; [M+H]+: 180.26.

A.1.1.4 Synthesis of 3-fluoro-2,3-dihydrofuro[2,3-b]pyridine-3-carboxylic acid methyl ester To a solution of LiHMDA (1.4 mmol, 1M in THF) in 1 mL THF was added a solution of 2,3-dihydrofuro[2,3-b]pyridine-3-carboxylic acid methyl ester (0.56 mmol) in 1 mL THF at −78° C. After 45 min, NFSI (0.83 mmol), dissolved in 1 mL THF, was dropwise added still at −78° C. The reaction mixture was stirred overnight allowing to warm slowly to RT. The reaction was quenched with sat. aq. $NaHCO_3$ solution and extracted 3 times with EtOAc. The combined organic layers were washed with brine, dried over $MgSO_4$ and concentrated in vacuo. Purification by CC using Hept/EtOAc (⅞ to 3/7) gives the desired product as white solid.
LC-MS (A): $t_R$=0.48 min; [M+H]+: 198.20.

A.1.1.5 Synthesis of 3-fluoro-2,3-dihydrofuro[2,3-b]pyridine-3-carboxylic acid

To a solution of 3-fluoro-2,3-dihydrofuro[2,3-b]pyridine-3-carboxylic acid methyl ester (0.30 mmol) in 3 mL EtOH and 2 mL MeOH was added a solution of $LiOH.H_2O$ (0.33 mmol) in 1 mL $H_2O$. The reaction was stirred at RT for 50 min. The reaction mixture was diluted with 10 mL EtOAc and extracted twice with water. The water phase was acidified to pH 3 and extracted 3 times with EtOAc. The combined organic layers were dried over $MgSO_4$ and concentrated in vacuo to obtain the desired product as white solid.
LC-MS (A): $t_R$=0.20 min; [M+H]+: 184.08.

A.1.2 Synthesis of 2,3-dihydrofuro[2,3-b]pyridine-3-carboxylic acid

To a solution of 2,3-dihydrofuro[2,3-b]pyridine-3-carboxylic acid methyl ester (21.2 mmol) in 20 mL EtOH and 15 mL MeOH was added a solution of $LiOH.H_2O$ (23.3 mmol) in 6 mL $H_2O$. After stirring at RT for 1 h, the reaction mixture was diluted with 20 mL EtOAc and extracted twice with water. The water phase was acidified to pH 3 and extracted 5 times with EtOAc and 3 times with DCM. The combined organic layers were dried over $MgSO_4$ and concentrated in vacuo to obtain the desired product as beige solid.
LC-MS (A): $t_R$=0.25 min; [M+H]+: 166.00.

A.1.3 Synthesis of 3,4-dihydro-2H-pyrano[2,3-b]pyridine-4-carboxylic acid

A.1.3.1 Synthesis of 3-(2-chloropyridin-3-yl)-3-hydroxypropanoic acid ethyl ester To a solution of 14.5 mL diisopropylamine in 336 mL THF was added 49 mL n-BuLi (2.5 M in hexanes) at 0° C. The mixture was stirred at 0° C. for 15 min, cooled to −78° C. before 10 mL EtOAc were dropwise added. After another 30 min, a solution of 2-chloro-3-pyridine carboxaldehyde (84.8 mmol), dissolved in 84 mL THF, was added. The mixture was stirred at −78° C. for 30 min and then allowed to warm to RT. After stirring for 1.5 h, the reaction was quenched with sat. aq. NaHCO$_3$ solution and extracted with EtOAc. The combined organic layers were washed with brine, dried over MgSO$_4$ and concentrated in vacuo. Purification with CC (KP-SIL™ from Biotage) using Hept/EtOAc (10/1) to EtOAc gives the desired compound as yellow oil.

LC-MS (A): $t_R$=0.51 min; [M+H]+: 230.19.

A.1.3.2 Synthesis of 1-(2-chloropyridin-3-yl)propane-1,3-diol

To a solution of 3-(2-chloropyridin-3-yl)-3-hydroxypropanoic acid ethyl ester (66.7 mmol) in 47 mL THF was added a suspension of LiAlH$_4$ (100 mmol) in 219 mL THF at 0° C. The mixture was stirred at 0° C. for 1 h and was then quenched by adding consecutively 3.8 mL water, 3.8 mL 15% aq. NaOH solution and 11.4 mL water. The mixture was filtrated and the residue was washed with MTBE and EtOAc. The filtrate was dried over MgSO$_4$ and concentrated in vacuo to obtain the desired product as yellow solid.

LC-MS (A): $t_R$=0.29 min; [M+H]+: 188.19.

A.1.3.3 Synthesis of 3,4-dihydro-2H-pyrano[2,3-b]pyridin-4-ol

A mixture of 1-(2-chloropyridin-3-yl)propane-1,3-diol (62.9 mmol) and KOtBu (189 mmol) in 240 mL tBuOH (dried over 3 Å molsieves) was heated to 80° C. for 2.5 h. The reaction mixture was then concentrated to about ¼ of its volume, diluted with water and extracted 5 times with DCM. The combined organic layers were washed with brine, dried over MgSO$_4$ and concentrated in vacuo. Purification with CC (KP-SIL™ from Biotage) using MeOH/DCM (99/1 to 95/5) gives the desired compound as orange oil.

LC-MS (A): $t_R$=0.13 min; [M+H]+: 152.21.

A.1.3.4 Synthesis of 4-chloro-3,4-dihydro-2H-pyrano[2,3-b]pyridine

To a mixture of 3,4-dihydro-2H-pyrano[2,3-b]pyridin-4-ol (21 mmol) in 80 mL DCM was added 2.3 mL thionyl chloride at 0° C. The reaction mixture was stirred at 0° C. for 10 min and then at reflux for 30 min. After cooling to RT, sat. aq. NaHCO$_3$ solution was added and the mixture was extracted 3 times with EtOAc. The combined organic layers were washed with brine, dried over MgSO$_4$ and concentrated in vacuo to obtain the desired product as orange oil.

LC-MS (A): $t_R$=0.41 min; [M+H]+: 170.01.

A.1.3.5 Synthesis of 3,4-dihydro-2H-pyrano[2,3-b]pyridine-4-carbonitrile

To a mixture of 4-chloro-3,4-dihydro-2H-pyrano[2,3-b]pyridine (18.7 mmol) in 60 mL DMF was added KCN (56.1 mmol) and the mixture was stirred at 90° C. overnight. After cooling to RT, the mixture was diluted with aq. 0.5 M NaOH solution and extracted 3 times with EtOAc. The combined organic layers were washed again with aq. 0.5 M NaOH solution and once with brine. The organic phase was dried over MgSO$_4$ and concentrated in vacuo. Purification with CC (KP-SIL™ from Biotage) using Hept/EtOAc (4/1) to EtOAc gives the desired compound as yellow oil.

LC-MS (A): $t_R$=0.28 min; [M+H]+: 161.10.

A.1.3.6 Synthesis of 3,4-dihydro-2H-pyrano[2,3-b]pyridine-4-carboxylic acid A solution of 3,4-dihydro-2H-pyrano[2,3-b]pyridine-4-carbonitrile (8.87 mmol) in 17.6 mL aq. 32% HCl solution was stirred at 90° C. for 3 h. The reaction mixture was then concentrated, the remaining solid was suspended in MeOH and filtrated. Evaporation of the solvent gives the desired product as yellow solid.

LC-MS (A): $t_R$=0.15 min; [M+H]+: 180.27.

A.1.4 Synthesis of 4-fluoro-3,4-dihydro-2H-pyrano[2,3-b]pyridine-4-carboxylic acid

A.1.4.1 Synthesis of 4-fluoro-3,4-dihydro-2H-pyrano[2,3-b]pyridine-4-carbonitrile To a solution of 3,4-dihydro-2H-pyrano[2,3-b]pyridine-4-carbonitrile (0.62 mmol) in 4.5 mL THF was added NaHMDA (0.75 mmol, 1 M in THF) at −78° C. After 1 h, a solution of NFSI (0.75 mmol) in 0.5 mL THF was added at −78° C. The mixture was stirred at −78° C. for 30 min, at 0° C. for 2 h and finally at RT overnight. The reaction was quenched with sat. aq. NaHCO$_3$ solution and extracted 3 times with EtOAc. The combined organic layers were washed with brine, dried over Na$_2$SO$_4$ and concentrated in vacuo. Purification with CC (KP-SIL™ from Biotage) using Hept to Hept/EtOAc (4/1) gives the desired compound as colorless solid.

LC-MS (A): $t_R$=0.50 min; [M+H]+: 179.23.

A.1.4.2 Synthesis of 4-fluoro-3,4-dihydro-2H-pyrano[2,3-b]pyridine-4-carboxylic acid A solution of 4-fluoro-3,4-dihydro-2H-pyrano[2,3-b]pyridine-4-carbonitrile (0.09 mmol) in 0.2 mL aq. 32% HCl solution was stirred at 90° C. for 3 h. The reaction mixture was then concentrated and dried at HV to give the desired product as yellow oil.

LC-MS (A): $t_R$=0.15 min; [M+CH$_3$CN+H]+: 239.23.

A.2 Synthesis of Amino Derivatives (III)

A.2.1 Synthesis of 2-amino-2-cycloheptylethanol

A.2.1.1 Synthesis of 2-amino-2-cycloheptylacetic acid tert-butyl ester

To a solution of N-(diphenylmethylene)glycerine tert-butyl ester (6.83 mmol) and (R)-4,4-dibutyl-2,6-bis(3,4,5-trifluorophenyl)-4,5-dihydro-3H-dinaphthol[7,6,1,2-cde]azepinium bromide (6.84 μmol) in 45 mL toluene were sequentially added cycloheptyl bromide (8.2 mmol) and CsOH H$_2$O (34.2 mmol) at −10° C. The reaction mixture was stirred at −10° C. for 10 min and then at RT for 4 days. Another portion of (R)-4,4-dibutyl-2,6-bis(3,4,5-trifluorophenyl)-4,5-dihydro-3H-dinaphthol[7,6,1,2-cde]azepinium bromide (6.84 µmol) was added and stirring was continued at RT for another 24 h. The reaction was quenched with water and extracted 3 times with DCM. The combined organic layers were combined, concentrated and the residue was redissolved in 100 mL THF. A solution of 100 mL aq. 0.5M citric acid solution was added and the mixture was stirred at RT for 4 h. The mixture was concentrated to half of its volume and extracted twice with Et$_2$O. The aqueous layer was basified with solid NaHCO$_3$ and extracted 3 times with DCM. The combined organic layers were dried over MgSO$_4$ and concentrated in vacuo to obtain the desired product as yellow oil.

LC-MS (A): $t_R$=0.61 min; [M+H]+: 228.29.

A.2.1.2 Synthesis of 2-amino-2-cycloheptylethanol

To a solution of 3.43 mL LiAlH$_4$ (1M in THF) in 8 mL THF was added a solution of 2-amino-2-cycloheptylacetic acid tert-butyl ester (1.72 mmol) in 3 mL THF at 0° C. The ice bath was removed and stirring was continued at RT for 1 h. The reaction mixture was cooled to 0° C., quenched with water and a 1M NaOH solution, filtered over a pad of celite and washed with EtOAc. The filtrate was basified with a 1M NaOH solution to pH 8-9 and it was then extracted 3 times with EtOAc. The combined organic layers were dried over MgSO$_4$ and concentrated in vacuo to obtain the crude product as yellow oil. The crude was dissolved in 3 mL Et$_2$O and a solution of 4M HCl in dioxane was dropwise added at 0° C. The resulting precipitate was separated by filtration and dried in vacuo to give the corresponding HCl salt as yellow solid.

LC-MS (A): $t_R$=0.39 min; [M+H]+: 158.14.

A.2.2 Synthesis of 2,4-dichloro-6-fluorobenzylamine

A.2.2.1 Synthesis of 2,4-dichloro-6-fluorobenzonitrile

To a solution of 2,4-dichloro-6-fluorobenzamide (5.07 mmol) (US 20060178386) in 74 mL DCM were added Et$_3$N (15.2 mmol) followed by TFAA (10.1 mmol) at 0° C. After 30 min, water was added, the organic layer was separated and concentrated in vacuo. Purification with CC (KP-SIL™ from Biotage) using Hept/EtOAc (4/1 to 1/3) gives the desired compound as colorless solid.

LC-MS (A): $t_R$=0.80 min; $^1$H NMR ((CD$_3$)$_2$SO) δ: 7.94 (s, 1H), 7.91 (s, 1H).

A.2.2.2 Synthesis of 2,4-dichloro-6-fluorobenzylamine

To a solution of 2,4-dichloro-6-fluorobenzonitrile (3.87 mmol) in 15 mL THF was added a solution of BH$_3$ (15.5 mmol, 1M in THF) and the mixture was stirred at 60° C. for 1 h. After cooling to 0° C., water was added followed by MeOH and the mixture was then heated to 70° C. for 10 min. The solvent was evaporated, the residue was taken up in water and EtOAc. The aqueous phase was separated, basified with 1M NaOH and it was extracted 3 times with EtOAc. The combined organic layers were dried over MgSO$_4$ and concentrated in vacuo to obtain the desired product as yellow oil.

LC-MS (A): $t_R$=0.39 min; [M+CH$_3$CN+H]+: 234.90.

A.2.3 Synthesis of 2,4-dichloro-6-cyclopropylbenzylamine

A.2.3.1 Synthesis of 2-(2-bromo-4,6-dichlorobenzyl)isoindoline-1,3-dione

To a solution of 1-bromo-2-(bromomethyl)-3,5-dichlorobenzene (1.98 mmol) [J. Med. Chem., 35 (22), 4221 (1992)] in 10 mL CH$_3$CN were added phthalimide (1.98 mmol) and K$_2$CO$_3$ (5.93 mmol). The reaction mixture was stirred at 50° C. for 6 h and then at RT overnight. Sat. aq. NaHCO$_3$ solution was added and the mixture was extracted 3 times with DCM. The combined organic phases were dried over MgSO$_4$ and concentrated in vacuo to obtain the desired product as beige solid.

LC-MS (A): $t_R$=0.99 min; $^1$H NMR (CDCl$_3$) δ: 7.91-7.71 (m, 4H), 7.57 (s, 1H), 7.41 (s, 1H), 5.13 (s, 2H).

A.2.3.2 Synthesis of 2,4-dichloro-6-cyclopropylbenzylamine

To a solution of 2-(2-bromo-4,6-dichlorobenzyl)isoindoline-1,3-dione (1.96 mmol) in 16 mL toluene and 0.8 mL water were added K$_3$PO$_4$ (6.85 mmol), triphenylphosphine (0.23 mmol), cyclopropylboronic acid (2.35 mmol) and Pd(OAc)$_2$ (0.15 mmol). The mixture was stirred at 80° C. for 24 h when another portion of cyclopropylboronic acid (1.96 mmol) and Pd(OAc)$_2$ (0.15 mmol) were added. The reaction mixture was stirred at 80° C. for further 4 days, cooled to RT, quenched with sat. aq. NaHCO$_3$ solution and extracted with EtOAc. The combined organic layers were dried over MgSO$_4$ and concentrated in vacuo to give a crude white solid. This solid was dissolved in 15 mL EtOH and 12.6 mL of hydrazine monohydrate was added. After stirring at RT for 30 min, EtOAc was added. The aqueous phase was basified with 1M NaOH solution and extracted 3 times with EtOAc. The combined organic layers were dried over MgSO$_4$ and concentrated. Purification with CC (KP-NH™ from Biotage) gives the desired compound as red/brown oil.

LC-MS (A): $t_R$=0.60 min; [M+H]+: 216.15.

A.2.4 Synthesis of 2,4-dichloro-6-ethylbenzylamine and 2,4-dichloro-6-vinylbenzylamine To a solution of 2-(2-bromo-4,6-dichlorobenzyl)isoindoline-1,3-dione (4.31 mmol) in 35 mL toluene and 1.7 mL water were added K$_3$PO$_4$ (15.1 mmol), triphenylphosphine (0.50 mmol), ethylboronic acid (4.31 mmol) and Pd(OAc)$_2$ (0.32 mmol). The mixture was stirred at 80° C. for 48 h when another portion of ethylboronic acid (2.1 mmol) and Pd(OAc)$_2$ (0.32 mmol) were added. The reaction mixture was stirred at 80° C. for further 3 days, cooled to RT, quenched with sat. aq. NaHCO$_3$ solution and extracted with EtOAc. The combined organic layers were dried over MgSO$_4$ and concentrated in vacuo to give a white solid. This solid was dissolved in 20 mL EtOH, 10.3 mL of hydrazine monohydrate was added and the mixture was stirred at RT for 35 min. EtOAc was added, the aqueous phase was basified with 1M NaOH solution and extracted 3 times with EtOAc. The combined organic layers were dried over MgSO$_4$ and concentrated to give a mixture of both products as orange oil.

LC-MS (A): $t_R$=0.51 min; [M+H]+: 204.05. (2,4-dichloro-6-ethylbenzylamine)

LC-MS (A): $t_R$=0.49 min; [M+H]+: 202.04. (2,4-dichloro-6-vinylbenzylamine)

A.2.5 Synthesis of (2-(aminomethyl)-3,5-dichlorophenyl)methanol

A.2.5.1 Synthesis of 2-(bromomethyl)-4,6-dichlorobenzonitrile

A solution of 2,4-dichloro-6-methylbenzonitrile (16.9 mmol) in 34 mL chlorobenzene was heated to 50° C. when NBS (18.6 mmol) was added. The flask was purged with Ar before AIBN (1.69 mmol) was added at once still at 50° C. The reaction mixture was then stirred at 78° C. After 2 h and 4 h, another portion of AIBN (1.69 mmol) was added and heating to 78° C. was continued overnight. The solvent was then evaporated off, the resulting residue was redissolved in $Et_2O$ and the remaining solid was removed by filtration. The filtrate was washed twice with 2N HCl solution and brine, it was dried over $MgSO_4$ and concentrated in vacuo. Purification with CC (KP-SIL™ from Biotage) using Hept to EtOAc gives the desired compound as yellowish solid.

LC-MS (A): $t_R$=0.88 min; $^1$H NMR (($CD_3$)$_2$SO) δ: 8.02 (2, 1H), 7.92 (s, 1H), 4.79 (s, 2H).

A.2.5.2 Synthesis of 3,5-dichloro-2-cyanobenzyl acetate

To a solution of 2-(bromomethyl)-4,6-dichlorobenzonitrile (15.1 mmol) in 30 mL AcOH was added NaOAc (75.7 mmol). The suspension was heated to 100° C. for 2 h. The solvent was evaporated off and the residue partitioned between DCM and water. The organic phase was washed with water, dried over $MgSO_4$ and concentrated in vacuo. Purification with CC (KP-SIL™ from Biotage) using Hept/EtOAc (95/5 to 30/70) gives the desired compound as white solid.

LC-MS (B): $t_R$=0.88 min; $^1$H NMR (($CD_3$)$_2$SO) δ: 8.02 (s, 1H), 7.76 (s, 1H), 5.23 (s, 2H), 2.12 (s, 3H).

A.2.5.3 Synthesis of (2-(aminomethyl)-3,5-dichlorophenyl)methanol

To a solution of 3,5-dichloro-2-cyanobenzyl acetate (11.7 mmol) in 50 mL THF was added a solution of $BH_3$ (50 mmol, 1M in THF). The reaction mixture was heated to 75° C. for 7 h and then cooled to 0° C. Water was added followed by MeOH and the mixture was concentrated. The residue was taken up in water and EtOAc, acidified with 1N HCl solution and extracted with DCM. The aqueous phase was then basified with 1M NaOH solution and extracted with DCM. The combined organic layers were dried over $MgSO_4$ and concentrated in vacuo. Purification with CC using DCM/$Et_3$N (99/1) to DCM/MeOH/$Et_3$N (90/10/1) gives the desired compound as pinkish solid.

LC-MS (B): $t_R$=0.42 min; $^1$H NMR (($CD_3$)$_2$SO) δ: 7.46 (s, 1H), 7.38 (s, 1H), 4.60 (s, 2H), 3.76 (s, 2H).

A.2.6 Synthesis of 2,4-dichloro-6-methoxybenzylamine

A.2.6.1 Synthesis of 2,4-dichloro-6-methoxybenzaldehyde

To a solution of 4,6-dichlorosalicylaldehyde (2.69 mmol) in 5 mL DMF was added $K_2CO_3$ (5.39 mmol) followed by iodomethane (2.96 mmol). The reaction mixture was heated to 50° C. for 3.5 h. At RT, the mixture was diluted with EtOAc and washed 3 times with water and then with brine. The combined organic layers were dried over $MgSO_4$ and concentrated in vacuo to give the desired product as beige solid.

LC-MS (A): $t_R$=0.78 min; $^1$H NMR (($CD_3$)$_2$SO) δ: 10.30 (s, 1H), 7.36 (s, 1H), 7.32 (s, 1H), 3.39 (s, 3H).

A.2.6.2 Synthesis of 2,4-dichloro-6-methoxybenzaldehyde oxime

A solution of 2,4-dichloro-6-methoxybenzaldehyde (2.39 mmol) in 5 mL DMF was cooled to 0° C. and NaOAc (2.63 mmol) followed by hydroxylamine HCl (2.63 mmol) were added. The ice bath was removed and the reaction mixture was stirred at RT for 10 min. The mixture was diluted with EtOAc and washed once with water and brine. The combined organic layers were dried over $MgSO_4$ and concentrated in vacuo to give the desired compound as white solid.

LC-MS (A): $t_R$=0.73 min; [M+H]+: 220.14.

A.2.6.3 Synthesis of 2,4-dichloro-6-methoxybenzylamine

A suspension of 2,4-dichloro-6-methoxybenzaldehyde oxime (2.24 mmol) in 3 mL AcOH was cooled to 0° C. and zinc dust (8.53 mmol) was added. The reaction mixture was stirred at RT for 2 h. It was filtered over a pad of celite and washed with EtOAc and MeOH. The filtrate was concentrated and redissolved in water (pH 4 with 2N HCl solution). It was washed once with EtOAc, the ageous phase was basified with 1M NaOH solution, extracted 3 times with EtOAc and DCM. The combined organic layers were dried over $MgSO_4$ and concentrated in vacuo to give the desired product as yellow solid.

LC-MS (A): $t_R$=0.47 min; [M+$CH_3$CN+H]+: 246.99.

A.2.7 Synthesis of 2-(2-(aminomethyl)-3,5-dichlorophenoxy)ethanol

A.2.7.1 Synthesis of 2-(3,5-dichloro-2-formylphenoxy)ethyl acetate

To a solution of 4,6-dichlorosalicylaldehyde (3.72 mmol) in 5 mL DMF was added $Cs_2CO_3$ (3.72 mmol) followed by KI (3.72 mmol) and 2-bromoethyl acetate (8.68 mmol). The reaction mixture was heated to 100° C. for 4 h and then stirred at RT for 3 days. The mixture was diluted with EtOAc and washed 3 times with water and then with brine. The combined organic layers were dried over $MgSO_4$ and concentrated in vacuo. Purification with CC (KP-SIL™ from Biotage) using Hept/EtOAc (4/1) to EtOAc gives the desired compound as beige solid.

LC-MS (B): $t_R$=0.86 min; [M+H]+: 227.12.

A.2.7.2 Synthesis of 2-(3,5-dichloro-2-((hydroxyimino)methyl)phenoxy)ethyl acetate A solution of 2-(3,5-dichloro-2-formylphenoxy)ethyl acetate (1.48 mmol) in 2.5 mL DMF was cooled to 0° C. and NaOAc (1.62 mmol) followed by hydroxylamine HCl (1.62 mmol) were added. The ice bath was removed and the reaction mixture was stirred at RT for 1.5 h. The mixture was diluted with EtOAc and washed once with water and brine. The combined organic layers were dried over $MgSO_4$ and concentrated in vacuo. Purification with CC (KP-SIL™ from Biotage) using Hept and EtOAc gives the desired compound as white solid.

LC-MS (B): $t_R$=0.81 min; [M+H]+: 292.25.

A.2.7.3 Synthesis of 2-(2-(aminomethyl)-3,5-dichlorophenoxy)ethanol

A suspension of 2-(3,5-dichloro-2-((hydroxyimino)methyl)phenoxy)ethyl acetate (1.15 mmol) in 2 mL AcOH was cooled to 0° C. and zinc dust (4.36 mmol) was added. The reaction mixture was stirred at RT for 1 h. It was filtered over a pad of celite and washed with EtOAc and MeOH. The filtrate was concentrated and redissolved in water (pH 4 with 2N HCl solution). It was washed once with EtOAc, the ageous phase was basified with 1M NaOH solution, extracted 3 times with EtOAc and DCM. The combined organic layers were dried over $MgSO_4$ and concentrated in vacuo to give the desired product as white solid.

LC-MS (B): $t_R$=0.46 min; [M+H]+: 236.01.

A.2.8 Synthesis of 2-chloro-3-cyanobenzylamine

A.2.8.1 Synthesis of 3-(bromomethyl)-2-chlorobenzonitrile

A solution of 2-chloro-3-methylbenzonitrile (6.6 mmol) in 25 mL chlorobenzene was heated to 50° C. when NBS (7.9 mmol) was added. The flask was purged with Ar before AIBN (0.66 mmol) was added at once still at 50° C. The reaction mixture was stirred at 80° C. for 2 h. The solvent was evaporated off, the resulting residue was redissolved in $Et_2O$ and washed 3 times with 1N HCl solution and brine. It was dried over $MgSO_4$ and concentrated in vacuo. Purification with CC (KP-SIL™ from Biotage) using Hept to Hept/EtOAc (85/15) gives the desired compound as white solid.

LC-MS (A): $t_R$=0.78 min; $^1$H NMR (($CD_3$)$_2$SO) δ: 7.98 (m, 2H), 7.58 (t, 1H), 4.80 (s, 2H).

A.2.8.2 Synthesis of 2-chloro-3-cyanobenzylamine

To a solution of 3-(bromomethyl)-2-chlorobenzonitrile (0.87 mmol) in 9 mL DMF was added $NaN_3$ (1.3 mmol) and the resulting brown solution was stirred at RT for 20 min. The reaction mixture was diluted with EtOAc, washed twice with water and brine, dried over $MgSO_4$ and concentrated in vacuo. The crude azide was redissolved in 4.3 mL THF and 0.1 mL water. Triphenylphosphine (1.04 mmol) was added and the mixture was stirred at RT overnight. The reaction mixture was acidified with 0.1N HCl solution until pH 3 and it was extracted 3 times with $Et_2O$. The ageous phase was basified with 1M NaOH solution and extracted 3 times with DCM. The combined organic layers were dried over $MgSO_4$ and concentrated in vacuo to give the desired product as yellowish oil.

LC-MS (A): $t_R$=0.31 min; [M+$CH_3$CN+H]+: 208.04.

A.2.9 Synthesis of 2-chloro-4-cyanobenzylamine

This compound was prepared using a method analogous to that of 2-chloro-3-cyanobenzylamine, 3-chloro-4-methylbenzonitrile replacing 2-chloro-3-methylbenzonitrile.

LC-MS (A): $t_R$=0.31 min; [M+$CH_3$CN+H]+: 208.06.

A.2.10 Synthesis of 2,4-dichloro-6-trifluoromethylbenzylamine

A.2.10.1 Synthesis of 2,4-dichloro-6-trifluoromethylphenylacetic acid methyl ester To a suspension of $CuCl_2$ (3.0 mmol) in 30 mL $CH_3CN$ was added tBu-nitrite (4.1 mmol) followed by dropwise addition of 1,1-dichloroethylen (39.1 mmol). A solution of 2,4-dichloro-6-trifluoromethylaniline (2.2 mmol) in 2 mL $CH_3CN$ was slowly added. After stirring at RT overnight, the reaction was quenched with 25% aqueous HCl solution and extracted 3 times with EtOAc. The combined organic layers were dried over $MgSO_4$. After removal of the solvent the crude was redissolved in 3 mL MeOH. After addition of 2.4 mL of a 30% solution of NaOMe in MeOH the mixture was refluxed for 5 h. Then, 1.8 mL concentrated $H_2SO_4$ solution was added at RT and the mixture was heated to reflux for 1 h. After concentrating in vacuo the resulting solid was partitioned between water and DCM. The water phase was extracted 3 times with DCM. The combined organic layers were dried over $MgSO_4$. Purification with CC using Hept/EtOAc (10/1) gives the desired product as yellowish oil.

LC-MS (A): $t_R$=0.93 min; $^1$H NMR (($CD_3$)$_2$SO) δ: 8.11 (s, 1H), 7.88 (s, 1H), 3.97 (s, 2H), 3.65 (s, 3H).

A.2.10.2 Synthesis of 2,4-dichloro-6-trifluoromethylphenylacetic acid

To a solution of 2,4-dichloro-6-trifluoromethylphenylacetic acid methyl ester (0.93 mmol) in 3 mL THF was added an aq. solution of LiOH (2.8 mmol, 2M). After stirring at RT for 3 days, water was added and the mixture was extracted twice with EtOAc. The aqueous phase was acidified to pH 2-3 with 1N HCl solution and extracted 3 times with EtOAc. The combined organic layers were dried over $MgSO_4$ and concentrated in vacuo to give the desired product as white solid.

LC-MS (A): $t_R$=0.78 min; $^1$H NMR (($CD_3$)$_2$SO) δ: 12.8 (brs, 1H), 8.08 (s, 1H), 7.86 (s, 1H), 3.86 (s, 2H).

A.2.10.3 Synthesis of 2,4-dichloro-6-trifluoromethylbenzylamine

To a solution of 2,4-dichloro-6-trifluoromethylphenylacetic acid (0.36 mmol) in 3 mL toluene were added $Et_3N$ (0.44 mmol) and DPPA (0.36 mmol). The reaction mixture was heated to 110° C. for 3 h, cooled to 0° C. and a solution of potassium trimethylsilanolate (0.73 mmol, 1M in THF) was added. After stirring at RT for 30 min, an aqueous solution of 10% citric acid was added and the mixture was extracted twice with $Et_2O$. The aqueous phase was basified with 1M NaOH solution and extracted 3 times with DCM. The combined organic layers were dried over $MgSO_4$ and concentrated in vacuo to give the desired product as white solid.

LC-MS (A): $t_R$=0.48 min; [M+$CH_3$CN+H]+: 284.91.

A.2.11 Synthesis of 2,4-dichloro-6-methoxymethylbenzylamine

A.2.11.1 Synthesis of 2,4-dichloro-6-(methoxymethyl)benzonitrile

To a suspension of 2-(bromomethyl)-4,6-dichlorobenzonitrile (1.04 mmol) (A.2.5.1) in 2.5 mL MeOH was added a solution of NaOMe (1.27 mmol, 0.5M in MeOH). The reaction mixture was heated to 50° C. for 1 h. The mixture was concentrated in vacuo, redissolved in EtOAc and it was then washed twice with an aqueous solution of $KHSO_4$, twice with a sat. aq. $NaHCO_3$ solution and once with brine. The organic layer was dried over $MgSO_4$ and concentrated in vacuo to give the desired product as orange oil.

LC-MS (A): $t_R$=0.84 min; $^1$H NMR (($CD_3$)$_2$SO) δ: 7.97 (s, 1H), 7.67 (s, 1H), 4.59 (s, 2H), 3.37 (s, 3H).

A.2.11.2 Synthesis of 2,4-dichloro-6-methoxymethylbenzylamine

A solution of $BH_3$ (3.5 mL, 1M in THF) was added to a solution of 2,4-dichloro-6-(methoxymethyl)benzonitrile (0.88 mmol) in 3 mL THF. The reaction mixture was heated to 60° C. for 2 h. At 0° C., 3.5 mL MeOH was dropwise added and the mixture was stirred until gas evolution was finished. An aq. solution of 10% NaOH was added still under cooling. The solvent was removed under vacuo, the residue was diluted with water and extracted 3 times with EtOAc. The combined organic layers were dried over $MgSO_4$ and concentrated in vacuo to give the desired product as orange oil.

LC-MS (A): $t_R$=0.45 min; [M+H]+: 220.26.

A.2.12 Synthesis of 2-trifluoromethyl-3-chlorobenzylamine

This compound was prepared using a method analogous to that of 2-chloro-3-cyanobenzylamine, 1-chloro-3-methyl-2-(trifluoromethyl)benzene replacing 2-chloro-3-methylbenzonitrile.

LC-MS (A): $t_R$=0.44 min; [M+$CH_3CN$+H]+: 250.99.

A.2.13 Synthesis of 5,7-dichloro-2,3-dihydro-1H-inden-1-amine

A.2.13.1 Synthesis of 5,7-dichloro-2,3-dihydro-1H-inden-1-one O-methyl oxime To a solution of 5,7-dichloro-1-indanone (0.34 mmol) in 2 mL MeOH was added O-methylhydroxylamine HCl (0.34 mmol). The reaction mixture was stirred at RT for 17 h and then heated to 50° C. for 24 h. The mixture was cooled to RT, diluted with water and extracted 3 times with EtOAc. The combined organic layers were dried over $MgSO_4$ and concentrated in vacuo to give the desired product as white solid.

LC-MS (A): $t_R$=0.99 min; [M+H]+: 229.96.

A.2.13.2 Synthesis of 5,7-dichloro-2,3-dihydro-1H-inden-1-amine

A solution of $BH_3$ (0.6 mL, 1M in THF) was added to a solution of 5,7-dichloro-2,3-dihydro-1H-inden-1-one O-methyl oxime (0.31 mmol) in 1 mL THF. The reaction mixture was heated to 60° C. for 3 days. An aq. 1M NaOH solution was added and heating to 60° C. was continued for another 24 h. The solvent was removed under vacuo, the residue was diluted with a sat. aq. $NaHCO_3$ solution and extracted 3 times with EtOAc. The combined organic layers were dried over $MgSO_4$ and concentrated in vacuo to give the desired product as colorless oil.

LC-MS (A): $t_R$=0.46 min; [M+H]+: 202.03.

A.2.13.3 Chiral Separation of 5,7-dichloro-2,3-dihydro-1H-inden-1-amine rac 5,7-Dichloro-2,3-dihydro-1H-inden-1-amine was separated into the respective enantiomers using prep. chiral HPLC (Daicel, ChiralPak AY-H, 5 µm, 20×250 mm; Hept/EtOH 90/10 0.1% DEA, flow 16 mL/min), detection: UV 210 nm Chiral analytic HPLC (Daicel, ChiralPak AY-H, 5 µm, 250×4.6 mm, Hept 0.05% DEA/EtOH 0.05% DEA 90/10, flow 0.8 mL/min), detection: UV 210 nm Enantiomer A: $t_R$=7.57 min;
Enantiomer B: $t_R$=8.59 min.

A.2.14 Synthesis of 2-bromo-4,6-dichlorobenzylamine

This compound was prepared using a method analogous to that of 2-chloro-3-cyanobenzylamine, 1-bromo-2-(bromomethyl)-3,5-dichlorobenzene [J. Med. Chem., 35 (22), 4221 (1992)] replacing 3-(bromomethyl)-2-chlorobenzonitrile.

LC-MS (A): $t_R$=0.45 min; [M+$CH_3CN$+H]+: 294.83.

A.2.15 Synthesis of 2-((2-(aminomethyl)-3,5-dichlorobenzyl)oxy)ethanol

A.2.15.1 Synthesis of 2-((3,5-dichloro-2-cyanobenzyl)oxy)ethyl acetate

To a solution of 2-(bromomethyl)-4,6-dichlorobenzonitrile (1.3 mmol) (A.2.5.1) and 2-hydroxyethyl acetate (1.43 mmol) in 7 mL THF was added NaH (1.95 mmol, 60% suspension in oil). The reaction mixture was stirred at RT overnight and then poured into a 1M HCl solution. The mixture was extracted twice with EtOAc. The combined organic layers were washed with brine, dried over $MgSO_4$ and concentrated in vacuo. Purification with CC (KP-SIL™ from Biotage) using Hept to Hept/EtOAc (75/25) gives the desired compound as orange oil.

LC-MS (A): $t_R$=0.82 min; [M+H]+: 287.89.

A.2.15.2 Synthesis of 2-((2-(aminomethyl)-3,5-dichlorobenzyl)oxy)ethanol

A solution of $BH_3$ (1.46 mL, 1M in THF) was added to a solution of 2-((3,5-dichloro-2-cyanobenzyl)oxy)ethyl acetate (0.36 mmol) in 1.5 mL MeOH. The reaction mixture was heated to 60° C. for 3 h. At 0° C., 1.5 mL MeOH was dropwise added and the mixture was stirred until gaz evolution was finished. An aq. solution of 10% NaOH was added still under cooling. The solvent was removed under vacuo, the residue was diluted with water and extracted 3 times with EtOAc. The combined organic layers were dried over $MgSO_4$ and concentrated in vacuo to give the desired product as yellow solid.

LC-MS (A): $t_R$=0.43 min; [M+H]+: 250.20.

A.2.16 Synthesis of 4,6-dichloro-2,3-dihydro-1H-inden-1-amine

This compound was prepared using a method analogous to that of 5,7-dichloro-2,3-dihydro-1H-inden-1-amine (A.2.13), 4,6-dichloro-1-indanone replacing 5,7-dichloro-1-indanone.

LC-MS (A): $t_R$=0.50 min; [M+$CH_3CN$+H]+: 242.63.

A.2.17 Synthesis of (4,4-difluoro-1-(6-chloropyridin-3-yl)cyclohexyl)methanamine

A.2.17.1 Synthesis of 5-cyano-5-(6-chloropyridin-3-yl)-2-oxocyclohexanecarboxylic acid methyl ester To a solution of 2-(6-chloro-3-pyridinyl)-acetonitrile (13.1 mmol) in 35 mL THF were added methylacrylate (26.2 mmol) and KOtBu (15.7 mmol). The reaction mixture was stirred at RT for 1 h. The mixture was acidified with 1N HCl solution and then extracted twice with DCM. The combined organic layers were washed with brine, dried over $MgSO_4$ and concentrated in vacuo. Purification with CC (KP-SIL™ from Biotage) using Hept/EtOAc (90/10 to 50/50) gives the desired compound as white solid.
LC-MS (A): $t_R$=0.74 min; [M+CH$_3$CN+H]+: 334.03.

A.2.17.1 Synthesis of 1-(6-chloropyridin-3-yl)-4-oxocyclohexanecarbonitrile

A mixture of 5-cyano-5-(6-chloropyridin-3-yl)-2-oxocyclohexanecarboxylic acid methyl ester (10.6 mmol) and LiCl (21.1 mmol) in 15 mL wet DMSO was heated to 120° C. under microwave conditions for 2 h. The reaction mixture was diluted with water and extracted 3 times with EtOAc. The combined organic layers were washed with brine, dried over MgSO$_4$ and concentrated in vacuo. Purification with CC (KP-SIL™ from Biotage) using Hept/EtOAc (95/5 to 20/80) gives the desired compound as yellow solid.
LC-MS (A): $t_R$=0.56 min; [M+CH$_3$CN+H]+: 276.12.

A.2.17.2 Synthesis of 1-(6-chloropyridin-3-yl)-4,4-difluorocyclohexanecarbonitrile A solution of 1-(6-chloropyridin-3-yl)-4-oxocyclohexanecarbonitrile (3.89 mmol) in 4 mL DCM was cooled to −78° C., DAST (7.78 mmol) was dropwise added and the mixture was stirred for 24 h allowing to reach slowly RT. The reaction mixture was quenched with sat. aq. NaHCO$_3$ solution under ice cooling and diluted with DCM. The organic phase was washed with brine, dried over MgSO$_4$ and concentrated in vacuo. Purification with CC (KP-SIL™ from Biotage) using Hept/EtOAc (90/10 to 50/50) gives the desired compound as beige solid.
LC-MS (A): $t_R$=0.74 min; [M+CH$_3$CN+H]+: 298.00.

A.2.17.3 Synthesis of (4,4-difluoro-1-(6-chloropyridin-3-yl)cyclohexyl)methanamine A solution of 1-(6-chloropyridin-3-yl)-4,4-difluorocyclohexanecarbonitrile (2.02 mmol) in 20 mL THF was added to a solution of BH$_3$ in THF (6.07 mmol, 1 M). After heating to reflux for 1 h, the reaction mixture was cooled in an ice bath before a 2N HCl solution was slowly added. The mixture was then heated to reflux for another 20 min. The reaction mixture was extracted twice with DCM, basified with 1N NaOH solution and extracted 3 times with DCM. The combined organic layers were washed with brine, dried over MgSO$_4$ and concentrated in vacuo to give the desired product as yellow oil.
LC-MS (A): $t_R$=0.46 min; [M+CH$_3$CN+H]+: 302.03.

A.2.18 Synthesis of 2-(4,4-difluoropiperidin-1-yl)-2-(4-(trifluoromethyl)phenyl)-ethanamine A.2.18.1 Synthesis of 2-(4,4-difluoropiperidin-1-yl)-2-(4-(trifluoromethyl)phenyl)-acetonitrile To a solution of 4-(trifluoromethyl)benzaldehyde (5.63 mmol) in 1 mL Et$_2$O were added TMSCN (6.19 mmol) followed by ZnI$_2$ (0.28 mmol). At 0° C., a solution of 4,4-difluoropiperidine HCl (6.19 mmol) and Et$_3$N (11.8 mmol) in 5 mL MeOH was dropwise added maintaining the temperature below 10° C. The reaction mixture was then heated to reflux for 3 h. After cooling to RT, an aqueous solution of 10% Na$_2$CO$_3$ was added and the mixture was extracted 3 times with EtOAc. The combined organic layers were washed with brine, dried over MgSO$_4$ and concentrated in vacuo. Purification with CC (KP-NH™ from Biotage) using Hept to Hept/EtOAc (70/30) gives the desired compound as white solid.
LC-MS (A): $t_R$=0.92 min; [M+CH$_3$CN+H]+: 305.36.

A.2.18.2 Synthesis of 2-(4,4-difluoropiperidin-1-yl)-2-(4-(trifluoromethyl)phenyl)-ethanamine To a solution of 2-(4,4-difluoropiperidin-1-yl)-2-(4-(trifluoromethyl)phenyl)-acetonitrile (2.74 mmol) in 20 mL NH$_3$ in MeOH (7 N) were added at 0° C. a solution of thiophene (0.1 mmol, 4% in diisopropylether) followed by Actimet M Raney-Nickel (0.82 mmol). The reaction mixture was allowed to warm to RT. The reaction mixture was stirred under a hydrogen atmosphere for 30 h. The mixture was then filtered over Celite, washed with MeOH and concentrated in vacuo. The residue was redissolved in 5.5 mL Et$_2$O and 2.8 mL of a 4M HCl solution in dioxane was dropwise added at 0° C. The resulting precipitate was stirred at 0° C. for 30 min, filtered off and dried in vacuo to give the desired product as the corresponding HCl salt as white solid.
LC-MS (A): $t_R$=0.65 min; [M+CH$_3$CN+H]+: 309.02.

A.2.19 Synthesis of 2-(6-methoxypyridin-3-yl)-2-morpholinoethanamine

This compound was prepared using a method analogous to that of 2-(4,4-difluoropiperidin-1-yl)-2-(4-(trifluoromethyl)phenyl)-ethanamine (A.2.18), 6-methoxy-pyridine-3-carboxaldehyde replacing 4-(trifluoromethyl)benzaldehyde and morpholine replacing 4,4-difluoropiperidine HCl.
LC-MS (A): $t_R$=0.28 min; [M+H]+: 238.09.

A.2.20 Synthesis of 2-(6-methylpyridin-3-yl)-2-morpholinoethanamine

This compound was prepared using a method analogous to that of 2-(4,4-difluoropiperidin-1-yl)-2-(4-(trifluoromethyl)phenyl)-ethanamine (A.2.18), 6-methyl-pyridine-3-carboxaldehyde replacing 4-(trifluoromethyl)benzaldehyde and morpholine replacing 4,4-difluoropiperidine HCl.
LC-MS (A): $t_R$=0.12 min; [M+H]+: 222.12.

A.2.21 Synthesis of 2-(2-cyclopropylpyrimidin-5-yl)-2-morpholinoethanamine

This compound was prepared using a method analogous to that of 2-(4,4-difluoropiperidin-1-yl)-2-(4-(trifluoromethyl)phenyl)-ethanamine (A.2.18), 2-cyclopropylpyrimidine-5-carbaldehyde replacing 4-(trifluoromethyl)benzaldehyde and morpholine replacing 4,4-difluoropiperidine HCl.
LC-MS (A): $t_R$=0.34 min; [M+H]+: 249.10.

A.2.22 Synthesis of 2,4-dichloro-6-D3-methylbenzylamine

A.2.22.1 Synthesis of methyl-D3-boronic acid

To a solution of trimethyl borate (17.9 mmol) in 20 mL dry THF was added a solution of methyl-D3-magnesium iodide (10.0 mmol, 1M in Et$_2$O) over 10 min at −78° C. After stirring at −78° C. for 2 h, 5 mL of 1M HCl solution was added. The cooling bath was removed and the mixture was allowed to warm to RT. The reaction was quenched with brine, diluted with Et$_2$O and the organic phase was washed with brine, dried over MgSO$_4$ and concentrated in vacuo to a third of its volume.

A.2.22.2 Synthesis of 2,4-dichloro-6-methyl-D3-benzylamine

This compound was prepared using a method analogous to that of 2,4-dichloro-6-cyclopropylbenzylamine (A.2.3), a solution of freshly prepared methyl-D3-boronic acid in Et$_2$O replacing cyclopropylboronic acid.

LC-MS (D): $t_R$=0.86 min; [M+H]+: 193.52.

A.2.23 Synthesis of 5-chloro-2,3-dihydro-1H-inden-1-amine

This compound was prepared using a method analogous to that of 5,7-dichloro-2,3-dihydro-1H-inden-1-amine (A.2.13), 5-chloro-1-indanone replacing 5,7-dichloro-1-indanone.

LC-MS (A): $t_R$=0.43 min; [M+H]+: 168.22.

A.2.24 Synthesis of 7-chloro-2,3-dihydro-1H-inden-1-amine

This compound was prepared using a method analogous to that of 5,7-dichloro-2,3-dihydro-1H-inden-1-amine (A.2.13), 7-chloro-1-indanone replacing 5,7-dichloro-1-indanone.

LC-MS (A): $t_R$=0.36 min; [M+H]+: 168.22.

A.2.25 Synthesis of 7-bromo-2,3-dihydro-1H-inden-1-amine

This compound was prepared using a method analogous to that of 5,7-dichloro-2,3-dihydro-1H-inden-1-amine (A.2.13), 7-bromo-1-indanone replacing 5,7-dichloro-1-indanone.

LC-MS (C): $t_R$=0.48 min; [M+H]+: 211.98.

A.2.26 Synthesis of (2,4,6-trichlorophenyl)methanamine

To a solution of 2,4,6-trichlorobenzonitrile (0.69 mmol) in 2 mL THF was added a solution of BH$_3$ (2.77 mmol, 1M in THF). The reaction mixture was heated to 40° C. for 2 h and then cooled to RT. 1 mL MeOH was added and the mixture was stirred at RT for 30 min. Water was added, the mixture was basified with 1M NaOH solution and extracted twice with EtOAc. The combined organic layers were dried over MgSO$_4$ and concentrated in vacuo to give the desired product as slightly yellow oil.

LC-MS (C): $t_R$=0.51 min; [M+H]+: 210.13.

A.2.27 Synthesis of (2-(aminomethyl)-3-chlorophenyl)methanol

A.2.27.1 Synthesis of 2-bromo-3-chlorobenzoic acid methyl ester

To a solution of 2-bromo-3-chlorobenzoic acid (7.29 mmol) in 20 mL DCM and 1 mL DMF was added 1.06 mL thionyl chloride. After stirring at RT overnight, 5 mL MeOH were added and stirring was continued at RT for 1 h. The reaction mixture was cooled in an ice bath, quenched by adding a sat. aq. NaHCO$_3$ solution and extracted twice with DCM. The combined organic layers were dried over MgSO$_4$ and concentrated in vacuo to give the desired product as colorless oil.

LC-MS (C): $t_R$=0.86 min; [M+CH$_3$CN+H]+: 291.94.

A.2.27.2 Synthesis of 3-chloro-2-cyanobenzoic acid methyl ester

To a solution of 2-bromo-3-chlorobenzoic acid methyl ester (3.86 mmol) in 4 mL DMF was added CuCN (4.24 mmol) and the reaction mixture was heated to 90° C. overnight. After cooling to 10° C., 10 mL EtOAc and 3 mL 1M NaOH solution were added and stirring was continued at RT for 30 min. The aq. phase was separated and extracted twice with EtOAc. The combined organic layers were washed with brine, dried over MgSO$_4$ and concentrated in vacuo. Purification by preparative LC-MS (method L) gives the desired product as white solid.

LC-MS (C): $t_R$=0.78 min; [M+H]+: 196.02.

A.2.27.3 Synthesis of (2-(aminomethyl)-3-chlorophenyl)methanol

To a slurry of ZnCl$_2$ (0.77 mmol) in 5 mL THF was added LiBH$_4$ (1.64 mmol, 2M in THF) at RT. After heating to 50° C. for 90 min, a solution of 3-chloro-2-cyanobenzoic acid methyl ester (0.81 mmol) in 5 mL THF was slowly added and the mixture was heated to 60° C. overnight. The reaction mixture was then cooled to 5° C., acidified with 2M HCl solution and extracted with EtOAc. The aq. phase was basified with 1M NaOH solution, extracted twice with EtOAc, dried over MgSO$_4$ and concentrated in vacuo to give the desired product as yellowish oil.

LC-MS (C): $t_R$=0.38 min; [M+H]+: 172.11.

A.2.28 Synthesis of 2-amino-5,7-dichloro-2,3-dihydro-1H-inden-1-one

A.2.28.1 Synthesis of 5,7-dichloro-2-(hydroxyimino)-2,3-dihydro-1H-inden-1-one To a solution of 5,7-dichloro-1-indanone (4.73 mmol) in 20 mL MeOH were carefully added tBu-nitrite (5.20 mmol) and 0.15 mL concentrated HCl solution. The reaction mixture was heated to 40° C. for 24 h, concentrated in vacuo, redissolved in EtOAc and extracted with sat. aq. NH$_4$Cl solution. The organic phase was dried over MgSO$_4$ and concentrated in vacuo. Purification with CC using Hept/EtOAc (70/30) gives the desired product as light brown solid.

LC-MS (C): $t_R$=0.75 min; [M+H]+: 230.00.

A.2.28.2 Synthesis of 2-amino-5,7-dichloro-2,3-dihydro-1H-inden-1-one

To a solution of 5,7-dichloro-2-(hydroxyimino)-2,3-dihydro-1H-inden-1-one (0.56 mmol) in 4 mL EtOH were added Pd on carbon (5 mg) and 0.1 mL 25% HCl solution. The mixture was stirred overnight under a hydrogen atmosphere. It was then filtered over a 2 cm pad of celite and washed with EtOH (20 mL) and EtOAc (20 mL). The filtrate was concentrated in vacuo to give the desired product as brown oil.

LC-MS (C): $t_R$=0.50 min; [M+H]+: 216.06.

B. Preparation of Examples

B.1 Synthesis of Compounds of Formula (Ia) (General Procedure)

To a solution of the respective acid (II) (0.61 mmol) in 5 mL DCM were added 0.3 mL DIPEA, HOBT (0.78 mmol) and EDC.HCl (0.78 mmol) followed by the addition of a solution of the respective amine (III) (0.61 mmol), dissolved in 2 mL DCM. The mixture was stirred at RT for 6 h and then diluted with DCM and extracted with sat. aq. NaHCO$_3$ solution and water. The organic layer was dried over MgSO$_4$, concentrated in vacuo and the crude was purified by purification methods listed beforehand to give the desired amides (Ia).

B.2 Synthesis of Compounds of Formula (Ib) (General Procedure)

To a solution of a compound of formula (Ia) (0.61 mmol) in 6 mL THF was added 3-chloroperbenzoic acid (1.84 mmol). The mixture was stirred at RT overnight, diluted with DCM and extracted twice with sat. aq. $NaHCO_3$ solution, twice with sat. aq. $Na_2S_2O_3$ solution and brine. The organic layer was dried over $MgSO_4$, concentrated in vacuo and the crude was purified by purification methods listed beforehand to give the desired N-oxides (Ib).

B.3 Separation of Stereoisomers of Compounds of Formula (I)

Additional information for the purification/separation of mixtures consisting of stereoisomers are summarized in the table below:

| Example | Method | TLC conditions Rf (eluents) | preparative LC-MS $t_R$ [min] |
|---|---|---|---|
| 1 | G | 0.49 (9/1 EtOAc/MeOH) | / |
| 2 | G | 0.38 (9/1 EtOAc/MeOH) | / |
| 6 | G | 0.25 (EtOAc) | / |
| 7 | G | 0.13 (EtOAc) | / |
| 13 | G | 0.35 (DCM/10% MeOH) | / |
| 14 | G | 0.30 (DCM/10% MeOH) | / |
| 27 | U | / | 3.85 |
| 28 | U | / | 4.01 |
| 29 | U | / | 2.73 |
| 30 | U | / | 2.87 |
| 59 | Q | / | 2.39 |
| 60 | Q | / | 2.50 |
| 70 | G | 0.50 (EtOAc) | / |
| 71 | G | 0.43 (EtOAc) | / |
| 74 | Q | / | 2.44 |
| 75 | Q | / | 2.50 |
| 76 | G | 0.52 (EtOAc) | / |
| 77 | G | 0.42 (EtOAc) | / |
| 88 | G | 0.29 (EtOAc) | / |
| 89 | G | 0.27 (EtOAc) | / |
| 94 | G | 0.56 (EtOAc) | / |
| 95 | G | 0.46 (EtOAc) | / |
| 99 | G | 0.31 (EtOAc) | / |
| 100 | G | 0.38 (EtOAc) | / |
| 101 | G | 0.35 (EtOAc) | / |
| 102 | G | 0.37 (EtOAc) | / |
| 107 | G | 0.25 (6:4 H/EtOAc) | / |
| 108 | G | 0.28 (6:4 H/EtOAc) | / |
| 111 | G | 0.22 (7:3 H/EtOAc) | / |
| 112 | G | 0.24 (7:3 H/EtOAc) | / |

B.4 Chiral Separation of Compounds of Formula (I)

rac-2,3-Dihydro-furo[2,3-b]pyridine-3-carboxylic acid 2,4-dichloro-6-methyl-benzylamide was separated into the respective enantiomers using prep. chiral HPLC (Daicel, ChiralPak IC, 5 µm, 20×250 mm; Hept/EtOH 50/50, flow 30 mL/min), detection: UV 210 nm Chiral analytic HPLC (Daicel, ChiralPak IC, 5 µm, 250×4.6 mm, Hept/EtOH 50/50, flow 0.8 mL/min), detection: UV 210 nm Enantiomer A: $t_R$=9.85 min (example 3);
Enantiomer B: $t_R$=17.13 min (example 4).

rac-3,4-Dihydro-2H-pyrano[2,3-b]pyridine-4-carboxylic acid 2,4-dichloro-6-methyl-benzylamide was separated into the respective enantiomers using prep. chiral HPLC (Daicel, ChiralPak IB, 5 µm, 20×250 mm; Hept/EtOH 90/10, flow 16 mL/min), detection: UV 210 nm Chiral analytic HPLC (Daicel, ChiralPak IB, 5 µm, 250×4.6 mm, Hept/EtOH 50/50, flow 0.8 mL/min), detection: UV 210 nm Enantiomer A: $t_R$=21.23 min (example 17);
Enantiomer B: $t_R$=25.65 min (example 18).

rac-2,3-Dihydro-furo[2,3-b]pyridine-3-carboxylic acid 2,4-dichloro-6-hydroxymethyl-benzylamide was separated into the respective enantiomers using prep. chiral HPLC (Daicel, ChiralPak IC, 5 µm, 20×250 mm; Hept/EtOH 50/50, flow 16 mL/min), detection: UV 210 nm Chiral analytic HPLC (Daicel, ChiralPak IC, 5 µm, 250×4.6 mm, Hept/EtOH 50/50, flow 0.8 mL/min), detection: UV 210 nm Enantiomer A: $t_R$=7.49 min (example 24);
Enantiomer B: $t_R$=10.50 min (example 25).

rac-2,3-Dihydro-furo[2,3-b]pyridine-3-carboxylic acid 2-bromo-4,6-dichloro-benzylamide was separated into the respective enantiomers using prep. chiral HPLC (Daicel, ChiralPak IC, 5 µm, 20×250 mm; Hept/EtOH 10/90, flow 25 mL/min), detection: UV 210 nm Chiral analytic HPLC (Daicel, ChiralPak IC, 5 µm, 250×4.6 mm, Hept/EtOH 10/90, flow 1.2 mL/min), detection: UV 210 nm Enantiomer A: $t_R$=5.35 min (example 79);
Enantiomer B: $t_R$=8.52 min (example 80).

Crude 2,3-dihydro-furo[2,3-b]pyridine-3-carboxylic acid [2-morpholin-4-yl-2-(2-trifluoromethyl-pyrimidin-5-yl)-ethyl]-amide, consisting of 4 stereoisomers was separated into the 2 epimeric mixtures using prep. chiral HPLC (Daicel, ChiralPak IC, 5 µm, 20×250 mm; Hept/EtOH 0.1% DEA 20/80, flow 16 mL/min), detection: UV 280 nm.

Epimeric mixture 1 was separated using prep. chiral HPLC (Daicel, ChiralPak IC, 5 µm, 20×250 mm; EtOH/DCM 90/10, flow 16 mL/min), detection: UV 286 nm Chiral analytic HPLC (Daicel, ChiralPak IC, 5 µm, 250×4.6 mm, EtOH/DCM 90/10, flow 0.8 mL/min), detection: UV 210 nm Isomer A: $t_R$=5.56 min (example 81);
Isomer B: $t_R$=7.79 min (example 82).

Epimeric mixture 2 was separated using prep. chiral HPLC (Daicel, ChiralPak IC, 5 µm, 20×250 mm; EtOH/DCM 90/10, flow 20 mL/min), detection: UV 286 nm Chiral analytic HPLC (Daicel, ChiralPak IC, 5 µm, 250×4.6 mm, EtOH/DCM 90/10, flow 0.8 mL/min), detection: UV 210 nm Isomer C: $t_R$=6.24 min (example 83);
Isomer D: $t_R$=11.20 min (example 84).

Example 76 was separated into the respective enantiomers using prep. chiral HPLC (Daicel, ChiralPak IC, 5 µm, 20×250 mm; Hept/EtOH 0.1% DEA 10/90, flow 20 mL/min), detection: UV 210 nm Chiral analytic HPLC (Daicel, ChiralPak IC, 5 µm, 250×4.6 mm, Hept 0.05% DEA/EtOH 0.05% DEA 10/90, flow 1.0 mL/min), detection: UV 210 nm Enantiomer A: $t_R$=6.67 min (example 85);
Enantiomer B: $t_R$=10.42 min (example 86).

Example 96 was separated into the respective enantiomers using prep. chiral HPLC (Daicel, ChiralPak IC, 5 µm, 20×250 mm; Hept/EtOH 50/50, flow 22 mL/min), detection: UV 210 nm Chiral analytic HPLC (Daicel, ChiralPak IC, 5 µm, 250×4.6 mm, Hept/EtOH 50/50, flow 1.0 mL/min), detection: UV 210 nm Enantiomer A: $t_R$=7.79 min (example 97);
Enantiomer B: $t_R$=13.50 min (example 98).

Crude mixture (enantiomer A of 5,7-dichloro-2,3-dihydro-1H-inden-1-amine (A.2.13.3) was used in the synthesis described under B.1) consisting of either 2,3-dihydro-furo[2,3-b]pyridine-3-carboxylic acid ((R)-5,7-dichloro-indan-1-yl)-amide or 2,3-dihydro-furo[2,3-b]pyridine-3-carboxylic acid ((S)-5,7-dichloro-indan-1-yl)-amide was separated into the respective enantiomers using prep. chiral HPLC (Daicel, ChiralPak IC, 5 μm, 20×250 mm; Hept/EtOH 10/90 0.1% DEA, flow 20 mL/min), detection: UV 210 nm Chiral analytic HPLC (Daicel, ChiralPak IC, 5 μm, 250× 4.6 mm, Hept 0.05% DEA/EtOH 0.05% DEA 10/90, flow 1.0 mL/min), detection: UV 210 nm Enantiomer A: $t_R$=5.98 min (example 104);
Enantiomer B: $t_R$=10.42 min (example 86).

Crude mixture (enantiomer B of 5,7-dichloro-2,3-dihydro-1H-inden-1-amine (A.2.13.3) was used in the synthesis described under B.1) consisting of either 2,3-dihydro-furo[2,3-b]pyridine-3-carboxylic acid ((S)-5,7-dichloro-indan-1-yl)-amide or 2,3-dihydro-furo[2,3-b]pyridine-3-carboxylic acid ((R)-5,7-dichloro-indan-1-yl)-amide was separated into the respective enantiomers using prep. chiral HPLC (Daicel, ChiralPak IC, 5 μm, 20×250 mm; Hept/EtOH 10/90 0.1% DEA, flow 20 mL/min), detection: UV 210 nm Chiral analytic HPLC (Daicel, ChiralPak IC, 5 μm, 250× 4.6 mm, Hept 0.05% DEA/EtOH 0.05% DEA 10/90, flow 1.0 mL/min), detection: UV 210 nm Enantiomer A: $t_R$=6.67 min (example 85);
Enantiomer B: $t_R$=8.84 min (example 105).

Example 102 was separated into the respective enantiomers using prep. chiral HPLC (Daicel, ChiralPak IC, 5 μm, 20×250 mm; Hept/EtOH 20/80, flow 16 mL/min), detection: UV 210 nm Chiral analytic HPLC (Daicel, ChiralPak IC, 5 μm, 250× 4.6 mm, Hept/EtOH 20/80, flow 0.8.0 mL/min), detection: UV 210 nm Enantiomer A: $t_R$=7.09 min (example 109);
Enantiomer B: $t_R$=11.56 min (example 110).

| Compound | Name | Purification method | LC-MS | $t_R$ [min] | [M + H]$^+$ |
|---|---|---|---|---|---|
| Example 1 | 2,3-Dihydro-furo[2,3-b]pyridine-3-carboxylic acid ((S)-1-cyclohexyl-2-hydroxy-ethyl)-amide (epimer A) | see B.3 | E | 0.65 | 291.2 |
| Example 2 | 2,3-Dihydro-furo[2,3-b]pyridine-3-carboxylic acid ((S)-1-cyclohexyl-2-hydroxy-ethyl)-amide (epimer B) | see B.3 | E | 0.66 | 291.2 |
| Example 3 | 2,3-Dihydro-furo[2,3-b]pyridine-3-carboxylic acid 2,4-dichloro-6-methyl-benzylamide (enantiomer A) | see B.4 | E | 0.9 | 337.0 |
| Example 4 | 2,3-Dihydro-furo[2,3-b]pyridine-3-carboxylic acid 2,4-dichloro-6-methyl-benzylamide (enantiomer B) | see B.4 | E | 0.9 | 337.0 |
| Example 5 | rac-2,3-Dihydro-furo[2,3-b]pyridine-3-carboxylic acid 2,4-dichloro-benzylamide | G (EtOAc) | E | 0.84 | 323.0 |
| Example 6 | 2,3-Dihydro-furo[2,3-b]pyridine-3-carboxylic acid [(S)-1-(2,4-dichloro-phenyl)-2-hydroxy-ethyl]-amide (epimer A) | see B.3 | E | 0.73 | 353.0 |
| Example 7 | 2,3-Dihydro-furo[2,3-b]pyridine-3-carboxylic acid [(S)-1-(2,4-dichloro-phenyl)-2-hydroxy-ethyl]-amide (epimer B) | see B.3 | E | 0.73 | 353.0 |
| Example 8 | (S)-3,4-Dihydro-2H-pyrano[2,3-b]pyridine-4-carboxylic acid ((S)-1-cyclohexyl-2-hydroxy-ethyl)-amide and (R)-3,4-Dihydro-2H-pyrano[2,3-b]pyridine-4-carboxylic acid ((S)-1-cyclohexyl-2-hydroxy-ethyl)-amide | P | E | 0.61 | 305.2 |
| Example 9 | (S)-3,4-Dihydro-2H-pyrano[2,3-b]pyridine-4-carboxylic acid [(S)-1-(2,4-dichloro-phenyl)-2-hydroxy-ethyl]-amide and (R)-3,4-Dihydro-2H-pyrano[2,3-b]pyridine-4-carboxylic acid [(S)-1-(2,4-dichloro-phenyl)-2-hydroxy-ethyl]-amide | P | E | 0.68 | 367.1 |
| Example 10 | rac-3,4-Dihydro-2H-pyrano[2,3-b]pyridine-4-carboxylic acid (1-hydroxy-cyclohexylmethyl)-amide | P | E | 0.5 | 291.2 |
| Example 11 | rac-3-Fluoro-2,3-dihydro-furo[2,3-b]pyridine-3-carboxylic acid 2,4-dichloro-6-methyl-benzylamide | G (4:6 Hept/EtOAc) | E | 0.99 | 355.0 |
| Example 12 | rac-4-Fluoro-3,4-dihydro-2H-pyrano[2,3-b]pyridine-4-carboxylic acid 2,4-dichloro-6-methyl-benzylamide | N | E | 0.98 | 369.0 |

|  |  |  | LC-MS | | |
|---|---|---|---|---|---|
| Compound | Name | Purification method | LC-MS | $t_R$ [min] | $[M + H]^+$ |
| Example 13 | rac-2,3-Dihydro-furo[2,3-b]pyridine-3-carboxylic acid (1-cycloheptyl-2-hydroxy-ethyl)-amide (diastereoisomer A) | see B.3 | E | 0.72 | 305.2 |
| Example 14 | rac-2,3-Dihydro-furo[2,3-b]pyridine-3-carboxylic acid (1-cycloheptyl-2-hydroxy-ethyl)-amide (diastereoisomer B) | see B.3 | E | 0.73 | 305.2 |
| Example 15 | rac-2,3-Dihydro-furo[2,3-b]pyridine-3-carboxylic acid 2,4-dichloro-6-fluoro-benzylamide | L | E | 0.83 | 341.0 |
| Example 16 | rac-2,3-Dihydro-furo[2,3-b]pyridine-3-carboxylic acid 2-chloro-3-trifluoromethyl-benzylamide | G (EtOAc) | E | 0.86 | 357.1 |
| Example 17 | 3,4-Dihydro-2H-pyrano[2,3-b]pyridine-4-carboxylic acid 2,4-dichloro-6-methyl-benzylamide (enantiomer A) | see B.4 | E | 0.86 | 351.1 |
| Example 18 | 3,4-Dihydro-2H-pyrano[2,3-b]pyridine-4-carboxylic acid 2,4-dichloro-6-methyl-benzylamide (enantiomer B) | see B.4 | E | 0.86 | 351.1 |
| Example 19 | rac-3,4-Dihydro-2H-pyrano[2,3-b]pyridine-4-carboxylic acid [1-(6-chloro-pyridin-3-yl)-cyclohexylmethyl]-amide | M | E | 0.81 | 386.2 |
| Example 20 | rac-3-Fluoro-2,3-dihydro-furo[2,3-b]pyridine-3-carboxylic acid 2,3-dichloro-benzylamide | M | E | 0.9 | 341.0 |
| Example 21 | rac-2,3-Dihydro-furo[2,3-b]pyridine-3-carboxylic acid 2,4-dichloro-6-cyclopropyl-benzylamide | M | E | 0.98 | 363.1 |
| Example 22 | rac-2,3-Dihydro-furo[2,3-b]pyridine-3-carboxylic acid 2,4-dichloro-6-ethyl-benzylamide | L | E | 0.97 | 351.1 |
| Example 23 | rac-2,3-Dihydro-furo[2,3-b]pyridine-3-carboxylic acid 2,4-dichloro-6-vinyl-benzylamide | L | E | 0.94 | 349.0 |
| Example 24 | 2,3-Dihydro-furo[2,3-b]pyridine-3-carboxylic acid 2,4-dichloro-6-hydroxymethyl-benzylamide (enantiomer A) | see B.4 | E | 0.73 | 353.0 |
| Example 25 | 2,3-Dihydro-furo[2,3-b]pyridine-3-carboxylic acid 2,4-dichloro-6-hydroxymethyl-benzylamide (enantiomer B) | see B.4 | E | 0.73 | 353.0 |
| Example 26 | rac-2,3-Dihydro-furo[2,3-b]pyridine-3-carboxylic acid 2,4-dichloro-6-methoxy-benzylamide | G (DCM/10% MeOH) | E | 0.87 | 353.0 |
| Example 27 | rac-2,3-Dihydro-furo[2,3-b]pyridine-3-carboxylic acid [2-(4,4-difluoro-piperidin-1-yl)-2-(2-methyl-pyrimidin-5-yl)-ethyl]-amide (diastereoisomer A) | see B.3 | F | 0.45 | 404.2 |
| Example 28 | rac-2,3-Dihydro-furo[2,3-b]pyridine-3-carboxylic acid [2-(4,4-difluoro-piperidin-1-yl)-2-(2-methyl-pyrimidin-5-yl)-ethyl]-amide (diastereoisomer B) | see B.3 | F | 0.46 | 404.2 |
| Example 29 | rac-2,3-Dihydro-furo[2,3-b]pyridine-3-carboxylic acid [2-(2-methyl-pyrimidin-5-yl)-2-morpholin-4-yl-ethyl]-amide (diastereoisomer A) | see B.3 | F | 0.49 | 370.2 |
| Example 30 | rac-2,3-Dihydro-furo[2,3-b]pyridine-3-carboxylic acid [2-(2-methyl-pyrimidin-5-yl)-2-morpholin-4-yl-ethyl]-amide (diastereoisomer B) | see B.3 | F | 0.52 | 370.1 |
| Example 31 | rac-3,4-Dihydro-2H-pyrano[2,3-b]pyridine-4-carboxylic acid 3-chloro-2-methyl-benzylamide | H | E | 0.76 | 317.1 |
| Example 32 | rac-3,4-Dihydro-2H-pyrano[2,3-b]pyridine-4-carboxylic acid 2-chloro-4-fluoro-benzylamide | H | E | 0.7 | 321.1 |

| Compound | Name | Purification method | LC-MS | t_R [min] | [M + H]+ |
|---|---|---|---|---|---|
| Example 33 | rac-3,4-Dihydro-2H-pyrano[2,3-b]pyridine-4-carboxylic acid 4-phenoxy-benzylamide | H | E | 0.86 | 361.2 |
| Example 34 | rac-3,4-Dihydro-2H-pyrano[2,3-b]pyridine-4-carboxylic acid 2,3-dichloro-benzylamide | H | E | 0.77 | 337.0 |
| Example 35 | rac-3,4-Dihydro-2H-pyrano[2,3-b]pyridine-4-carboxylic acid 4-chloro-benzylamide | H | E | 0.69 | 303.1 |
| Example 36 | rac-3,4-Dihydro-2H-pyrano[2,3-b]pyridine-4-carboxylic acid 4-trifluoromethyl-benzylamide | H | E | 0.76 | 337.1 |
| Example 37 | rac-3,4-Dihydro-2H-pyrano[2,3-b]pyridine-4-carboxylic acid (4-chloro-benzyl)-methyl-amide | H | E | 0.76 | 317.1 |
| Example 38 | rac-3,4-Dihydro-2H-pyrano[2,3-b]pyridine-4-carboxylic acid [2-(2,4-dichloro-phenyl)-ethyl]-amide | H | E | 0.83 | 351.1 |
| Example 39 | rac-3,4-Dihydro-2H-pyrano[2,3-b]pyridine-4-carboxylic acid 2,4-dichloro-benzylamide | H | E | 0.79 | 337.1 |
| Example 40 | rac-3,4-Dihydro-2H-pyrano[2,3-b]pyridine-4-carboxylic acid 2-chloro-3-trifluoromethyl-benzylamide | H | E | 0.82 | 371.0 |
| Example 41 | rac-8-Oxy-3,4-dihydro-2H-pyrano[2,3-b]pyridine-4-carboxylic acid 2,4-dichloro-6-methyl-benzylamide | M | E | 0.73 | 367.0 |
| Example 42 | rac-2,3-Dihydro-furo[2,3-b]pyridine-3-carboxylic acid 3-chloro-2-methyl-benzylamide | H | E | 0.81 | 303.1 |
| Example 43 | rac-2,3-Dihydro-furo[2,3-b]pyridine-3-carboxylic acid 2-chloro-4-fluoro-benzylamide | H | E | 0.75 | 307.1 |
| Example 44 | rac-2,3-Dihydro-furo[2,3-b]pyridine-3-carboxylic acid 4-phenoxy-benzylamide | H | E | 0.89 | 347.1 |
| Example 45 | rac-2,3-Dihydro-furo[2,3-b]pyridine-3-carboxylic acid 2,3-dichloro-benzylamide | H | E | 0.81 | 323.0 |
| Example 46 | rac-2,3-Dihydro-furo[2,3-b]pyridine-3-carboxylic acid 4-chloro-benzylamide | H | E | 0.74 | 289.1 |
| Example 47 | rac-2,3-Dihydro-furo[2,3-b]pyridine-3-carboxylic acid 4-trifluoromethyl-benzylamide | H | E | 0.81 | 323.1 |
| Example 48 | rac-2,3-Dihydro-furo[2,3-b]pyridine-3-carboxylic acid (4-chloro-benzyl)-methyl-amide | H | E | 0.82 | 303.1 |
| Example 49 | rac-2,3-Dihydro-furo[2,3-b]pyridine-3-carboxylic acid [2-(2,4-dichloro-phenyl)-ethyl]-amide | H | E | 0.87 | 337.0 |
| Example 50 | rac-2,3-Dihydro-furo[2,3-b]pyridine-3-carboxylic acid 2,4-dichloro-6-(2-hydroxy-ethoxy)-benzylamide | G (DCM/10% MeOH) | E | 0.79 | 383.0 |
| Example 51 | rac-3,4-Dihydro-2H-pyrano[2,3-b]pyridine-4-carboxylic acid 2,4-dichloro-6-hydroxymethyl-benzylamide | H | E | 0.69 | 367.0 |
| Example 52 | 3,4-Dihydro-2H-pyrano[2,3-b]pyridine-4-carboxylic acid (1-cycloheptyl-2-hydroxy-ethyl)-amide (mixture of 4 stereoisomers) | H | E | 0.68 | 319.2 |
| Example 53 | rac-3,4-Dihydro-2H-pyrano[2,3-b]pyridine-4-carboxylic acid 3-fluoro-4-trifluoromethoxy-benzylamide | H | E | 0.82 | 371.1 |
| Example 54 | rac-3,4-Dihydro-2H-pyrano[2,3-b]pyridine-4-carboxylic acid (1-phenyl-cyclohexylmethyl)-amide | H | E | 0.92 | 351.2 |

| Compound | Name | Purification method | LC-MS | t_R [min] | [M + H]+ |
|---|---|---|---|---|---|
| Example 55 | rac-3-Fluoro-2,3-dihydro-furo[2,3-b]pyridine-3-carboxylic acid 2-chloro-3-trifluoromethyl-benzylamide | G (1:1 Hept/EtOAc) | E | 0.94 | 375.0 |
| Example 56 | rac-2,3-Dihydro-furo[2,3-b]pyridine-3-carboxylic acid 2-chloro-3-cyano-benzylamide | N | E | 0.66 | 314.0 |
| Example 57 | rac-2,3-Dihydro-furo[2,3-b]pyridine-3-carboxylic acid 3-fluoro-4-trifluoromethoxy-benzylamide | H | E | 0.86 | 357.1 |
| Example 58 | rac-3,4-Dihydro-2H-pyrano[2,3-b]pyridine-4-carboxylic acid [1-(2,4-dichloro-phenyl)-cyclopropyl]-amide | P | E | 0.86 | 363.1 |
| Example 59 | rac-2,3-Dihydro-furo[2,3-b]pyridine-3-carboxylic acid [2-morpholin-4-yl-2-(2-trifluoromethyl-pyrimidin-5-yl)-ethyl]-amide (diastereoisomer A) | see B.3 | F | 0.87 | 424.2 |
| Example 60 | rac-2,3-Dihydro-furo[2,3-b]pyridine-3-carboxylic acid [2-morpholin-4-yl-2-(2-trifluoromethyl-pyrimidin-5-yl)-ethyl]-amide (diastereoisomer B) | see B.3 | F | 0.89 | 424.2 |
| Example 61 | rac-2,3-Dihydro-furo[2,3-b]pyridine-3-carboxylic acid 2-chloro-4-cyano-benzylamide | N | D | 0.68 | 314.1 |
| Example 62 | 2,3-Dihydro-furo[2,3-b]pyridine-3-carboxylic acid [2-(4,4-difluoro-piperidin-1-yl)-2-(2-trifluoromethyl-pyrimidin-5-yl)-ethyl]-amide (mixture of 4 stereoisomers) | N | F | 0.78 | 458.2 |
| Example 63 | rac-2,3-Dihydro-furo[2,3-b]pyridine-3-carboxylic acid (1-carbamoyl-cyclopentyl)-amide | N | E | 0.71 | 276.2 |
| Example 64 | 2,3-Dihydro-furo[2,3-b]pyridine-3-carboxylic acid (2-phenyl-cyclopropyl)-amide (mixture of 4 stereoisomers) | N | E | 0.74 | 281.2 |
| Example 65 | (S)-2,3-Dihydro-furo[2,3-b]pyridine-3-carboxylic acid ((1S,2R)-2-hydroxy-indan-1-yl)-amide and (R)-2,3-Dihydro-furo[2,3-b]pyridine-3-carboxylic acid ((1S,2R)-2-hydroxy-indan-1-yl)-amide | N | E | 0.58 | 297.1 |
| Example 66 | 2,3-Dihydro-furo[2,3-b]pyridine-3-carboxylic acid (2-carbamoyl-cyclohexyl)-amide (mixture of 4 stereoisomers) | N | E | 0.73 | 290.2 |
| Example 67 | rac-3,4-Dihydro-2H-pyrano[2,3-b]pyridine-4-carboxylic acid (1-(6-chloropyridin-3-yl)-4,4-difluorocyclohexylmethyl)-amide | L | E | 0.74 | 422.2 |
| Example 68 | rac-2,3-Dihydro-furo[2,3-b]pyridine-3-carboxylic acid 2,4-dichloro-6-trifluoromethyl-benzylamide | L | E | 0.92 | 391.0 |
| Example 69 | (S)-2,3-Dihydro-furo[2,3-b]pyridine-3-carboxylic acid (R)-indan-1-ylamide and (R)-2,3-Dihydro-furo[2,3-b]pyridine-3-carboxylic acid (R)-indan-1-ylamide | G (EtOAc) | E | 0.73 | 281.1 |
| Example 70 | 2,3-Dihydro-furo[2,3-b]pyridine-3-carboxylic acid [(R)-1-(2,4-dichloro-phenyl)-ethyl]-amide (epimer A) | see B.3 | E | 0.90 | 337.0 |
| Example 71 | 2,3-Dihydro-furo[2,3-b]pyridine-3-carboxylic acid [(R)-1-(2,4-dichloro-phenyl)-ethyl]-amide (epimer B) | see B.3 | E | 0.88 | 337.0 |
| Example 72 | rac-2,3-Dihydro-furo[2,3-b]pyridine-3-carboxylic acid 2,4-dichloro-6-methoxymethyl-benzylamide | G (1:3 Hept/EtOAc) | E | 0.88 | 367.0 |
| Example 73 | rac-2,3-Dihydro-furo[2,3-b]pyridine-3-carboxylic acid 3-chloro-2-trifluoromethyl-benzylamide | L | E | 0.86 | 357.1 |
| Example 74 | rac-2,3-Dihydro-furo[2,3-b]pyridine-3-carboxylic acid [2-(6-chloro-pyridin-3-yl)-2-(4,4-difluoro- | see B.3 | F | 0.55 | 423.2 |

|  |  |  | LC-MS | | |
|---|---|---|---|---|---|
| Compound | Name | Purification method | LC-MS | $t_R$ [min] | $[M + H]^+$ |
| Example 75 | piperidin-1-yl)-ethyl]-amide (diastereoisomer A) rac-2,3-Dihydro-furo[2,3-b]pyridine-3-carboxylic acid [2-(6-chloro-pyridin-3-yl)-2-(4,4-difluoro-piperidin-1-yl)-ethyl]-amide (diastereoisomer B) | see B.3 | F | 0.56 | 423.2 |
| Example 76 | rac-2,3-Dihydro-furo[2,3-b]pyridine-3-carboxylic acid (5,7-dichloro-indan-1-yl)-amide (diastereoisomer A) | see B.3 | E | 0.89 | 349.0 |
| Example 77 | rac-2,3-Dihydro-furo[2,3-b]pyridine-3-carboxylic acid (5,7-dichloro-indan-1-yl)-amide (diastereoisomer B) | see B.3 | E | 0.89 | 349.1 |
| Example 78 | 2,3-Dihydro-furo[2,3-b]pyridine-3-carboxylic acid [2-(4,4-difluoro-piperidin-1-yl)-2-(4-trifluoromethyl-phenyl)-ethyl]-amide (mixture of 4 stereoisomers) | G (EtOAc/5% MeOH) | F | 0.69 | 456.2 |
| Example 79 | 2,3-Dihydro-furo[2,3-b]pyridine-3-carboxylic acid 2-bromo-4,6-dichloro-benzylamide (enantiomer A) | see B.4 | E | 0.91 | 400.9 |
| Example 80 | 2,3-Dihydro-furo[2,3-b]pyridine-3-carboxylic acid 2-bromo-4,6-dichloro-benzylamide (enantiomer B) | see B.4 | E | 0.91 | 401.0 |
| Example 81 | 2,3-Dihydro-furo[2,3-b]pyridine-3-carboxylic acid [2-morpholin-4-yl-2-(2-trifluoromethyl-pyrimidin-5-yl)-ethyl]-amide (isomer A) | see B.4 | F | 0.56 | 424.2 |
| Example 82 | 2,3-Dihydro-furo[2,3-b]pyridine-3-carboxylic acid [2-morpholin-4-yl-2-(2-trifluoromethyl-pyrimidin-5-yl)-ethyl]-amide (isomer B) | see B.4 | F | 0.54 | 424.2 |
| Example 83 | 2,3-Dihydro-furo[2,3-b]pyridine-3-carboxylic acid [2-morpholin-4-yl-2-(2-trifluoromethyl-pyrimidin-5-yl)-ethyl]-amide (isomer C) | see B.4 | F | 0.54 | 424.2 |
| Example 84 | 2,3-Dihydro-furo[2,3-b]pyridine-3-carboxylic acid [2-morpholin-4-yl-2-(2-trifluoromethyl-pyrimidin-5-yl)-ethyl]-amide (isomer D) | see B.4 | F | 0.56 | 424.2 |
| Example 85 | 2,3-Dihydro-furo[2,3-b]pyridine-3-carboxylic acid (5,7-dichloro-indan-1-yl)-amide (enantiomer A of example 76) | see B.4 | E | 0.89 | 349 |
| Example 86 | 2,3-Dihydro-furo[2,3-b]pyridine-3-carboxylic acid (5,7-dichloro-indan-1-yl)-amide (enantiomer B of example 76) | see B.4 | E | 0.89 | 349 |
| Example 87 | 2,3-Dihydro-furo[2,3-b]pyridine-3-carboxylic acid [2-(6-methoxy-pyridin-3-yl)-2-morpholin-4-yl-ethyl]-amide (mixture of 4 stereoisomers) | P | F | 0.39 | 385.2 |
| Example 88 | rac-2,3-Dihydro-furo[2,3-b]pyridine-3-carboxylic acid (3-oxo-indan-1-yl)-amide (diastereoisomer A) | see B.3 | E | 0.54 | 295.1 |
| Example 89 | rac-2,3-Dihydro-furo[2,3-b]pyridine-3-carboxylic acid (3-oxo-indan-1-yl)-amide (diastereoisomer B) | see B.3 | E | 0.56 | 295.1 |
| Example 90 | 2,3-Dihydro-furo[2,3-b]pyridine-3-carboxylic acid [2-(6-methyl-pyridin-3-yl)-2-morpholin-4-yl-ethyl]-amide (mixture of 4 stereoisomers) | T | E | 0.34 | 369.2 |
| Example 91 | 2,3-Dihydro-furo[2,3-b]pyridine-3-carboxylic acid [2-(2-cyclopropyl-pyrimidin-5-yl)-2-morpholin-4-yl-ethyl]-amide (mixture of 4 stereoisomers) | P | F | 0.42 | 396.2 |

-continued

| Compound | Name | Purification method | LC-MS | $t_R$ [min] | $[M + H]^+$ |
|---|---|---|---|---|---|
| Example 92 | 2,3-Dihydro-furo[2,3-b]pyridine-3-carboxylic acid [2-morpholin-4-yl-2-(6-trifluoromethyl-pyridin-3-yl)-ethyl]-amide (mixture of 4 stereoisomers) | P | F | 0.49 | 423.2 |
| Example 93 | rac-2,3-Dihydro-furo[2,3-b]pyridine-3-carboxylic acid 2,4-dichloro-6-(2-hydroxy-ethoxymethyl)-benzylamide | G (DCM/10% MeOH) | E | 0.76 | 397.1 |
| Example 94 | rac-2,3-Dihydro-furo[2,3-b]pyridine-3-carboxylic acid (4,6-dichloro-indan-1-yl)-amide (diastereoisomer A) | see B.3 | E | 0.95 | 349 |
| Example 95 | rac-2,3-Dihydro-furo[2,3-b]pyridine-3-carboxylic acid (4,6-dichloro-indan-1-yl)-amide (diastereoisomer B) | see B.3 | E | 0.95 | 349 |
| Example 96 | rac-2,3-Dihydro-furo[2,3-b]pyridine-3-carboxylic acid 2,4-dichloro-6-trideuteromethyl-benzylamide | G (EtOAc) | E | 0.96 | 340.2 |
| Example 97 | 2,3-Dihydro-furo[2,3-b]pyridine-3-carboxylic acid 2,4-dichloro-6-trideuteromethyl-benzylamide (enantiomer A) | see B.4 | E | 0.96 | 340.2 |
| Example 98 | 2,3-Dihydro-furo[2,3-b]pyridine-3-carboxylic acid 2,4-dichloro-6-trideuteromethyl-benzylamide (enantiomer B) | see B.4 | E | 0.96 | 340.2 |
| Example 99 | rac-2,3-Dihydro-furo[2,3-b]pyridine-3-carboxylic acid (5-chloro-indan-1-yl)-amide (diastereoisomer A) | see B.3 | E | 0.91 | 315.2 |
| Example 100 | rac-2,3-Dihydro-furo[2,3-b]pyridine-3-carboxylic acid (5-chloro-indan-1-yl)-amide (diastereoisomer B) | see B.3 | E | 0.91 | 315.2 |
| Example 101 | rac-2,3-Dihydro-furo[2,3-b]pyridine-3-carboxylic acid (7-chloro-indan-1-yl)-amide (diastereoisomer A) | see B.3 | E | 0.83 | 315.2 |
| Example 102 | rac-2,3-Dihydro-furo[2,3-b]pyridine-3-carboxylic acid (7-chloro-indan-1-yl)-amide (diastereoisomer B) | see B.3 | E | 0.83 | 315.2 |
| Example 103 | rac-2,3-Dihydro-furo[2,3-b]pyridine-3-carboxylic acid 2-chloro-4-trifluoromethyl-benzylamide | N | E | 0.95 | 357.2 |
| Example 104 | 2,3-Dihydro-furo[2,3-b]pyridine-3-carboxylic acid (5,7-dichloro-indan-1-yl)-amide (enantiomer A of example 77) | see B.4 | E | 0.96 | 349.2 |
| Example 105 | 2,3-Dihydro-furo[2,3-b]pyridine-3-carboxylic acid (5,7-dichloro-indan-1-yl)-amide (enantiomer B of example 77) | see B.4 | E | 0.96 | 349.1 |
| Example 106 | rac-2,3-Dihydro-furo[2,3-b]pyridine-3-carboxylic acid [3-(2,4-dichloro-phenyl)-propyl]-amide | G (1:1 Hept/EtOAc) | E | 1.02 | 351.2 |
| Example 107 | 2,3-dihydrofuro[2,3-b]pyridine-3-carboxylic acid ((R)-1,2,3,4-tetrahydronaphthalen-1-yl)-amide (epimer A) | see B.3 | E | 0.86 | 295.2 |
| Example 108 | 2,3-dihydrofuro[2,3-b]pyridine-3-carboxylic acid ((R)-1,2,3,4-tetrahydronaphthalen-1-yl)-amide (epimer B) | see B.3 | E | 0.85 | 295.2 |
| Example 109 | 2,3-Dihydro-furo[2,3-b]pyridine-3-carboxylic acid (7-chloro-indan-1-yl)-amide (enantiomer A of example 102) | see B.4 | E | 0.83 | 315.2 |
| Example 110 | 2,3-Dihydro-furo[2,3-b]pyridine-3-carboxylic acid (7-chloro-indan-1-yl)-amide (enantiomer B of example 102) | see B.4 | E | 0.83 | 315.2 |
| Example 111 | 2,3-Dihydro-furo[2,3-b]pyridine-3-carboxylic acid ((R)-8-chloro-1,2,3,4-tetrahydro-naphthalen-1-yl)-amide (epimer A) | see B.3 | E | 0.89 | 329.2 |

-continued

| Compound | Name | Purification method | LC-MS | $t_R$ [min] | $[M + H]^+$ |
|---|---|---|---|---|---|
| Example 112 | 2,3-Dihydro-furo[2,3-b]pyridine-3-carboxylic acid ((R)-8-chloro-1,2,3,4-tetrahydro-naphthalen-1-yl)-amide (epimer B) | see B.3 | E | 0.88 | 329.2 |
| Example 113 | 2,3-Dihydro-furo[2,3-b]pyridine-3-carboxylic acid (7-bromo-indan-1-yl)-amide (mixture of 4 stereoisomers) | L | E | 0.85 | 359.1 |
| Example 114 | rac-2,3-Dihydro-furo[2,3-b]pyridine-3-carboxylic acid 2,4,6-trichloro-benzylamide | L | E | 0.95 | 357.1 |
| Example 115 | rac-7-Oxy-2,3-dihydro-furo[2,3-b]pyridine-3-carboxylic acid 2,4-dichloro-6-methyl-benzylamide | precipitation from EtOAc | E | 0.78 | 353.2 |
| Example 116 | 2,3-Dihydro-furo[2,3-b]pyridine-3-carboxylic acid (5,7-dichloro-1-oxo-indan-2-yl)-amide (mixture of 4 stereoisomers) | M | E | 0.85 | 363.1 |
| Example 117 | rac-2,3-Dihydro-furo[2,3-b]pyridine-3-carboxylic acid 4-chloro-2-hydroxymethyl-benzylamide | N | E | 0.8 | 319.2 |
| Example 118 | rac-2,3-Dihydro-furo[2,3-b]pyridine-3-carboxylic acid 2-chloro-6-hydroxymethyl-benzylamide | N | E | 0.6 | 319.2 |

II. Biological Assays
In Vitro Assay

The $P2X_7$ receptor antagonistic activity of the compounds of formula (I) is determined in accordance with the following experimental method.

Experimental Method:
Cell Line Generation and YO-PRO Assay

Cell line generation was performed in general according to established molecular cloning protocols. Specifically, RNA was extracted from human whole blood using the Qiagen RNeasy kit (Qiagen, CH) according to the manufacturer's instructions. Subsequently cDNA was made (Superscript II, Invitrogen AG, CH) and the human P2X7 gene (genbank ref. BC011913) was amplified with the following primers: ATCGCGGCCGCTCAGTAAGGACTCTTGAAGCCACT (SEQ ID NO. 1) and CGCCGCTAGCACCACCATGCCGGCCTGCTGCAGCTGCA (SEQ ID NO. 2). The amplified sequence was subsequently ligated into a pcDNA3.1 (+) NotI, NheI digested plasmid. Human embryonic kidney (HEK) cells (ATCC CRL-1573, Manassas, Va., USA) were transfected with the pcDNA3.1 (+).hP2X7 plasmid using lipofectamine 2000 (Invitrogen AG, CH) according to the manufacturer's instructions. Following a 24 h exposure to DNA, cells were trypsinized and re-seeded at low density in the presence of 250 µg Geneticin. Geneticin resistant cells were then selected during two consecutive rounds of cloning by serial limiting dilution with visual inspection. Individual clones were screened for P2X7 expression by applying ATP and recording the resultant uptake of YO-PRO1. Specific cell clones were chosen based on RNA and protein expression. HEK cells stably expressing P2X7 were used to screen drugs using the YO-PRO1 assay. Cells were grown to confluency in adherent culture at 37° C. in a humidified 5% $CO_2$ incubator (split ⅓ every 3-4 days with DMEM, 10% FCS, 1% Penicillin/Streptomycin, 250 µg/ml Geneticin). Adherent cells were detached by incubation with Trypsine (1 ml per 165 $cm^2$ dish) for 2 minutes, then washed off with 10 ml PBS (without $Mg^{2+}$ and $Ca^{2+}$), and resuspended in DMEM, 10% FCS, 1% Penicillin/Streptomycin, no Geneticin. 10,000 cells per well (48 hours before the assay) or 25,000 cells per well (Vi-cell XR (Beckman Coulter) (24 hours before the assay) in 50 µl full medium were seeded on 384-well black-wall, clear bottom plates, that were coated before with 10 µl per well Poly-L-Lysine, incubated for 30-60 minutes at 37° C. and washed once with PBS. Medium was removed from cells and 50 µl of assay buffer containing 0.5 µM YO-PRO-1 was added into the wells. Solutions of antagonist compounds were prepared by serial dilutions of a 10 mM DMSO solution of the antagonist into PBS using a BioMek (Beckman Coulter). Each concentration was performed in duplicate. For $IC_{50}$ measurements 10 concentration points were measured (10 µM being the highest concentration followed by 9 serial dilution steps ⅓). The cells were incubated with the antagonists of the present invention together with ATP at a final concentration of 250 µM for 90 minutes. During this time period, four time points were taken. Each time point comprised the average of several measurements made within a few seconds. Fluorescence was measured in the FLIPR tetra (Molecular Devices) using the filters appropriate for YO-PRO-1 fluorescence (excitation485/20, emission 530/25). The FLIPR tetra was equipped with Molecular Devices Screen Works system control software to define and run experimental protocols. For antagonist activity measurements, the maximal intensity was expressed as a percentage of that induced by the $EC_{50}$ value for agonist activation (0.25 mM ATP for HEK-293 cells expressing human recombinant P2X7 receptor). For IC50 measurements the maximum intensity is plotted against the concentration of compound to determine IC50 values.

Antagonistic activities with respect to the $P2X_7$ receptor ($IC_{50}$ values) of exemplified compounds are displayed in Table 1.

TABLE 1

| Compound | Name | IC$_{50}$ [nM] |
|---|---|---|
| Example 1 | 2,3-Dihydro-furo[2,3-b]pyridine-3-carboxylic acid ((S)-1-cyclohexyl-2-hydroxy-ethyl)-amide (epimer A) | 1070 |
| Example 2 | 2,3-Dihydro-furo[2,3-b]pyridine-3-carboxylic acid ((S)-1-cyclohexyl-2-hydroxy-ethyl)-amide (epimer B) | 106 |
| Example 3 | 2,3-Dihydro-furo[2,3-b]pyridine-3-carboxylic acid 2,4-dichloro-6-methyl-benzylamide (enantiomer A) | 18.3 |
| Example 4 | 2,3-Dihydro-furo[2,3-b]pyridine-3-carboxylic acid 2,4-dichloro-6-methyl-benzylamide (enantiomer B) | 2.9 |
| Example 5 | rac-2,3-Dihydro-furo[2,3-b]pyridine-3-carboxylic acid 2,4-dichloro-benzylamide | 59.2 |
| Example 6 | 2,3-Dihydro-furo[2,3-b]pyridine-3-carboxylic acid [(S)-1-(2,4-dichloro-phenyl)-2-hydroxy-ethyl]-amide (epimer A) | 621 |
| Example 7 | 2,3-Dihydro-furo[2,3-b]pyridine-3-carboxylic acid [(S)-1-(2,4-dichloro-phenyl)-2-hydroxy-ethyl]-amide (epimer B) | 117 |
| Example 8 | (S)-3,4-Dihydro-2H-pyrano[2,3-b]pyridine-4-carboxylic acid ((S)-1-cyclohexyl-2-hydroxy-ethyl)-amide and (R)-3,4-Dihydro-2H-pyrano[2,3-b]pyridine-4-carboxylic acid ((S)-1-cyclohexyl-2-hydroxy-ethyl)-amide | 127 |
| Example 9 | (S)-3,4-Dihydro-2H-pyrano[2,3-b]pyridine-4-carboxylic acid [(S)-1-(2,4-dichloro-phenyl)-2-hydroxy-ethyl]-amide and (R)-3,4-Dihydro-2H-pyrano[2,3-b]pyridine-4-carboxylic acid [(S)-1-(2,4-dichloro-phenyl)-2-hydroxy-ethyl]-amide | 70.8 |
| Example 10 | rac-3,4-Dihydro-2H-pyrano[2,3-b]pyridine-4-carboxylic acid (1-hydroxy-cyclohexylmethyl)-amide | 3175 |
| Example 11 | rac-3-Fluoro-2,3-dihydro-furo[2,3-b]pyridine-3-carboxylic acid 2,4-dichloro-6-methyl-benzylamide | 4.8 |
| Example 12 | rac-4-Fluoro-3,4-dihydro-2H-pyrano[2,3-b]pyridine-4-carboxylic acid 2,4-dichloro-6-methyl-benzylamide | 3.1 |
| Example 13 | rac-2,3-Dihydro-furo[2,3-b]pyridine-3-carboxylic acid (1-cycloheptyl-2-hydroxy-ethyl)-amide (diastereoisomer A) | 813 |
| Example 14 | rac-2,3-Dihydro-furo[2,3-b]pyridine-3-carboxylic acid (1-cycloheptyl-2-hydroxy-ethyl)-amide (diastereoisomer B) | 117 |
| Example 15 | rac-2,3-Dihydro-furo[2,3-b]pyridine-3-carboxylic acid 2,4-dichloro-6-fluoro-benzylamide | 66.8 |
| Example 16 | rac-2,3-Dihydro-furo[2,3-b]pyridine-3-carboxylic acid 2-chloro-3-trifluoromethyl-benzylamide | 12.6 |
| Example 17 | 3,4-Dihydro-2H-pyrano[2,3-b]pyridine-4-carboxylic acid 2,4-dichloro-6-methyl-benzylamide (enantiomer A) | 1.3 |
| Example 18 | 3,4-Dihydro-2H-pyrano[2,3-b]pyridine-4-carboxylic acid 2,4-dichloro-6-methyl-benzylamide (enantiomer B) | 1.6 |
| Example 19 | rac-3,4-Dihydro-2H-pyrano[2,3-b]pyridine-4-carboxylic acid [1-(6-chloro-pyridin-3-yl)-cyclohexylmethyl]-amide | 6.3 |
| Example 20 | rac-3-Fluoro-2,3-dihydro-furo[2,3-b]pyridine-3-carboxylic acid 2,3-dichloro-benzylamide | 67.9 |
| Example 21 | rac-2,3-Dihydro-furo[2,3-b]pyridine-3-carboxylic acid 2,4-dichloro-6-cyclopropyl-benzylamide | 12.9 |
| Example 22 | rac-2,3-Dihydro-furo[2,3-b]pyridine-3-carboxylic acid 2,4-dichloro-6-ethyl-benzylamide | 1.5 |
| Example 23 | rac-2,3-Dihydro-furo[2,3-b]pyridine-3-carboxylic acid 2,4-dichloro-6-vinyl-benzylamide | 12.2 |
| Example 24 | 2,3-Dihydro-furo[2,3-b]pyridine-3-carboxylic acid 2,4-dichloro-6-hydroxymethyl-benzylamide (enantiomer A) | 39.4 |
| Example 25 | 2,3-Dihydro-furo[2,3-b]pyridine-3-carboxylic acid 2,4-dichloro-6-hydroxymethyl-benzylamide (enantiomer B) | 2.7 |
| Example 26 | rac-2,3-Dihydro-furo[2,3-b]pyridine-3-carboxylic acid 2,4-dichloro-6-methoxy-benzylamide | 25.6 |
| Example 27 | rac-2,3-Dihydro-furo[2,3-b]pyridine-3-carboxylic acid [2-(4,4-difluoro-piperidin-1-yl)-2-(2-methyl-pyrimidin-5-yl)-ethyl]-amide (diastereoisomer A) | 1363 |
| Example 28 | rac-2,3-Dihydro-furo[2,3-b]pyridine-3-carboxylic acid [2-(4,4-difluoro-piperidin-1-yl)-2-(2-methyl-pyrimidin-5-yl)-ethyl]-amide (diastereoisomer B) | 58.9 |
| Example 29 | rac-2,3-Dihydro-furo[2,3-b]pyridine-3-carboxylic acid [2-(2-methyl-pyrimidin-5-yl)-2-morpholin-4-yl-ethyl]-amide (diastereoisomer A) | 1685 |
| Example 30 | rac-2,3-Dihydro-furo[2,3-b]pyridine-3-carboxylic acid [2-(2-methyl-pyrimidin-5-yl)-2-morpholin-4-yl-ethyl]-amide (diastereoisomer B) | 225 |
| Example 31 | rac-3,4-Dihydro-2H-pyrano[2,3-b]pyridine-4-carboxylic acid 3-chloro-2-methyl-benzylamide | 16.0 |
| Example 32 | rac-3,4-Dihydro-2H-pyrano[2,3-b]pyridine-4-carboxylic acid 2-chloro-4-fluoro-benzylamide | 25.0 |
| Example 33 | rac-3,4-Dihydro-2H-pyrano[2,3-b]pyridine-4-carboxylic acid 4-phenoxy-benzylamide | 255 |
| Example 34 | rac-3,4-Dihydro-2H-pyrano[2,3-b]pyridine-4-carboxylic acid 2,3-dichloro-benzylamide | 10.7 |
| Example 35 | rac-3,4-Dihydro-2H-pyrano[2,3-b]pyridine-4-carboxylic acid 4-chloro-benzylamide | 475 |

TABLE 1-continued

| Compound | Name | IC$_{50}$ [nM] |
|---|---|---|
| Example 36 | rac-3,4-Dihydro-2H-pyrano[2,3-b]pyridine-4-carboxylic acid 4-trifluoromethyl-benzylamide | 334 |
| Example 37 | rac-3,4-Dihydro-2H-pyrano[2,3-b]pyridine-4-carboxylic acid (4-chloro-benzyl)-methyl-amide | 758 |
| Example 38 | rac-3,4-Dihydro-2H-pyrano[2,3-b]pyridine-4-carboxylic acid [2-(2,4-dichloro-phenyl)-ethyl]-amide | 67.1 |
| Example 39 | rac-3,4-Dihydro-2H-pyrano[2,3-b]pyridine-4-carboxylic acid 2,4-dichloro-benzylamide | 11.8 |
| Example 40 | rac-3,4-Dihydro-2H-pyrano[2,3-b]pyridine-4-carboxylic acid 2-chloro-3-trifluoromethyl-benzylamide | 2.7 |
| Example 41 | rac-8-Oxy-3,4-dihydro-2H-pyrano[2,3-b]pyridine-4-carboxylic acid 2,4-dichloro-6-methyl-benzylamide | 16.3 |
| Example 42 | rac-2,3-Dihydro-furo[2,3-b]pyridine-3-carboxylic acid 3-chloro-2-methyl-benzylamide | 46.9 |
| Example 43 | rac-2,3-Dihydro-furo[2,3-b]pyridine-3-carboxylic acid 2-chloro-4-fluoro-benzylamide | 86.8 |
| Example 44 | rac-2,3-Dihydro-furo[2,3-b]pyridine-3-carboxylic acid 4-phenoxy-benzylamide | 1117 |
| Example 45 | rac-2,3-Dihydro-furo[2,3-b]pyridine-3-carboxylic acid 2,3-dichloro-benzylamide | 37.2 |
| Example 46 | rac-2,3-Dihydro-furo[2,3-b]pyridine-3-carboxylic acid 4-chloro-benzylamide | 795 |
| Example 47 | rac-2,3-Dihydro-furo[2,3-b]pyridine-3-carboxylic acid 4-trifluoromethyl-benzylamide | 1248 |
| Example 48 | rac-2,3-Dihydro-furo[2,3-b]pyridine-3-carboxylic acid (4-chloro-benzyl)-methyl-amide | 1087 |
| Example 49 | rac-2,3-Dihydro-furo[2,3-b]pyridine-3-carboxylic acid [2-(2,4-dichloro-phenyl)-ethyl]-amide | 157 |
| Example 50 | rac-2,3-Dihydro-furo[2,3-b]pyridine-3-carboxylic acid 2,4-dichloro-6-(2-hydroxy-ethoxy)-benzylamide | 54.6 |
| Example 51 | rac-3,4-Dihydro-2H-pyrano[2,3-b]pyridine-4-carboxylic acid 2,4-dichloro-6-hydroxymethyl-benzylamide | 5.6 |
| Example 52 | 3,4-Dihydro-2H-pyrano[2,3-b]pyridine-4-carboxylic acid (1-cycloheptyl-2-hydroxy-ethyl)-amide (mixture of 4 stereoisomers) | 276 |
| Example 53 | rac-3,4-Dihydro-2H-pyrano[2,3-b]pyridine-4-carboxylic acid 3-fluoro-4-trifluoromethoxy-benzylamide | 1185 |
| Example 54 | rac-3,4-Dihydro-2H-pyrano[2,3-b]pyridine-4-carboxylic acid (1-phenyl-cyclohexylmethyl)-amide | 25.8 |
| Example 55 | rac-3-Fluoro-2,3-dihydro-furo[2,3-b]pyridine-3-carboxylic acid 2-chloro-3-trifluoromethyl-benzylamide | 41.6 |
| Example 56 | rac-2,3-Dihydro-furo[2,3-b]pyridine-3-carboxylic acid 2-chloro-3-cyano-benzylamide | 125 |
| Example 57 | rac-2,3-Dihydro-furo[2,3-b]pyridine-3-carboxylic acid 3-fluoro-4-trifluoromethoxy-benzylamide | 3065 |
| Example 58 | rac-3,4-Dihydro-2H-pyrano[2,3-b]pyridine-4-carboxylic acid [1-(2,4-dichloro-phenyl)-cyclopropyl]-amide | 2700 |
| Example 59 | rac-2,3-Dihydro-furo[2,3-b]pyridine-3-carboxylic acid [2-morpholin-4-yl-2-(2-trifluoromethyl-pyrimidin-5-yl)-ethyl]-amide (diastereoisomer A) | 346 |
| Example 60 | rac-2,3-Dihydro-furo[2,3-b]pyridine-3-carboxylic acid [2-morpholin-4-yl-2-(2-trifluoromethyl-pyrimidin-5-yl)-ethyl]-amide (diastereoisomer B) | 29.0 |
| Example 61 | rac-2,3-Dihydro-furo[2,3-b]pyridine-3-carboxylic acid 2-chloro-4-cyano-benzylamide | 389 |
| Example 62 | 2,3-Dihydro-furo[2,3-b]pyridine-3-carboxylic acid [2-(4,4-difluoro-piperidin-1-yl)-2-(2-trifluoromethyl-pyrimidin-5-yl)-ethyl]-amide (mixture of 4 stereoisomers) | 46.9 |
| Example 63 | rac-2,3-Dihydro-furo[2,3-b]pyridine-3-carboxylic acid (1-carbamoyl-cyclopentyl)-amide | 3850 |
| Example 64 | 2,3-Dihydro-furo[2,3-b]pyridine-3-carboxylic acid (2-phenyl-cyclopropyl)-amide (mixture of 4 stereoisomers) | 4850 |
| Example 65 | (S)-2,3-Dihydro-furo[2,3-b]pyridine-3-carboxylic acid ((1S,2R)-2-hydroxy-indan-1-yl)-amide and (R)-2,3-Dihydro-furo[2,3-b]pyridine-3-carboxylic acid ((1S,2R)-2-hydroxy-indan-1-yl)-amide | 3400 |
| Example 66 | 2,3-Dihydro-furo[2,3-b]pyridine-3-carboxylic acid (2-carbamoyl-cyclohexyl)-amide (mixture of 4 stereoisomers) | 5880 |
| Example 67 | rac-3,4-Dihydro-2H-pyrano[2,3-b]pyridine-4-carboxylic acid (1-(6-chloropyridin-3-yl)-4,4-difluorocyclohexylmethyl)-amide | 7.3 |
| Example 68 | rac-2,3-Dihydro-furo[2,3-b]pyridine-3-carboxylic acid 2,4-dichloro-6-trifluoromethyl-benzylamide | 13.8 |
| Example 69 | (S)-2,3-Dihydro-furo[2,3-b]pyridine-3-carboxylic acid (R)-indan-1-ylamide and (R)-2,3-Dihydro-furo[2,3-b])pyridine-3-carboxylic acid (R)-indan-1-ylamide | 400 |
| Example 70 | 2,3-Dihydro-furo[2,3-b]pyridine-3-carboxylic acid [(R)-1-(2,4-dichloro-phenyl)-ethyl]-amide (epimer A) | 110 |

TABLE 1-continued

| Compound | Name | IC$_{50}$ [nM] |
|---|---|---|
| Example 71 | 2,3-Dihydro-furo[2,3-b]pyridine-3-carboxylic acid [(R)-1-(2,4-dichloro-phenyl)-ethyl]-amide (epimer B) | 36.5 |
| Example 72 | rac-2,3-Dihydro-furo[2,3-b]pyridine-3-carboxylic acid 2,4-dichloro-6-methoxymethyl-benzylamide | 14.6 |
| Example 73 | rac-2,3-Dihydro-furo[2,3-b]pyridine-3-carboxylic acid 3-chloro-2-trifluoromethyl-benzylamide | 20.2 |
| Example 74 | rac-2,3-Dihydro-furo[2,3-b]pyridine-3-carboxylic acid [2-(6-chloro-pyridin-3-yl)-2-(4,4-difluoro-piperidin-1-yl)-ethyl]-amide (diastereoisomer A) | 120 |
| Example 75 | rac-2,3-Dihydro-furo[2,3-b]pyridine-3-carboxylic acid [2-(6-chloro-pyridin-3-yl)-2-(4,4-difluoro-piperidin-1-yl)-ethyl]-amide (diastereoisomer B) | 35.3 |
| Example 76 | rac-2,3-Dihydro-furo[2,3-b]pyridine-3-carboxylic acid (5,7-dichloro-indan-1-yl)-amide (diastereoisomer A) | 20.6 |
| Example 77 | rac-2,3-Dihydro-furo[2,3-b]pyridine-3-carboxylic acid (5,7-dichloro-indan-1-yl)-amide (diastereoisomer B) | 4.7 |
| Example 78 | 2,3-Dihydro-furo[2,3-b]pyridine-3-carboxylic acid [2-(4,4-difluoro-piperidin-1-yl)-2-(4-trifluoromethyl-phenyl)-ethyl]-amide (mixture of 4 stereoisomers) | 122 |
| Example 79 | 2,3-Dihydro-furo[2,3-b]pyridine-3-carboxylic acid 2-bromo-4,6-dichloro-benzylamide (enantiomer A) | 51.1 |
| Example 80 | 2,3-Dihydro-furo[2,3-b]pyridine-3-carboxylic acid 2-bromo-4,6-dichloro-benzylamide (enantiomer B) | 4.1 |
| Example 81 | 2,3-Dihydro-furo[2,3-b]pyridine-3-carboxylic acid [2-morpholin-4-yl-2-(2-trifluoromethyl-pyrimidin-5-yl)-ethyl]-amide (isomer A) | 7523 |
| Example 82 | 2,3-Dihydro-furo[2,3-b]pyridine-3-carboxylic acid [2-morpholin-4-yl-2-(2-trifluoromethyl-pyrimidin-5-yl)-ethyl]-amide (isomer B) | 2230 |
| Example 83 | 2,3-Dihydro-furo[2,3-b]pyridine-3-carboxylic acid [2-morpholin-4-yl-2-(2-trifluoromethyl-pyrimidin-5-yl)-ethyl]-amide (isomer C) | 124 |
| Example 84 | 2,3-Dihydro-furo[2,3-b]pyridine-3-carboxylic acid [2-morpholin-4-yl-2-(2-trifluoromethyl-pyrimidin-5-yl)-ethyl]-amide (isomer D) | 20.8 |
| Example 85 | 2,3-Dihydro-furo[2,3-b]pyridine-3-carboxylic acid (5,7-dichloro-indan-1-yl)-amide (enantiomer A of example 76) | 9.5 |
| Example 86 | 2,3-Dihydro-furo[2,3-b]pyridine-3-carboxylic acid (5,7-dichloro-indan-1-yl)-amide (enantiomer B of example 76) | 164 |
| Example 87 | 2,3-Dihydro-furo[2,3-b]pyridine-3-carboxylic acid [2-(6-methoxy-pyridin-3-yl)-2-morpholin-4-yl-ethyl]-amide (mixture of 4 stereoisomers) | 978 |
| Example 88 | rac-2,3-Dihydro-furo[2,3-b]pyridine-3-carboxylic acid (3-oxo-indan-1-yl)-amide (diastereoisomer A) | 1450 |
| Example 89 | rac-2,3-Dihydro-furo[2,3-b]pyridine-3-carboxylic acid (3-oxo-indan-1-yl)-amide (diastereoisomer B) | 2508 |
| Example 90 | 2,3-Dihydro-furo[2,3-b]pyridine-3-carboxylic acid [2-(6-methyl-pyridin-3-yl)-2-morpholin-4-yl-ethyl]-amide (mixture of 4 stereoisomers) | 1149 |
| Example 91 | 2,3-Dihydro-furo[2,3-b]pyridine-3-carboxylic acid [2-(2-cyclopropyl-pyrimidin-5-yl)-2-morpholin-4-yl-ethyl]-amide (mixture of 4 stereoisomers) | 215 |
| Example 92 | 2,3-Dihydro-furo[2,3-b]pyridine-3-carboxylic acid [2-morpholin-4-yl-2-(6-trifluoromethyl-pyridin-3-yl)-ethyl]-amide (mixture of 4 stereoisomers) | 82.2 |
| Example 93 | rac-2,3-Dihydro-furo[2,3-b]pyridine-3-carboxylic acid 2,4-dichloro-6-(2-hydroxy-ethoxymethyl)-benzylamide | 11.4 |
| Example 94 | rac-2,3-Dihydro-furo[2,3-b]pyridine-3-carboxylic acid (4,6-dichloro-indan-1-yl)-amide (diastereoisomer A) | 570 |
| Example 95 | rac-2,3-Dihydro-furo[2,3-b]pyridine-3-carboxylic acid (4,6-dichloro-indan-1-yl)-amide (diastereoisomer B) | 978 |
| Example 96 | rac-2,3-Dihydro-furo[2,3-b]pyridine-3-carboxylic acid 2,4-dichloro-6-trideuteromethyl-benzylamide | 2.7 |
| Example 97 | 2,3-Dihydro-furo[2,3-b]pyridine-3-carboxylic acid 2,4-dichloro-6-trideuteromethyl-benzylamide (enantiomer A) | 20 |
| Example 98 | 2,3-Dihydro-furo[2,3-b]pyridine-3-carboxylic acid 2,4-dichloro-6-trideuteromethyl-benzylamide (enantiomer B) | 1.8 |
| Example 99 | rac-2,3-Dihydro-furo[2,3-b]pyridine-3-carboxylic acid (5-chloro-indan-1-yl)-amide (diastereoisomer A) | 301 |
| Example 100 | rac-2,3-Dihydro-furo[2,3-b]pyridine-3-carboxylic acid (5-chloro-indan-1-yl)-amide (diastereoisomer B) | 59.9 |
| Example 101 | rac-2,3-Dihydro-furo[2,3-b]pyridine-3-carboxylic acid (7-chloro-indan-1-yl)-amide (diastereoisomer A) | 212 |
| Example 102 | rac-2,3-Dihydro-furo[2,3-b]pyridine-3-carboxylic acid (7-chloro-indan-1-yl)-amide (diastereoisomer B) | 11.0 |
| Example 103 | rac-2,3-Dihydro-furo[2,3-b]pyridine-3-carboxylic acid 2-chloro-4-trifluoromethyl-benzylamide | 80.4 |

TABLE 1-continued

| Compound | Name | IC$_{50}$ [nM] |
|---|---|---|
| Example 104 | 2,3-Dihydro-furo[2,3-b]pyridine-3-carboxylic acid (5,7-dichloro-indan-1-yl)-amide (enantiomer A of example 77) | 5100 |
| Example 105 | 2,3-Dihydro-furo[2,3-b]pyridine-3-carboxylic acid (5,7-dichloro-indan-1-yl)-amide (enantiomer B of example 77) | 1.3 |
| Example 106 | rac-2,3-Dihydro-furo[2,3-b]pyridine-3-carboxylic acid [3-(2,4-dichloro-phenyl)-propyl]-amide | 346 |
| Example 107 | 2,3-dihydrofuro[2,3-b]pyridine-3-carboxylic acid ((R)-1,2,3,4-tetrahydronaphthalen-1-yl)-amide (epimer A) | 1222 |
| Example 108 | 2,3-dihydrofuro[2,3-b]pyridine-3-carboxylic acid ((R)-1,2,3,4-tetrahydronaphthalen-1-yl)-amide (epimer B) | 191 |
| Example 109 | 2,3-Dihydro-furo[2,3-b]pyridine-3-carboxylic acid (7-chloro-indan-1-yl)-amide (enantiomer A of example 102) | 10000 |
| Example 110 | 2,3-Dihydro-furo[2,3-b]pyridine-3-carboxylic acid (7-chloro-indan-1-yl)-amide (enantiomer B of example 102) | 5.5 |
| Example 111 | 2,3-Dihydro-furo[2,3-b]pyridine-3-carboxylic acid ((R)-8-chloro-1,2,3,4-tetrahydro-naphthalen-1-yl)-amide (epimer A) | 221 |
| Example 112 | 2,3-Dihydro-furo[2,3-b]pyridine-3-carboxylic acid ((R)-8-chloro-1,2,3,4-tetrahydro-naphthalen-1-yl)-amide (epimer B) | 9.5 |
| Example 113 | 2,3-Dihydro-furo[2,3-b]pyridine-3-carboxylic acid (7-bromo-indan-1-yl)-amide (mixture of 4 stereoisomers) | 35.9 |
| Example 114 | rac-2,3-Dihydro-furo[2,3-b]pyridine-3-carboxylic acid 2,4,6-trichloro-benzylamide | 12.5 |
| Example 115 | rac-7-Oxy-2,3-dihydro-furo[2,3-b]pyridine-3-carboxylic acid 2,4-dichloro-6-methyl-benzylamide | 35.4 |
| Example 116 | 2,3-Dihydro-furo[2,3-b]pyridine-3-carboxylic acid (5,7-dichloro-1-oxo-indan-2-yl)-amide (mixture of 4 stereoisomers) | 9010 |
| Example 117 | rac-2,3-Dihydro-furo[2,3-b]pyridine-3-carboxylic acid 4-chloro-2-hydroxymethyl-benzylamide | 1487 |
| Example 118 | rac-2,3-Dihydro-furo[2,3-b]pyridine-3-carboxylic acid 2-chloro-6-hydroxymethyl-benzylamide | 304 |

The invention claimed is:
1. A compound of the formula (I),

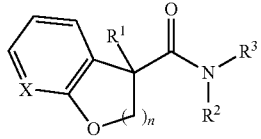

(I)

wherein
n represents 1 or 2;
X represents —N— or —N(O)—;
$R^1$ represents hydrogen or halogen;
$R^2$ represents hydrogen or methyl; and
$R^3$ represents
 aryl-$(C_1$-$C_3)$alkyl, which is in the alkyl part optionally mono-substituted with hydroxy or heterocyclyl; and which is in the aryl part mono-, di- or tri-substituted, wherein the substituents are independently selected from the group consisting of $(C_1$-$C_4)$alkyl, $(C_2$-$C_4)$alkenyl, $(C_3$-$C_6)$cycloalkyl, $(C_1$-$C_4)$alkoxy, hydroxy-$(C_1$-$C_3)$alkyl, hydroxy-$(C_2$-$C_3)$alkoxy, hydroxy-$(C_2$-$C_3)$alkoxy-$(C_1$-$C_2)$alkyl, $(C_1$-$C_2)$alkoxy-$(C_1$-$C_2)$alkyl, $(C_1$-$C_3)$fluoroalkyl, $(C_1$-$C_3)$fluoroalkoxy, cyano, halogen and phenoxy; or
 heteroaryl-$(C_1$-$C_3)$alkyl, which is in the alkyl part mono-substituted with heterocyclyl; and which is in the heteroaryl part mono-, di- or tri-substituted, wherein the substituents are independently selected from the group consisting of $(C_1$-$C_4)$alkyl, $(C_3$-$C_6)$cycloalkyl, $(C_1$-$C_4)$alkoxy, $(C_1$-$C_3)$fluoroalkyl and halogen;
 or
 $(C_3$-$C_7)$cycloalkyl, which is monosubstituted with —C(O)NH$_2$ or an optionally mono-, di- or tri-substituted phenyl, wherein the substituents are selected from halogen; or
 $(C_5$-$C_7)$cycloalkyl, which is optionally mono-substituted with hydroxy or oxo; and which is annelated with an optionally mono-, di- or tri-substituted phenyl, wherein the substituents are selected from halogen; or
 $(C_3$-$C_7)$cycloalkyl-$(C_1$-$C_3)$alkyl, which is in the alkyl part optionally mono-substituted with hydroxy; and which is in the cycloalkyl part optionally di-substituted with halogen and optionally mono-substituted with hydroxy, aryl or heteroaryl, wherein the aryl or heteroaryl groups are optionally mono-, di- or tri-substituted with halogen;
or a salt of such a compound.
2. A compound of formula (I) according to claim 1, wherein
n represents 1 or 2;
X represents —N— or —N(O)—;
$R^1$ represents hydrogen or fluorine;
$R^2$ represents hydrogen; and
$R^3$ represents
 aryl-methyl, which is in the aryl part di- or tri-substituted, wherein the substituents are independently selected from the group consisting of $(C_1$-$C_4)$alkyl, $(C_2$-$C_4)$alkenyl, $(C_3$-$C_6)$cycloalkyl, $(C_1$-$C_4)$alkoxy, hydroxy-$(C_1$-$C_3)$alkyl, hydroxy-$(C_2$-$C_3)$alkoxy-$(C_1$-$C_2)$alkyl, $(C_1$-$C_2)$alkoxy-$(C_1$-$C_2)$alkyl, $(C_1$-$C_3)$fluoroalkyl and halogen; or
 cyclopentyl, which is annelated with an mono- or di-substituted phenyl, wherein the substituents are selected from halogen; or
 cyclohexyl-methyl, which is in the cyclohexyl part optionally di-substituted with fluorine and mono-substituted with aryl or heteroaryl, wherein the aryl or heteroaryl groups are optionally mono- or di-substituted with halogen;
or a salt of such a compound.
3. A compound of formula (I) according to claim 1, wherein n represents 1; or a salt of such a compound.
4. A compound of formula (I) according to claim 1, wherein n represents 2; or a salt of such a compound.
5. A compound of formula (I) according claim 1, wherein X represents —N—; or a salt of such a compound.
6. A compound of formula (I) according to claim 1, wherein $R^2$ represents hydrogen; or a salt of such a compound.
7. A compound of formula (I) according to claim 1, wherein $R^3$ represents
 aryl-$(C_1$-$C_2)$alkyl, which is in the aryl part mono-, di- or tri-substituted, wherein the substituents are independently selected from the group consisting of $(C_1$-$C_4)$alkyl, $(C_2$-$C_4)$alkenyl, $(C_3$-$C_6)$cycloalkyl, $(C_1$-$C_4)$alkoxy, hydroxy-$(C_1$-$C_3)$alkyl, hydroxy-$(C_2$-$C_3)$alkoxy-$(C_1$-$C_2)$alkyl, $(C_1$-$C_2)$alkoxy-$(C_1$-$C_2)$alkyl, $(C_1$-$C_3)$fluoroalkyl and halogen; or
 $(C_5$-$C_7)$cycloalkyl, which is annelated with an optionally mono-, di- or tri-substituted phenyl, wherein the substituents are selected from halogen; or
 $(C_5$-$C_7)$cycloalkyl-$(C_1$-$C_2)$alkyl, which is in the cycloalkyl part optionally di-substituted with halogen and mono-substituted with aryl or heteroaryl, wherein the aryl or heteroaryl groups are optionally mono- or di-substituted with halogen;
or a salt of such a compound.
8. A compound of formula (I) according to claim 1, wherein $R^3$ represents
 aryl-methyl, which is in the aryl part di- or tri-substituted, wherein the substituents are independently selected from the group consisting of $(C_1$-$C_4)$alkyl, $(C_2$-$C_4)$alkenyl, $(C_3$-$C_6)$cycloalkyl, $(C_1$-$C_4)$alkoxy, hydroxy-$(C_1$-$C_3)$alkyl, hydroxy-$(C_2$-$C_3)$alkoxy-$(C_1$-$C_2)$alkyl, $(C_1$-$C_2)$alkoxy-$(C_1$-$C_2)$alkyl, $(C_1$-$C_3)$fluoroalkyl and halogen; or
 cyclopentyl, which is annelated with an mono- or di-substituted phenyl, wherein the substituents are selected from halogen; or
 cyclohexyl-methyl, which is in the cyclohexyl part optionally di-substituted with fluorine and mono-substituted with aryl or heteroaryl, wherein the aryl or heteroaryl groups are optionally mono- or di-substituted with halogen;
or a salt of such a compound.
9. A compound of formula (I) according to claim 1, selected from the group consisting of:
 (S)-2,3-Dihydro-furo[2,3-b]pyridine-3-carboxylic acid ((S)-1-cyclohexyl-2-hydroxy-ethyl)-amide;
 (R)-2,3-Dihydro-furo[2,3-b]pyridine-3-carboxylic acid ((S)-1-cyclohexyl-2-hydroxy-ethyl)-amide;
 (S)-2,3-Dihydro-furo[2,3-b]pyridine-3-carboxylic acid 2,4-dichloro-6-methyl-benzylamide;
 (R)-2,3-Dihydro-furo[2,3-b]pyridine-3-carboxylic acid 2,4-dichloro-6-methyl-benzylamide;
 2,3-Dihydro-furo[2,3-b]pyridine-3-carboxylic acid 2,4-dichloro-benzylamide;

(S)-2,3-Dihydro-furo[2,3-b]pyridine-3-carboxylic acid [(S)-1-(2,4-dichloro-phenyl)-2-hydroxy-ethyl]-amide;
(R)-2,3-Dihydro-furo[2,3-b]pyridine-3-carboxylic acid [(S)-1-(2,4-dichloro-phenyl)-2-hydroxy-ethyl]-amide;
3,4-Dihydro-2H-pyrano[2,3-b]pyridine-4-carboxylic acid ((S)-1-cyclohexyl-2-hydroxy-ethyl)-amide;
3,4-Dihydro-2H-pyrano[2,3-b]pyridine-4-carboxylic acid [(S)-1-(2,4-dichloro-phenyl)-2-hydroxy-ethyl]-amide;
3,4-Dihydro-2H-pyrano[2,3-b]pyridine-4-carboxylic acid (1-hydroxy-cyclohexylmethyl)-amide;
3-Fluoro-2,3-dihydro-furo[2,3-b]pyridine-3-carboxylic acid 2,4-dichloro-6-methyl-benzylamide;
4-Fluoro-3,4-dihydro-2H-pyrano[2,3-b]pyridine-4-carboxylic acid 2,4-dichloro-6-methyl-benzylamide;
(S*)-2,3-Dihydro-furo[2,3-b]pyridine-3-carboxylic acid ((S*)-1-cycloheptyl-2-hydroxy-ethyl)-amide;
(S*)-2,3-Dihydro-furo[2,3-b]pyridine-3-carboxylic acid ((R*)-1-cycloheptyl-2-hydroxy-ethyl)-amide;
2,3-Dihydro-furo[2,3-b]pyridine-3-carboxylic acid 2,4-dichloro-6-fluoro-benzylamide;
2,3-Dihydro-furo[2,3-b]pyridine-3-carboxylic acid 2-chloro-3-trifluoromethyl-benzylamide;
(S)-3,4-Dihydro-2H-pyrano[2,3-b]pyridine-4-carboxylic acid 2,4-dichloro-6-methyl-benzylamide;
(R)-3,4-Dihydro-2H-pyrano[2,3-b]pyridine-4-carboxylic acid 2,4-dichloro-6-methyl-benzylamide;
3,4-Dihydro-2H-pyrano[2,3-b]pyridine-4-carboxylic acid [1-(6-chloro-pyridin-3-yl)-cyclohexylmethyl]-amide;
3-Fluoro-2,3-dihydro-furo[2,3-b]pyridine-3-carboxylic acid 2,3-dichloro-benzylamide;
2,3-Dihydro-furo[2,3-b]pyridine-3-carboxylic acid 2,4-dichloro-6-cyclopropyl-benzylamide;
2,3-Dihydro-furo[2,3-b]pyridine-3-carboxylic acid 2,4-dichloro-6-ethyl-benzylamide;
2,3-Dihydro-furo[2,3-b]pyridine-3-carboxylic acid 2,4-dichloro-6-vinyl-benzylamide;
(S)-2,3-Dihydro-furo[2,3-b]pyridine-3-carboxylic acid 2,4-dichloro-6-hydroxymethyl-benzylamide;
(R)-2,3-Dihydro-furo[2,3-b]pyridine-3-carboxylic acid 2,4-dichloro-6-hydroxymethyl-benzylamide;
2,3-Dihydro-furo[2,3-b]pyridine-3-carboxylic acid 2,4-dichloro-6-methoxy-benzylamide;
(S*)-2,3-Dihydro-furo[2,3-b]pyridine-3-carboxylic acid [(S*)-2-(4,4-difluoro-piperidin-1-yl)-2-(2-methyl-pyrimidin-5-yl)-ethyl]-amide;
(S*)-2,3-Dihydro-furo[2,3-b]pyridine-3-carboxylic acid [(R*)-2-(4,4-difluoro-piperidin-1-yl)-2-(2-methyl-pyrimidin-5-yl)-ethyl]-amide;
(S*)-2,3-Dihydro-furo[2,3-b]pyridine-3-carboxylic acid [(S*)-2-(2-methyl-pyrimidin-5-yl)-2-morpholin-4-yl-ethyl]-amide;
(S*)-2,3-Dihydro-furo[2,3-b]pyridine-3-carboxylic acid [(R*)-2-(2-methyl-pyrimidin-5-yl)-2-morpholin-4-yl-ethyl]-amide;
3,4-Dihydro-2H-pyrano[2,3-b]pyridine-4-carboxylic acid 3-chloro-2-methyl-benzylamide;
3,4-Dihydro-2H-pyrano[2,3-b]pyridine-4-carboxylic acid 2-chloro-4-fluoro-benzylamide;
3,4-Dihydro-2H-pyrano[2,3-b]pyridine-4-carboxylic acid 4-phenoxy-benzylamide;
3,4-Dihydro-2H-pyrano[2,3-b]pyridine-4-carboxylic acid 2,3-dichloro-benzylamide;
3,4-Dihydro-2H-pyrano[2,3-b]pyridine-4-carboxylic acid 4-chloro-benzylamide;
3,4-Dihydro-2H-pyrano[2,3-b]pyridine-4-carboxylic acid 4-trifluoromethyl-benzylamide;
3,4-Dihydro-2H-pyrano[2,3-b]pyridine-4-carboxylic acid (4-chloro-benzyl)-methyl-amide;
3,4-Dihydro-2H-pyrano[2,3-b]pyridine-4-carboxylic acid [2-(2,4-dichloro-phenyl)-ethyl]-amide;
3,4-Dihydro-2H-pyrano[2,3-b]pyridine-4-carboxylic acid 2,4-dichloro-benzylamide;
3,4-Dihydro-2H-pyrano[2,3-b]pyridine-4-carboxylic acid 2-chloro-3-trifluoromethyl-benzylamide;
8-Oxy-3,4-dihydro-2H-pyrano[2,3-b]pyridine-4-carboxylic acid 2,4-dichloro-6-methyl-benzylamide;
2,3-Dihydro-furo[2,3-b]pyridine-3-carboxylic acid 3-chloro-2-methyl-benzylamide;
2,3-Dihydro-furo[2,3-b]pyridine-3-carboxylic acid 2-chloro-4-fluoro-benzylamide;
2,3-Dihydro-furo[2,3-b]pyridine-3-carboxylic acid 4-phenoxy-benzylamide;
2,3-Dihydro-furo[2,3-b]pyridine-3-carboxylic acid 2,3-dichloro-benzylamide;
2,3-Dihydro-furo[2,3-b]pyridine-3-carboxylic acid 4-chloro-benzylamide;
2,3-Dihydro-furo[2,3-b]pyridine-3-carboxylic acid 4-trifluoromethyl-benzylamide;
2,3-Dihydro-furo[2,3-b]pyridine-3-carboxylic acid (4-chloro-benzyl)-methyl-amide;
2,3-Dihydro-furo[2,3-b]pyridine-3-carboxylic acid [2-(2,4-dichloro-phenyl)-ethyl]-amide;
2,3-Dihydro-furo[2,3-b]pyridine-3-carboxylic acid 2,4-dichloro-6-(2-hydroxy-ethoxy)-benzylamide;
3,4-Dihydro-2H-pyrano[2,3-b]pyridine-4-carboxylic acid 2,4-dichloro-6-hydroxymethyl-benzylamide;
3,4-Dihydro-2H-pyrano[2,3-b]pyridine-4-carboxylic acid (1-cycloheptyl-2-hydroxy-ethyl)-amide;
3,4-Dihydro-2H-pyrano[2,3-b]pyridine-4-carboxylic acid 3-fluoro-4-trifluoromethoxy-benzylamide;
3,4-Dihydro-2H-pyrano[2,3-b]pyridine-4-carboxylic acid (1-phenyl-cyclohexylmethyl)-amide;
3-Fluoro-2,3-dihydro-furo[2,3-b]pyridine-3-carboxylic acid 2-chloro-3-trifluoromethyl-benzylamide;
2,3-Dihydro-furo[2,3-b]pyridine-3-carboxylic acid 2-chloro-3-cyano-benzylamide;
2,3-Dihydro-furo[2,3-b]pyridine-3-carboxylic acid 3-fluoro-4-trifluoromethoxy-benzylamide;
3,4-Dihydro-2H-pyrano[2,3-b]pyridine-4-carboxylic acid [1-(2,4-dichloro-phenyl)-cyclopropyl]-amide;
(S*)-2,3-Dihydro-furo[2,3-b]pyridine-3-carboxylic acid [(S*)-2-morpholin-4-yl-2-(2-trifluoromethyl-pyrimidin-5-yl)-ethyl]-amide;
(S*)-2,3-Dihydro-furo[2,3-b]pyridine-3-carboxylic acid [(R*)-2-morpholin-4-yl-2-(2-trifluoromethyl-pyrimidin-5-yl)-ethyl]-amide;
2,3-Dihydro-furo[2,3-b]pyridine-3-carboxylic acid 2-chloro-4-cyano-benzylamide;
2,3-Dihydro-furo[2,3-b]pyridine-3-carboxylic acid [2-(4,4-difluoro-piperidin-1-yl)-2-(2-trifluoromethyl-pyrimidin-5-yl)-ethyl]-amide;
2,3-Dihydro-furo[2,3-b]pyridine-3-carboxylic acid (1-carbamoyl-cyclopentyl)-amide;
2,3-Dihydro-furo[2,3-b]pyridine-3-carboxylic acid (2-phenyl-cyclopropyl)-amide;
2,3-Dihydro-furo[2,3-b]pyridine-3-carboxylic acid ((1S,2R)-2-hydroxy-indan-1-yl)-amide;
2,3-Dihydro-furo[2,3-b]pyridine-3-carboxylic acid (2-carbamoyl-cyclohexyl)-amide;
3,4-Dihydro-2H-pyrano[2,3-b]pyridine-4-carboxylic acid (1-(6-chloropyridin-3-yl)-4,4-difluorocyclohexylmethyl)-amide;

2,3-Dihydro-furo[2,3-b]pyridine-3-carboxylic acid 2,4-dichloro-6-trifluoromethyl-benzylamide;
2,3-Dihydro-furo[2,3-b]pyridine-3-carboxylic acid (R)-indan-1-ylamide;
(S)-2,3-Dihydro-furo[2,3-b]pyridine-3-carboxylic acid [(R)-1-(2,4-dichloro-phenyl)-ethyl]-amide;
(R)-2,3-Dihydro-furo[2,3-b]pyridine-3-carboxylic acid [(R)-1-(2,4-dichloro-phenyl)-ethyl]-amide;
2,3-Dihydro-furo[2,3-b]pyridine-3-carboxylic acid 2,4-dichloro-6-methoxymethyl-benzylamide;
2,3-Dihydro-furo[2,3-b]pyridine-3-carboxylic acid 3-chloro-2-trifluoromethyl-benzylamide;
(S*)-2,3-Dihydro-furo[2,3-b]pyridine-3-carboxylic acid [(S*)-2-(6-chloro-pyridin-3-yl)-2-(4,4-difluoro-piperidin-1-yl)-ethyl]-amide;
(S*)-2,3-Dihydro-furo[2,3-b]pyridine-3-carboxylic acid [(R*)-2-(6-chloro-pyridin-3-yl)-2-(4,4-difluoro-piperidin-1-yl)-ethyl]-amide;
(S*)-2,3-Dihydro-furo[2,3-b]pyridine-3-carboxylic acid ((S*)-5,7-dichloro-indan-1-yl)-amide;
(S*)-2,3-Dihydro-furo[2,3-b]pyridine-3-carboxylic acid ((R*)-5,7-dichloro-indan-1-yl)-amide;
2,3-Dihydro-furo[2,3-b]pyridine-3-carboxylic acid [2-(4,4-difluoro-piperidin-1-yl)-2-(4-trifluoromethyl-phenyl)-ethyl]-amide;
(S)-2,3-Dihydro-furo[2,3-b]pyridine-3-carboxylic acid 2-bromo-4,6-dichloro-benzylamide;
(R)-2,3-Dihydro-furo[2,3-b]pyridine-3-carboxylic acid 2-bromo-4,6-dichloro-benzylamide;
(S)-2,3-Dihydro-furo[2,3-b]pyridine-3-carboxylic acid [(S)-2-morpholin-4-yl-2-(2-trifluoromethyl-pyrimidin-5-yl)-ethyl]-amide;
(S)-2,3-Dihydro-furo[2,3-b]pyridine-3-carboxylic acid [(R)-2-morpholin-4-yl-2-(2-trifluoromethyl-pyrimidin-5-yl)-ethyl]-amide;
(R)-2,3-Dihydro-furo[2,3-b]pyridine-3-carboxylic acid [(S)-2-morpholin-4-yl-2-(2-trifluoromethyl-pyrimidin-5-yl)-ethyl]-amide;
(R)-2,3-Dihydro-furo[2,3-b]pyridine-3-carboxylic acid [(R)-2-morpholin-4-yl-2-(2-trifluoromethyl-pyrimidin-5-yl)-ethyl]-amide;
2,3-Dihydro-furo[2,3-b]pyridine-3-carboxylic acid [2-(6-methoxy-pyridin-3-yl)-2-morpholin-4-yl-ethyl]-amide;
(S*)-2,3-Dihydro-furo[2,3-b]pyridine-3-carboxylic acid ((S*)-3-oxo-indan-1-yl)-amide;
(S*)-2,3-Dihydro-furo[2,3-b]pyridine-3-carboxylic acid ((R*)-3-oxo-indan-1-yl)-amide;
2,3-Dihydro-furo[2,3-b]pyridine-3-carboxylic acid [2-(6-methyl-pyridin-3-yl)-2-morpholin-4-yl-ethyl]-amide;
2,3-Dihydro-furo[2,3-b]pyridine-3-carboxylic acid [2-(2-cyclopropyl-pyrimidin-5-yl)-2-morpholin-4-yl-ethyl]-amide;
2,3-Dihydro-furo[2,3-b]pyridine-3-carboxylic acid [2-morpholin-4-yl-2-(6-trifluoromethyl-pyridin-3-yl)-ethyl]-amide;
2,3-Dihydro-furo[2,3-b]pyridine-3-carboxylic acid 2,4-dichloro-6-(2-hydroxy-ethoxymethyl)-benzylamide;
(S*)-2,3-Dihydro-furo[2,3-b]pyridine-3-carboxylic acid ((S*)-4,6-dichloro-indan-1-yl)-amide; and
(S*)-2,3-Dihydro-furo[2,3-b]pyridine-3-carboxylic acid ((R*)-4,6-dichloro-indan-1-yl)-amide;
or a salt of such a compound.

10. A compound of formula (I) according to claim 1, selected from the group consisting of:

(S)-2,3-Dihydro-furo[2,3-b]pyridine-3-carboxylic acid 2,4-dichloro-6-trideuteromethyl-benzylamide;
(R)-2,3-Dihydro-furo[2,3-b]pyridine-3-carboxylic acid 2,4-dichloro-6-trideuteromethyl-benzylamide;
(S*)-2,3-Dihydro-furo[2,3-b]pyridine-3-carboxylic acid ((S*)-5-chloro-indan-1-yl)-amide;
(S*)-2,3-Dihydro-furo[2,3-b]pyridine-3-carboxylic acid ((R*)-5-chloro-indan-1-yl)-amide;
(S*)-2,3-Dihydro-furo[2,3-b]pyridine-3-carboxylic acid ((S*)-7-chloro-indan-1-yl)-amide;
(S*)-2,3-Dihydro-furo[2,3-b]pyridine-3-carboxylic acid ((R*)-7-chloro-indan-1-yl)-amide;
2,3-Dihydro-furo[2,3-b]pyridine-3-carboxylic acid 2-chloro-4-trifluoromethyl-benzylamide;
2,3-Dihydro-furo[2,3-b]pyridine-3-carboxylic acid (5,7-dichloro-indan-1-yl)-amide;
2,3-Dihydro-furo[2,3-b]pyridine-3-carboxylic acid [3-(2,4-dichloro-phenyl)-propyl]-amide;
(S)-2,3-dihydrofuro[2,3-b]pyridine-3-carboxylic acid ((R)-1,2,3,4-tetrahydronaphthalen-1-yl)-amide;
(R)-2,3-dihydrofuro[2,3-b]pyridine-3-carboxylic acid ((R)-1,2,3,4-tetrahydronaphthalen-1-yl)-amide;
2,3-Dihydro-furo[2,3-b]pyridine-3-carboxylic acid (7-chloro-indan-1-yl)-amide;
(S)-2,3-Dihydro-furo[2,3-b]pyridine-3-carboxylic acid ((R)-8-chloro-1,2,3,4-tetrahydronaphthalen-1-yl)-amide;
(R)-2,3-Dihydro-furo[2,3-b]pyridine-3-carboxylic acid ((R)-8-chloro-1,2,3,4-tetrahydronaphthalen-1-yl)-amide;
2,3-Dihydro-furo[2,3-b]pyridine-3-carboxylic acid (7-bromo-indan-1-yl)-amide;
2,3-Dihydro-furo[2,3-b]pyridine-3-carboxylic acid 2,4,6-trichloro-benzylamide;
7-Oxy-2,3-dihydro-furo[2,3-b]pyridine-3-carboxylic acid 2,4-dichloro-6-methyl-benzylamide;
2,3-Dihydro-furo[2,3-b]pyridine-3-carboxylic acid (5,7-dichloro-1-oxo-indan-2-yl)-amide;
2,3-Dihydro-furo[2,3-b]pyridine-3-carboxylic acid 4-chloro-2-hydroxymethyl-benzylamide; and
2,3-Dihydro-furo[2,3-b]pyridine-3-carboxylic acid 2-chloro-6-hydroxymethyl-benzylamide;
or a salt of such a compound.

11. A pharmaceutical composition containing, as active principle, a compound of formula (I) according claim 1, or a pharmaceutically acceptable salt thereof, and at least one therapeutically inert excipient.

12. A method for the treatment of pain comprising administering to a patient in need thereof a compound of formula (I) according to claim 1, or of a pharmaceutically acceptable salt thereof.

13. The method of claim 12, wherein the compound of Formula (I), or a pharmaceutically acceptable salt thereof, is administered in a pharmaceutical composition comprising at least one therapeutically inert excipient.

14. A compound of formula (I) according to claim 2, wherein n represents 1; or a salt of such a compound.

15. A compound of formula (I) according to claim 2, wherein n represents 2; or a salt of such a compound.

16. A compound of formula (I) according to claim 2, wherein X represents —N—; or a salt of such a compound.

* * * * *